United States Patent
Hendon et al.

(10) Patent No.: US 12,213,721 B2
(45) Date of Patent: Feb. 4, 2025

(54) SYSTEM, METHOD AND COMPUTER-ACCESSIBLE MEDIUM FOR CATHETER-BASED OPTICAL DETERMINATION OF MET-MYOGLOBIN CONTENT FOR ESTIMATING RADIOFREQUENCY ABLATED, CHRONIC LESION FORMATION IN TISSUE

(71) Applicant: THE TRUSTEES OF COLUMBIA UNIVERSITY IN THE CITY OF NEW YORK, New York, NY (US)

(72) Inventors: Christine Hendon, Riverdale, NY (US); Rajinder Singh-Moon, Mastic, NY (US); Soo Young Park, Seoul (KR)

(73) Assignee: THE TRUSTEES OF COLUMBIA UNIVERSITY IN THE CITY OF NEW YORK, NY (US)

( * ) Notice: Subject to any disclaimer, the term of this patent is extended or adjusted under 35 U.S.C. 154(b) by 482 days.

(21) Appl. No.: 16/864,415

(22) Filed: May 1, 2020

(65) Prior Publication Data
US 2020/0330145 A1 Oct. 22, 2020

Related U.S. Application Data

(63) Continuation-in-part of application No. 16/259,014, filed on Jan. 28, 2019, now abandoned, and a
(Continued)

(51) Int. Cl.
*A61B 18/12* (2006.01)
*G16H 20/40* (2018.01)
(Continued)

(52) U.S. Cl.
CPC ............. *A61B 18/12* (2013.01); *G16H 20/40* (2018.01); *A61B 5/14546* (2013.01);
(Continued)

(58) Field of Classification Search
CPC . A61B 18/12; A61B 18/1206; A61B 18/1492; A61B 2017/00061;
(Continued)

(56) References Cited

U.S. PATENT DOCUMENTS 5,762,609 A * 6/1998 Benaron ................ A61B 18/00
606/34
5,871,443 A 2/1999 Edwards et al.
(Continued)

FOREIGN PATENT DOCUMENTS

WO 2006055741 A1 5/2006
WO 20152015/054684 A1 4/2015

OTHER PUBLICATIONS

Singh-Moon et al, "Towards Optical Monitoring of Radiofrequency Ablation Extent for Atrial Fibrillation", 2015 IDDD 12th Intl Symposium on Biomedical Imaging (ISBI), Jul. 23, 2015, pp. 751-755 (Year: 2015).*
(Continued)

*Primary Examiner* — Michael F Peffley
(74) *Attorney, Agent, or Firm* — Hunton Andrews Kurth LLP

(57) ABSTRACT

Exemplary system, method and computer-accessible medium for determining a characteristic(s) of a tissue(s), can be provided which can include, for example, ablating the tissue(s), illuminating the tissue(s) during the ablation procedure; and continuously determining the characteristic(s) based on the ablation and illumination procedures. The tissue(s) can be ablated using radiofrequency ablation. The illumination procedure can be performed with a radiation in a visible spectrum.

18 Claims, 67 Drawing Sheets

Related U.S. Application Data continuation-in-part of application No. 15/758,639, filed as application No. PCT/US2016/051293 on Sep. 12, 2016, now abandoned.

(60) Provisional application No. 62/968,629, filed on Jan. 31, 2020, provisional application No. 62/622,267, filed on Jan. 26, 2018, provisional application No. 62/217,518, filed on Sep. 11, 2015.

(51) Int. Cl.

| | |
|---|---|
| A61B 5/00 | (2006.01) |
| A61B 5/145 | (2006.01) |
| A61B 5/1455 | (2006.01) |
| A61B 17/00 | (2006.01) |
| A61B 18/00 | (2006.01) |
| A61B 90/00 | (2016.01) |
| A61B 90/30 | (2016.01) |

(52) U.S. Cl.
CPC ......... *A61B 5/14552* (2013.01); *A61B 5/7264* (2013.01); *A61B 2017/00061* (2013.01); *A61B 2018/00351* (2013.01); *A61B 2018/00577* (2013.01); *A61B 2018/00642* (2013.01); *A61B 2090/061* (2016.02); *A61B 2090/306* (2016.02)

(58) Field of Classification Search
CPC ........... A61B 2018/00351; A61B 2018/00577; A61B 2018/00642; A61B 2018/00702; A61B 2018/00839; A61B 2090/061; A61B 2090/306; A61B 2218/002; A61B 5/0075; A61B 5/0084; A61B 5/14546; A61B 5/14552; A61B 5/4848; A61B 5/6852; A61B 5/7264
See application file for complete search history.

(56) References Cited

U.S. PATENT DOCUMENTS

| | | | | |
|---|---|---|---|---|
| 6,442,408 | B1* | 8/2002 | Wenzel | G01N 21/49 |
| | | | | 250/341.8 |
| 8,123,745 | B2* | 2/2012 | Beeckler | A61B 5/1459 |
| | | | | 606/41 |
| 8,500,730 | B2* | 8/2013 | Lee | A61B 5/0084 |
| | | | | 606/41 |
| 8,777,945 | B2* | 7/2014 | Floume | A61B 17/2812 |
| | | | | 606/51 |
| 9,526,426 | B1* | 12/2016 | Lim | A61B 5/0084 |
| 10,143,517 | B2* | 12/2018 | Ransbury | A61B 18/1492 |
| 10,531,921 | B2* | 1/2020 | Hendriks | A61B 18/24 |
| 2002/0026188 | A1 | 2/2002 | Balbierz et al. | |
| 2006/0173359 | A1* | 8/2006 | Lin | A61B 18/1477 |
| | | | | 600/478 |
| 2007/0073277 | A1 | 3/2007 | Johnson et al. | |
| 2008/0247506 | A1 | 10/2008 | Maschke | |
| 2009/0143774 | A1 | 6/2009 | Uzunbajakava et al. | |
| 2010/0121318 | A1 | 5/2010 | Hancock et al. | |
| 2012/0078117 | A1* | 3/2012 | Okada | A61B 5/743 |
| | | | | 600/476 |
| 2014/0171806 | A1* | 6/2014 | Govari | A61B 5/0036 |
| | | | | 600/476 |
| 2015/0057530 | A1* | 2/2015 | Roggeveen | A61B 17/3401 |
| | | | | 600/424 |

OTHER PUBLICATIONS

Celik, H. et al , "Intrinsic contrast for characterization of acute radiofrequency ablation lesions," Circulation. Arrhythmia and electrophysiology, vol. 7, pp. 718-727, 2014 [Cited in parent U.S. Appl. No. 16/259,014, filed Jan. 28, 2019].

Zipes, D.P. et al., Cardiac electrophysiology : from cell to bedside, Sixth edition. ed. (Elsevier/Saunders, Philadelphia, PA, 2014), p. 1365 pages [Cited in parent U.S. Appl. No. 16/259,014, filed Jan. 28, 2019].

Swartling, J. et al., "Changes in tissue optical properties due to radio-frequency ablation of myocardium," Medical & biological engineering & computing, vol. 41, pp. 403-409, 2003 [Cited in parent U.S. Appl. No. 16/259,014, filed Jan. 28, 2019].

Singh-Moon, R.M. et al "Near-infrared spectroscopy integrated catheter for characterization of myocardial tissues: preliminary demonstrations to radiofrequency ablation therapy for atrial fibrillation," Biomed. Opt. Express, vol. 6, pp. 2494-2511, 2015 [Cited in parent U.S. Appl. No. 16/259,014, filed Jan. 28, 2019].

Reiffel, J.A. "SME Multimedia Activity" Am J Med. 2014, vol. 127, pp. e15-16 [Cited in parent U.S. Appl. No. 16/259,014, filed Jan. 28, 2019].

P. A. Wolf, P. A. et al., "Atrial Fibrillation as an Independent Risk Factor for Stroke: The Framngham Study" 1991, vol. 22, pp. 983-988 [Cited in parent U.S. Appl. No. 16/259,014, filed Jan. 28, 2019].

Ganesan, A.N. et al., "Long-term Outcomes of Catheter Ablation of Atrial Fibrillation: A Systematic review and meta-analysis" Journal of the American Heart Association. 2013, vol. 2, pp. 1-14 [Cited in parent U.S. Appl. No. 16/259,014, filed Jan. 28, 2019].

Wood, M.A. "Exposing Gaps in Linear Radiofrequency Lesions" Circ Arrhythm Electrophysiol. 2011, vol. 4, pp. 257-259 [Cited in parent U.S. Appl. No. 16/259,014, filed Jan. 28, 2019].

Fleming, C.P. et al., "Toward guidance of epicardial cardiac radiofrequency ablation therapy using optical coherence tomography" Journal of biomedical optics. 2010, vol. 15, pp. 1-8 [Cited in parent U.S. Appl. No. 16/259,014, filed Jan. 28, 2019].

Fleming, C. P. et al., "Extracting three-dimensional orientation and tractography of myofibers using optical coherence tomography" Optics express. 2010, vol. 18, pp. 3079-3092 [Cited in parent U.S. Appl. No. 16/259,014, filed Jan. 28, 2019].

Fu, X. et al., "Integrated FRA/OCT catheter for real-time guidance of cardiac RFA therapy (Conference presentation)" Proc. SPIE 2016, pp. 1-2 [Cited in parent U.S. Appl. No. 16/259,014, filed Jan. 28, 2019].

Fu, X et al., "Fiber-optic catheter-based polarization-sensitive OCT for radio-frequency ablation monitoring" Optics letters. 2014, vol. 39, pp. 5066-5069 [Cited in parent U.S. Appl. No. 16/259,014, filed Jan. 28, 2019].

Herranz, D. et al., "Novel Catheter enabling simultaneous radiofrequency ablation and optical coherence reflectometry" Biomedical optics express. 2015, vol. 6, pp. 3268-3275 [Cited in parent U.S. Appl. No. 16/259,014, filed Jan. 28, 2019].

Mercader, M. et al., "Use of Endogenous NADH florescence for real-time in situ visualization of epicardial radiofrequency ablation and gaps" American journal of physiology. Heart and circulatory physiology. 2012, vol. 302, pp. 2131-2138 [Cited in parent U.S. Appl. No. 16/259,014, filed Jan. 28, 2019].

Swift, L. et al., "Visualization of Epicardial Cryoablation Lesion using Endogenous Tissue Florescence" Arrhythrn Electrophysiol. 2014, vol. 7, pp. 929-937 [Cited in parent U.S. Appl. No. 16/259,014, filed Jan. 28, 2019].

Gil, D. A. et al., "Autofluorescence hyperspectral imaging of radiofrequency ablation lesions in porcine cardiac tissue" J Biophotonics. 2017, vol. 10, pp. 1008-1017 [Cited in parent U.S. Appl. No. 16/259,014, filed Jan. 28, 2019].

Muselimyan, N. et al., "Seeing the Invisible: Revealing Atrial Ablation lesions using Hyperspectral Imaging Approach" PLoS One. 2016, vol. 11, pp. 1-15 [Cited in parent U.S. Appl. No. 16/259,014, filed Jan. 28, 2019].

Demos, S. G. et al., "Real Time assessment of RF cardiac tissue ablation with optical spectroscopy" Optics express. 2008, vol. 16, pp. 15286-15296 [Cited in parent U.S. Appl. No. 16/259,014, filed Jan. 28, 2019].

Mourant, J.R. et al., "Measuring absorption coefficients in small vols. of highly scattering media: source-detector separations for which path lengths do not depend on scattering properties" Applied optics. 1997, vol. 36, pp. 5655-5661 [Cited in parent U.S. Appl. No. 16/259,014, filed Jan. 28, 2019].

(56) References Cited

OTHER PUBLICATIONS

Mourant, J.R. et al., "Non-invasive measurement of chemotherapy drug concentrations in tissue: preliminary demonstrations of in vivo measurements," Bigio Physics in medicine and biology. 1999, vol. 44, pp. 1397-1417 [Cited in parent U.S. Appl. No. 16/259,014, filed Jan. 28, 2019].

Singh-Moon, R.P. et al., "Towards Optical Monitoring of Radiofrequency ablation extent for atrial fibrillation" Biomed Imaging. 2015, pp. 751-755 [Cited in parent U.S. Appl. No. 16/259,014, filed Jan. 28, 2019].

Singh-Moon, R. P. "Near-Infrared Spectroscopy integrated catheter for characterization of myocardial tissues: preliminary demonstrations to radiofrequency ablation therapy for atrial fibrillation" Biomed. Opt. Express. 2015, vol. 6, pp. 2494-2511 [Cited in parent U.S. Appl. No. 16/259,014, filed Jan. 28, 2019].

Singh-Moon, R.P. et al., "Optical Spectroscopy facilitated characterization of acute lesions" Biomedical Optics Congress. 2016, pp. 1-3 [Cited in parent U.S. Appl. No. 16/259,014, filed Jan. 28, 2019].

Yao, X. et al., "Myocardial imaging using ultrahigh-resolution spectral domain optical coherence tomography" Journal of biomedical optics. 2016, vol. 21, pp. 1-14 [Cited in parent U.S. Appl. No. 16/259,014, filed Jan. 28, 2019].

Swartling, J. et al., "Changes in tissue optical properties due to radio-frequency ablation of myocardium" Medical & biological engineering & computing. 2003, vol. 41, pp. 403-409 [Cited in parent U.S. Appl. No. 16/259,014, filed Jan. 28, 2019].

Thomsen, S. L. J et al., "Microscopic correlates of macroscopic optical property changes during thermal coagulation of myocardium" Proc. Soc. Photo—Opt. Instrum. Eng. 1202. 1990, pp. 2-10 [Cited in parent U.S. Appl. No. 16/259,014, filed Jan. 28, 2019].

Bowen, W. J. "The Absorption spectra and extinction coefficients of myoglobin" The Journal of biological chemistry. 1949, vol. 179, pp. 235-245 [Cited in parent U.S. Appl. No. 16/259,014, filed Jan. 28, 2019].

Celik, H. et al., "Intrinsic Contrast for Characterization of Acute radiofrequency ablation lesions" Circ Arrhythm Electrophysiol. 2014, vol. 7, pp. 718-727 [Cited in parent U.S. Appl. No. 16/259,014, filed Jan. 28, 2019].

Antonini, E. et al., "Hemoglobin and myoglobin in their reactions with ligands," North-Holland Pub. Co., Amsterdam, 1971, pp. 1-233 [Cited in parent U.S. Appl. No. 16/259,014, filed Jan. 28, 2019].

Dickfeld, T. et al., "Characterization of radiofrequency ablation lesion with Gadolinium-Enhanced cardivascular magnetic resonance imaging," Journal of the American College of Cardiology. 2006, vol. 47, pp. 370-378 [Cited in parent U.S. Appl. No. 16/259,014, filed Jan. 28, 2019].

Bai, R. et al., "Worldwide Experience with the robotic naviagation system in catheter ablation of atrial fibrillation: Methodology, efficacy and safety" J Cardiovasc Electrophysiol. 2012, vol. 23, pp. 820-826 [Cited in parent U.S. Appl. No. 16/259,014, filed Jan. 28, 2019].

Di Biase, L. et al., "Ablation of Atrial Fibrillation Utilizing Robotic Catheter Navigation in Comparison to Manual Navigation and Ablation" J Cardiovasc Electrophysiol. 2009, vol. 20, pp. 1328-1335 [Cited in parent U.S. Appl. No. 16/259,014, filed Jan. 28, 2019].

Saliba, W. et al., "Atrial Fibrillation Ablation using a robotic catheter remote control system" Journal of the American College of Cardiology. 2008, vol. 51, pp. 2407-2411 [Cited in parent U.S. Appl. No. 16/259,014, filed Jan. 28, 2019].

Fleming, C.P. et al., "First in vivo Real-time imaging of endocaridal" The Journal of Innovations in Cardiac Rhythm Management. 2011, pp. 199-201 [Cited in parent U.S. Appl. No. 16/259,014, filed Jan. 28, 2019].

Fleming, C.P. et al., "Real-time monitoring of cardiac radio-frequency ablation" Journal of biomedical optics. 2010, vol. 15, pp. 1-3 [Cited in parent U.S. Appl. No. 16/259,014, filed Jan. 28, 2019].

Lindbergh, T. et al., "Intramyocardial oxygen transport by quantitative diffuse reflectance spectroscopy in calves" Journal of biomedical optics. 2010, vol. 15, pp. 1-11 [Cited in parent U.S. Appl. No. 16/259,014, filed Jan. 28, 2019].

Gan, Y. et al., "Automated Classification of Optical coherence tomography images of human atrial tissue" Journal of biomedical optics. 2016, vol. 21, pp. 1-12 [Cited in parent U.S. Appl. No. 16/259,014, filed Jan. 28, 2019].

International Search Report and Written Opinion mailed on Dec. 5, 2016 for International Patent Application No. PCT/US2016/051293.

\* cited by examiner

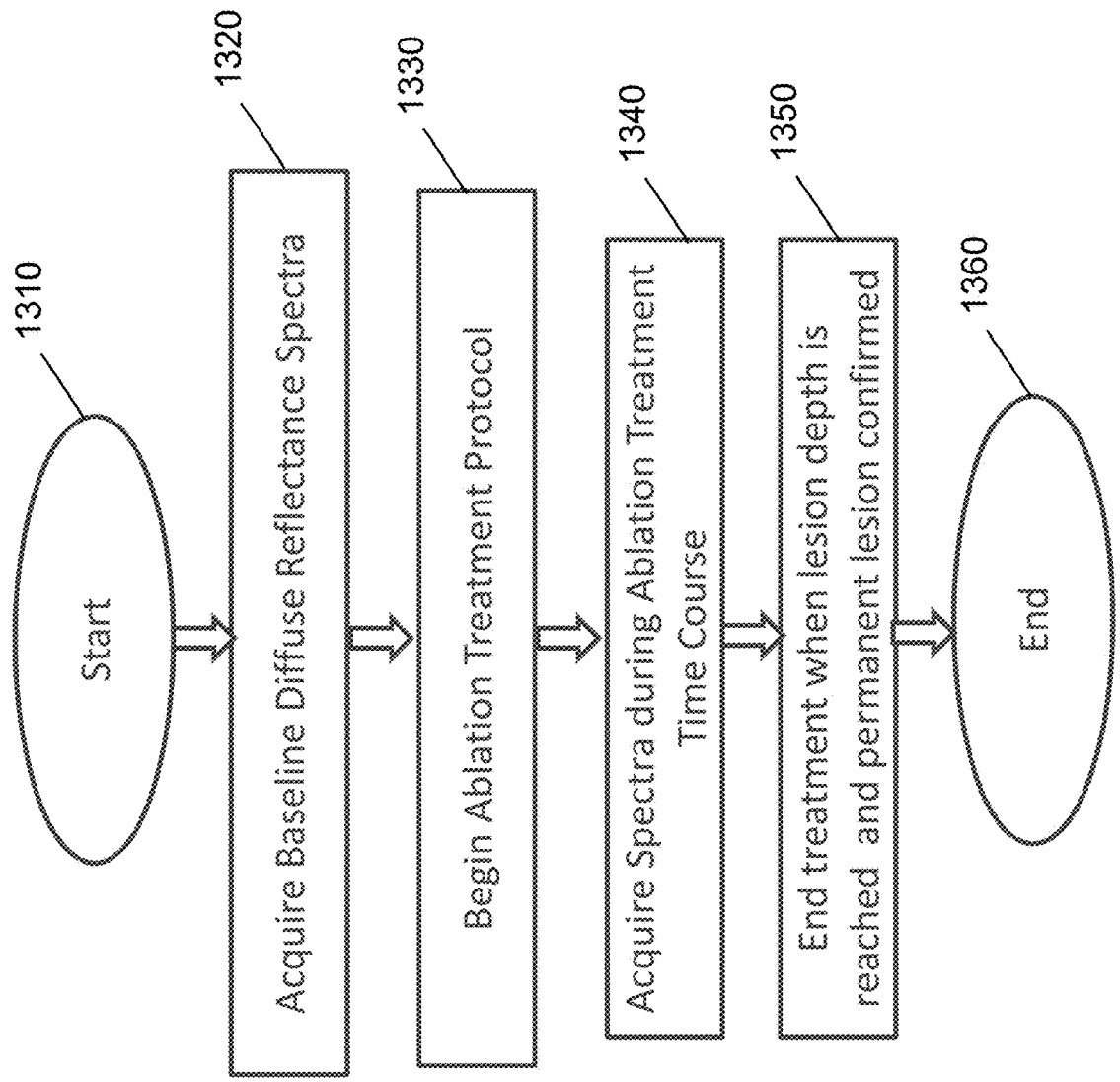

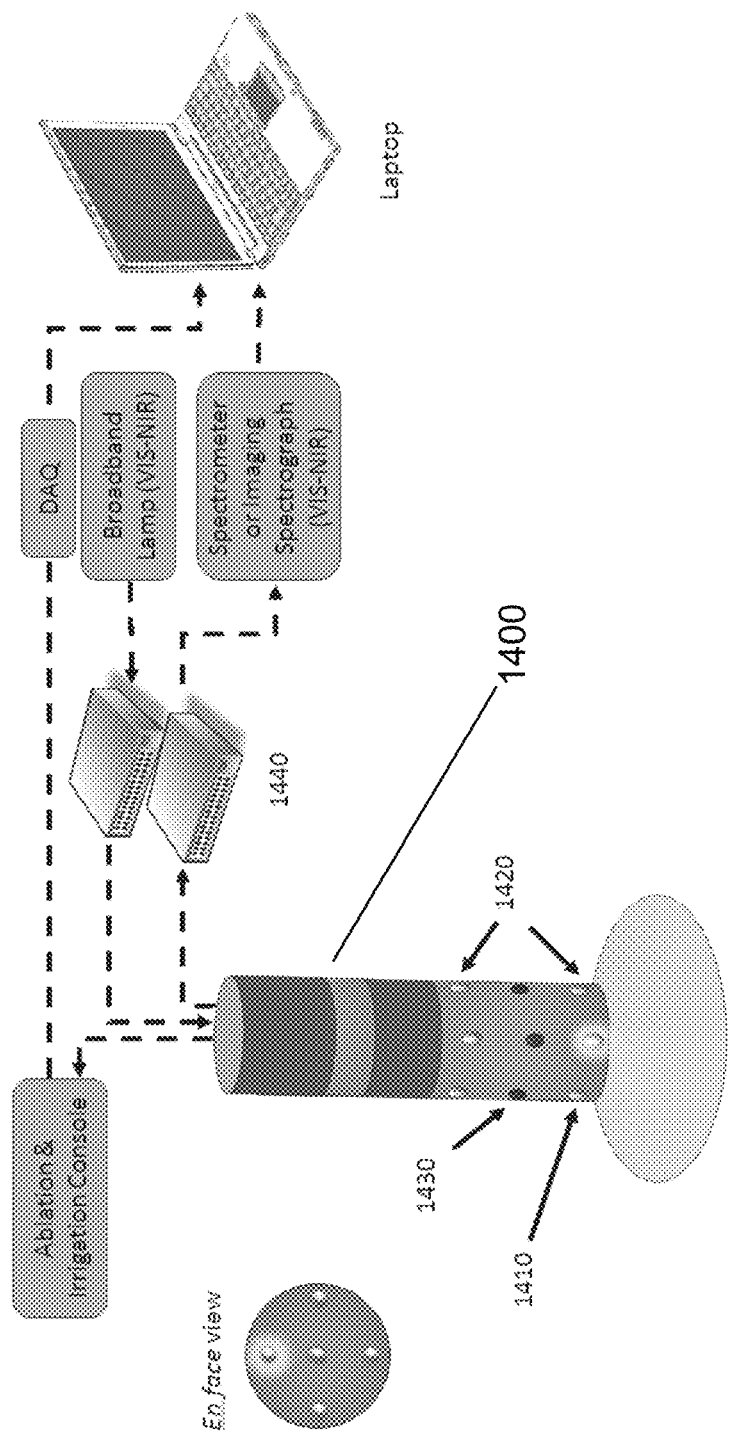

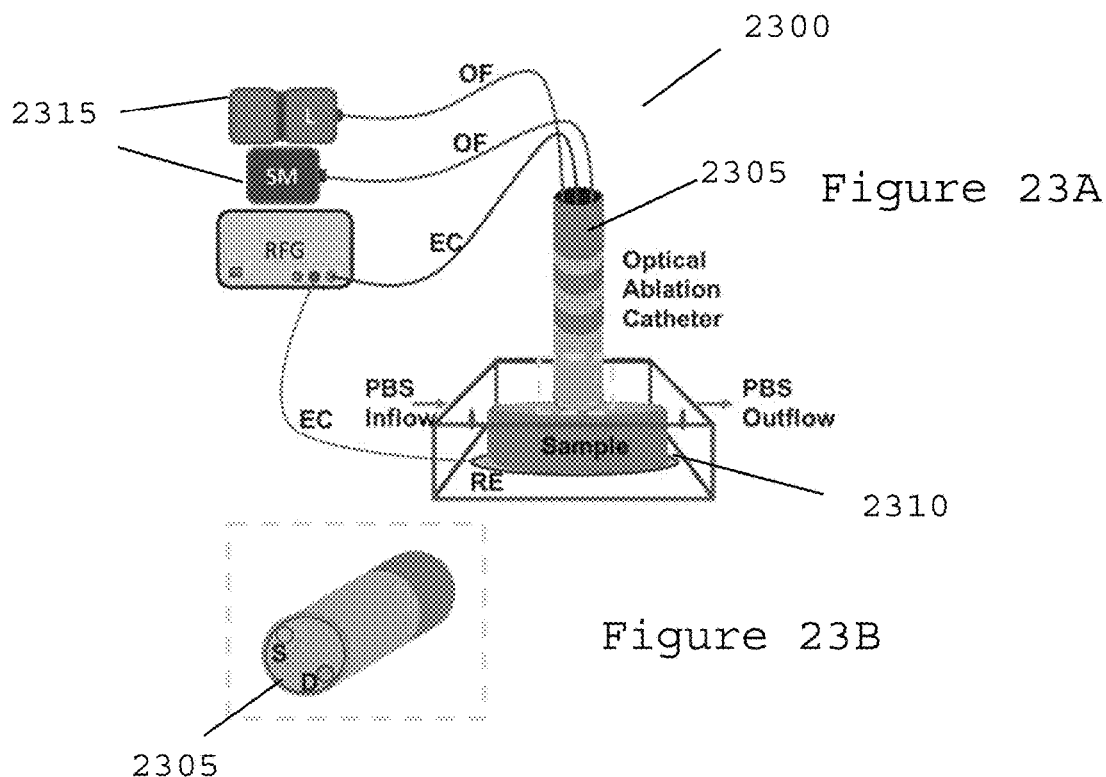
Figure 23A
Figure 23B
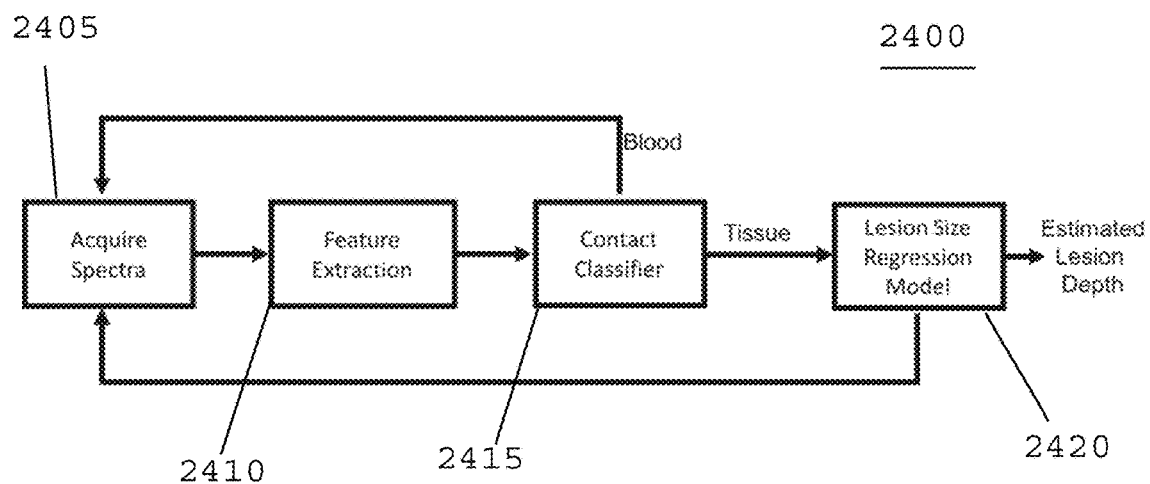
Figure 24

Resulting TTC cross-section
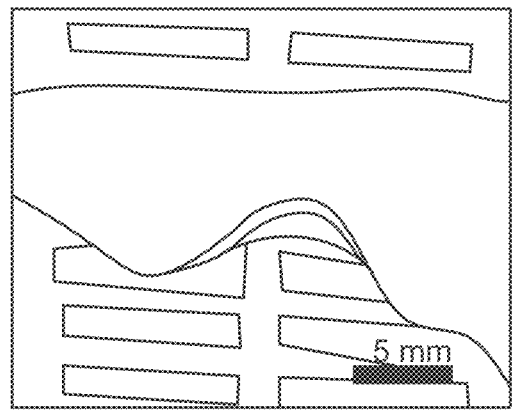
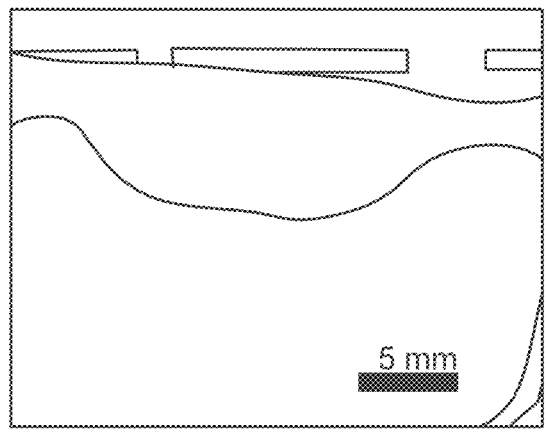
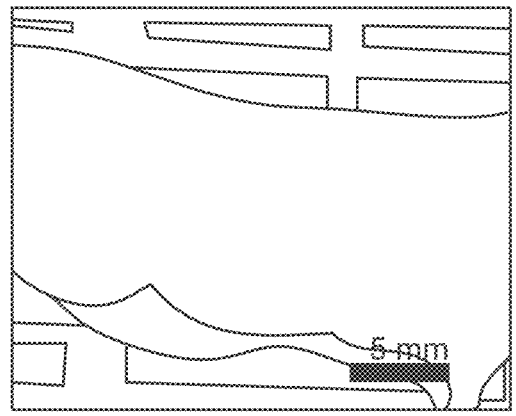
Figure 29B

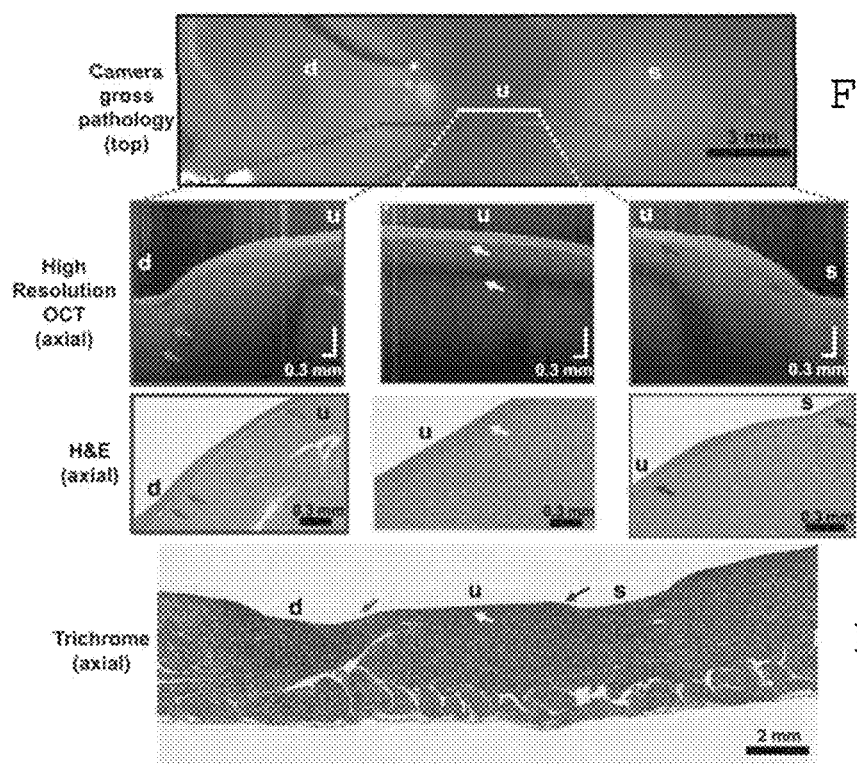

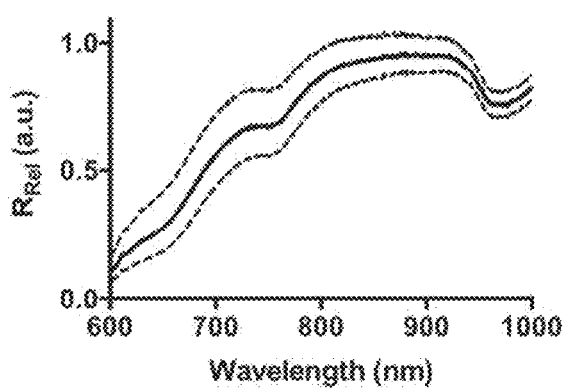 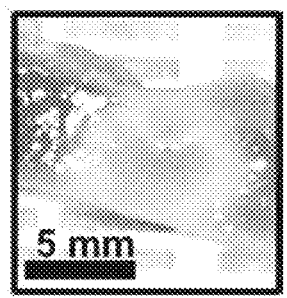
Figure 31A
Figure 31B

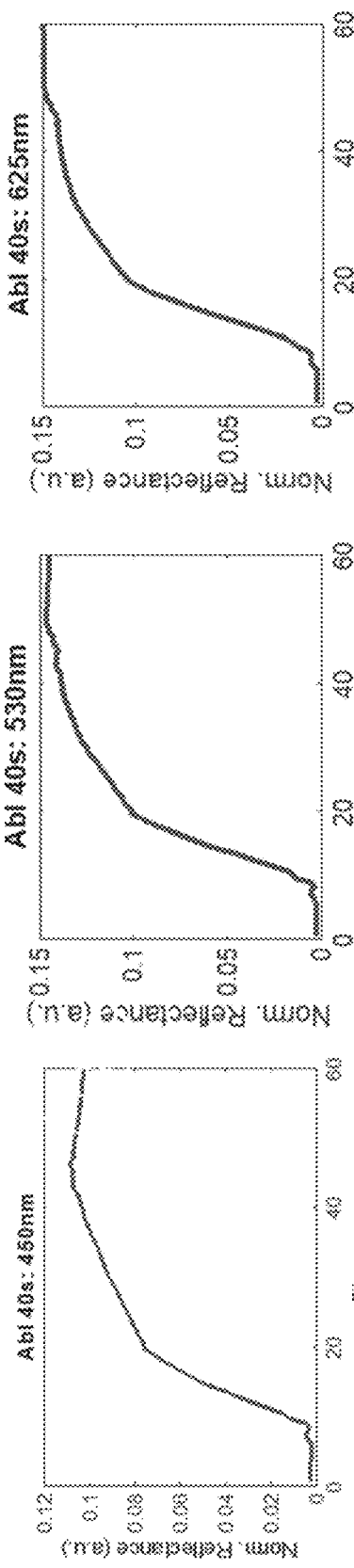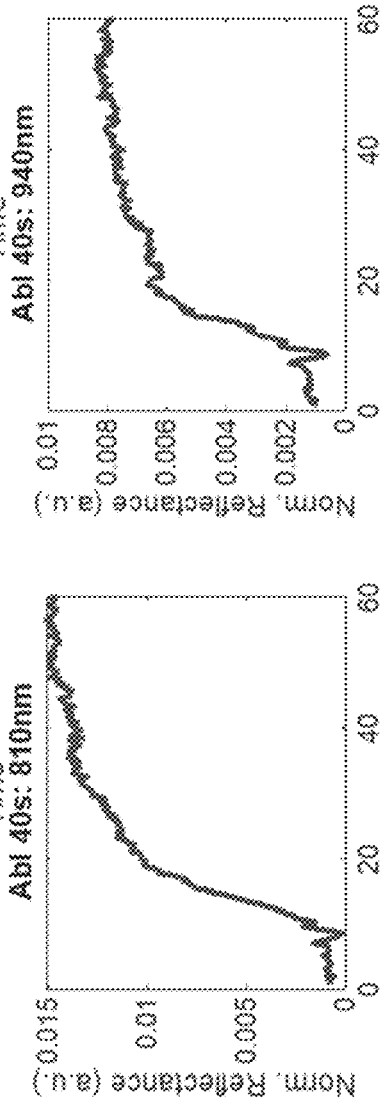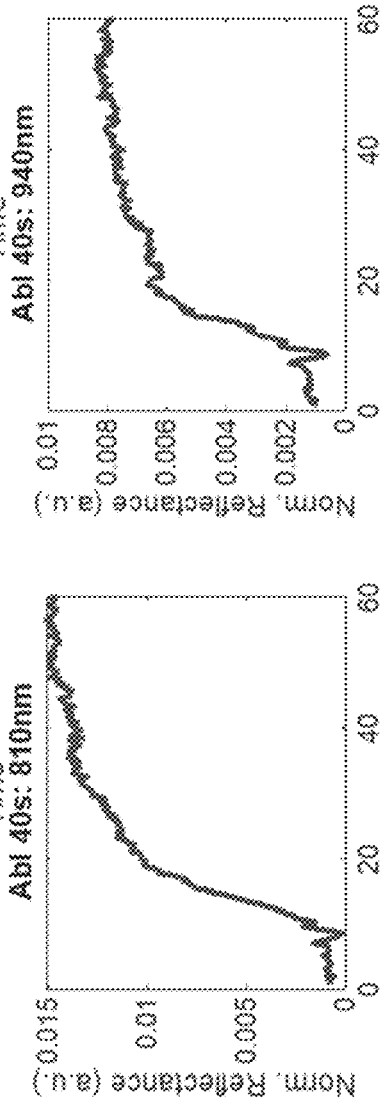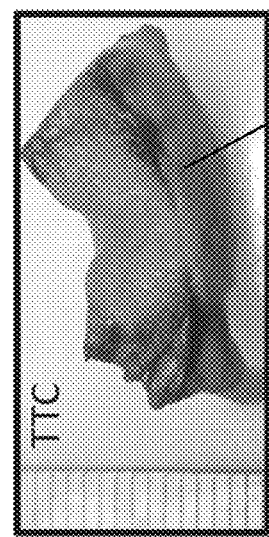
Figure 39A
Figure 39B
Figure 39C
Figure 39D
Figure 39E
Figure 39F

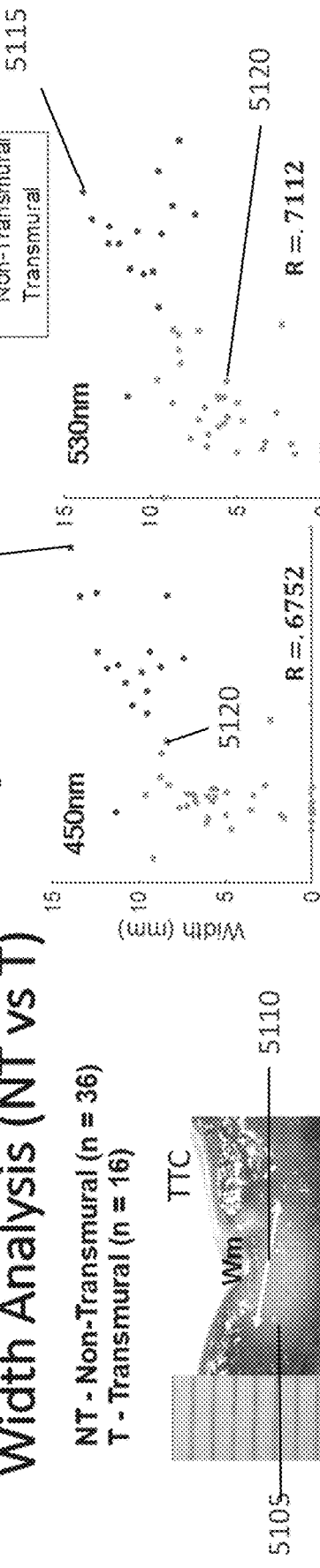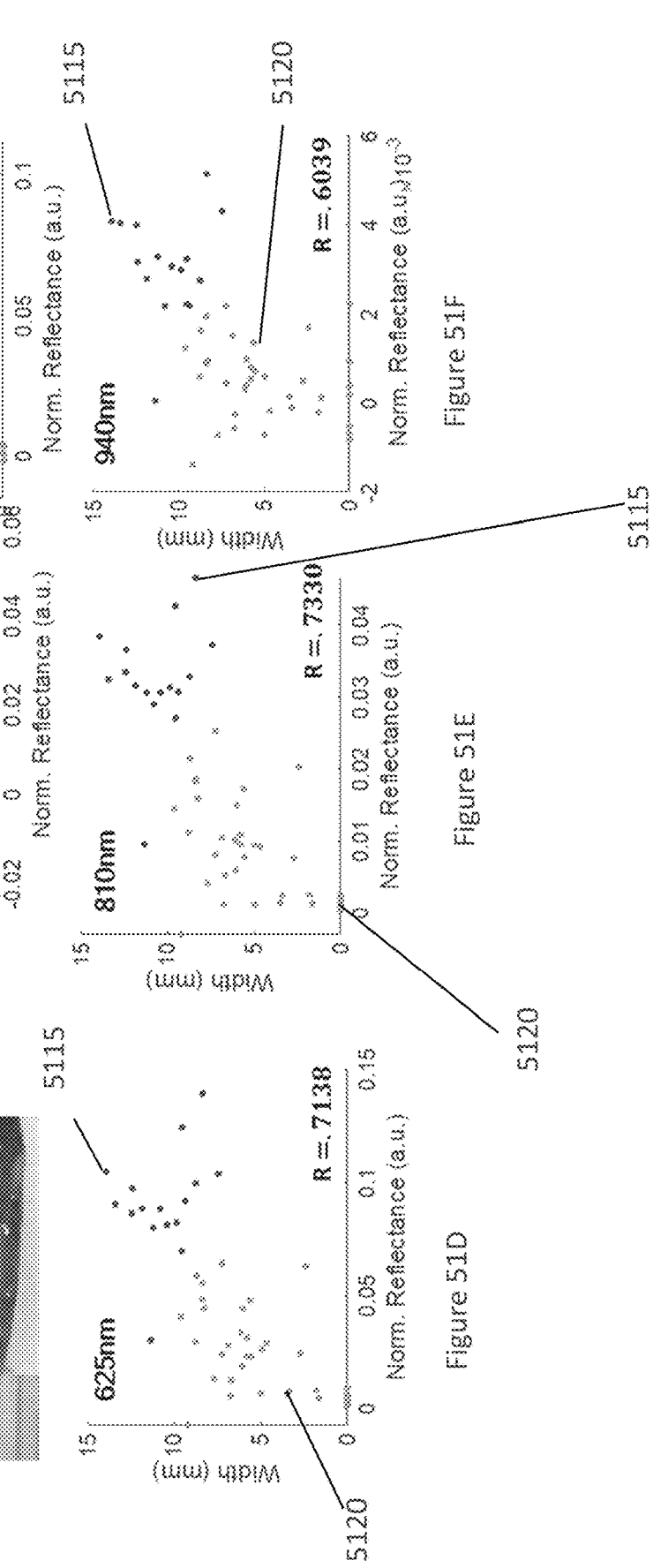

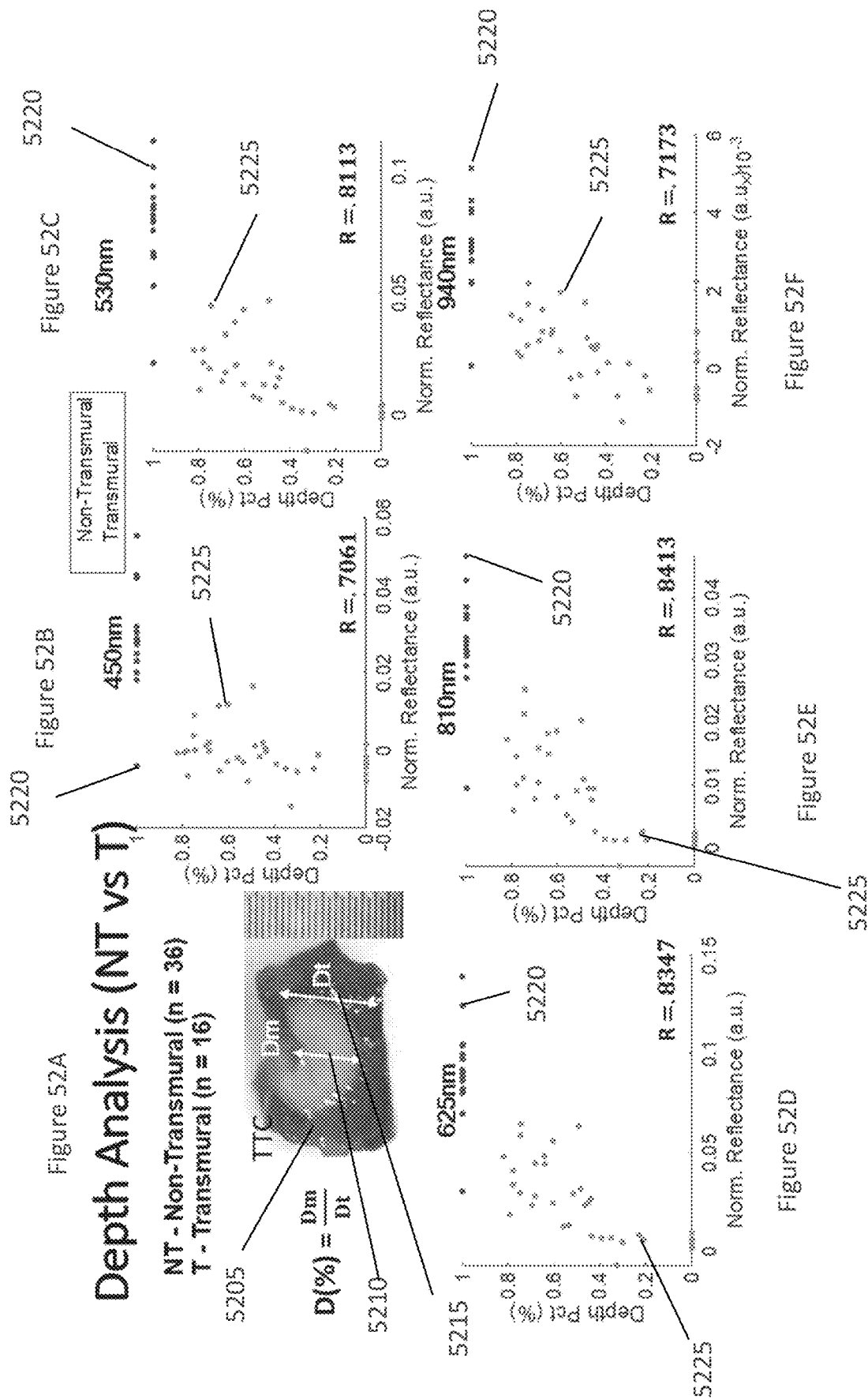

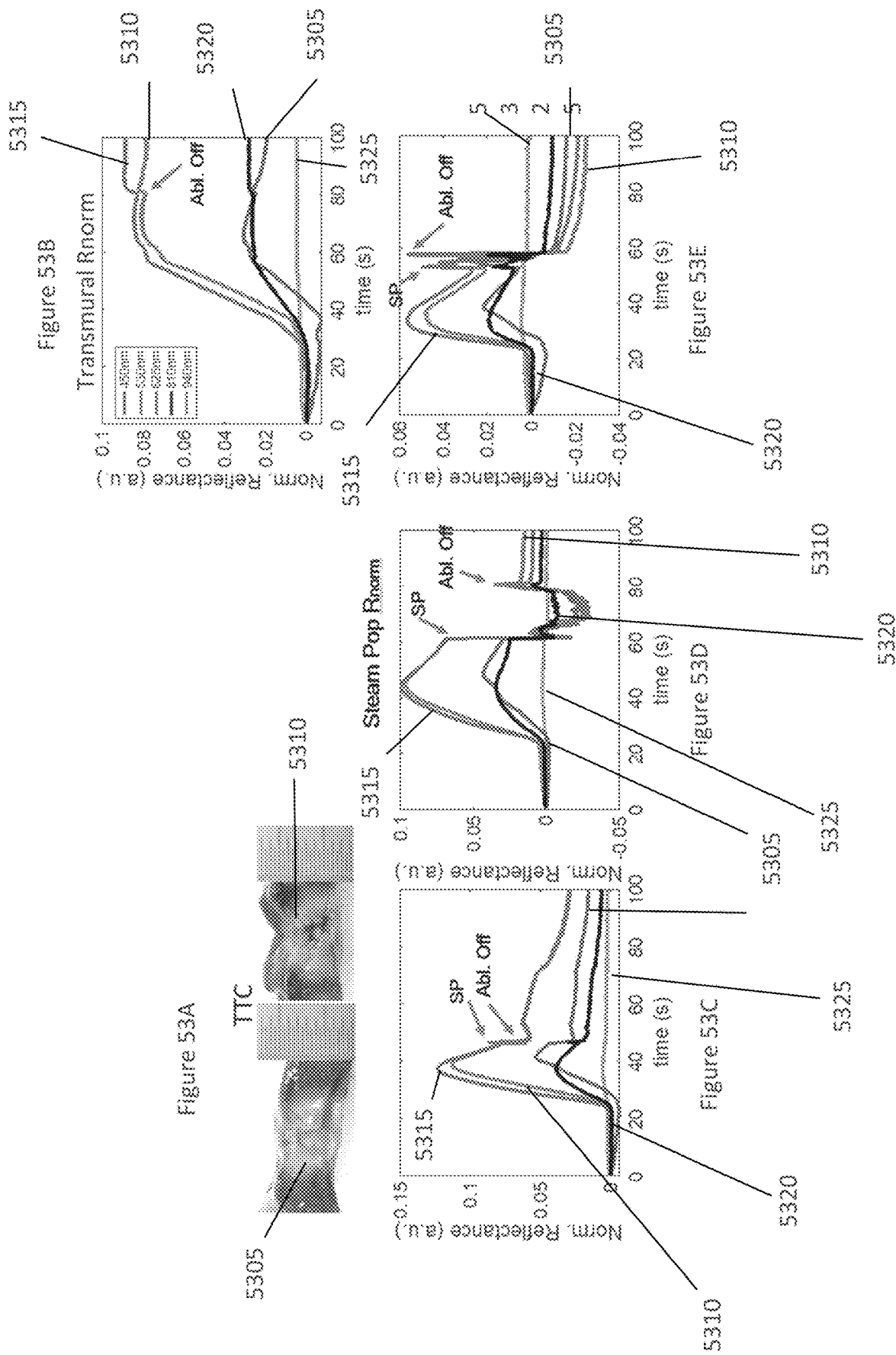

SYSTEM, METHOD AND COMPUTER-ACCESSIBLE MEDIUM FOR CATHETER-BASED OPTICAL DETERMINATION OF MET-MYOGLOBIN CONTENT FOR ESTIMATING RADIOFREQUENCY ABLATED, CHRONIC LESION FORMATION IN TISSUE

CROSS-REFERENCE TO RELATED APPLICATION(S)

This application is a continuation-in-part of and relates to U.S. patent application Ser. No. 15/758,639, filed on Mar. 8, 2018, and of U.S. patent application Ser. No. 16/259,014, filed on Jan. 28, 2019, both now abandoned, the entire disclosures of which are incorporated herein by reference. This application also relates to International Patent Application No. PCT/US2016/051293, filed on Sep. 12, 2016, the entire disclosure of which is incorporated herein by reference. Additionally, this application relates to U.S. Provisional Patent Application No. 62/217,518, filed on Sep. 11, 2015, U.S. Provisional Patent Application Ser. No. 62/622, 267, filed on Jan. 26, 2018, and U.S. Provisional Patent Application Ser. No. 62/968,629, filed on Jan. 31, 2020, the entire disclosures of which are incorporated herein by reference.

STATEMENT REGARDING FEDERALLY SPONSORED RESEARCH

This invention was made with government support under Grant No. HL127776, awarded by the National Institutes of Health, and Grant No. 1454365, awarded by the National Science Foundation. The government has certain rights in this invention.

FIELD OF THE DISCLOSURE

The present disclosure relates generally to the optical determination of met-myoglobin content, and more specifically, to exemplary embodiments of exemplary system, method and computer-accessible medium for catheter-based optical determination of met-myoglobin content for estimating radiofrequency ablated, chronic lesion formation in tissue (e.g., atrial tissue).

BACKGROUND INFORMATION

Single-procedure success of radiofrequency ablation ("RFA") therapies has been largely limited by an inability to characterize lesion sufficiency. Momentarily successful conduction blocks may not be indicative of long-term sustained electrical blockage due to transient effects of edema. (See, e.g., References 1 and 2). Studies have shown that the necrotic lesion core exhibits increased ferric content consistent with a rise in tissue met-myoglobin, as compared to viable tissue. (See, e.g., References 1 and 3).

Atrial fibrillation ("AFib"), characterized by rapid disorganized electrical activity in the upper heart chambers, can be associated with a fivefold increase in stroke risk, accounting for over 15% of stroke cases in the United States. (See, e.g., References 5 and 6). Radiofrequency ablation ("RFA") therapy has become an important procedure for treating drug-resistant AFib. Despite its widespread use, however, single procedure success rates have been low. Arrhythmia resurgence following initial successful ablation has been reported to occur in as many as 47% of patients, requiring additional procedures to achieve a sustained effect. (See, e.g., Reference 7). The aim of RFA therapy can be to modify the underlying cardiac tissue substrate by strategic anatomical lesion placement in order to disrupt arrhythmogenic electrical pathways and restore sinus rhythm. In principle, effective treatment can be directly dependent on lesion characteristics such as continuity and transmurality. Current methods for validating lesion adequacy examine regional differences in electrical activity while attempting to provoke an arrhythmic event, either pharmacologically or through pacing. (See, e.g., Reference 8). However, non-transmural lesions can also exhibit reduced excitability and short-term electrical quiescence, elusively suggesting effective treatment, while tissues can eventually recover and conduct. (See, e.g., Reference 8). Despite its unquestionable significance for ensuring treatment success, currently no method exists to directly assess the extent of lesion formation in the acute setting. Such a method could potentially improve procedural efficacy by enabling intraoperative detection of undertreated sites despite transient effects.

There were certain optical methods previously described for evaluating acute thermal injury immediately following RF treatment. For example, in ventricular tissue, direct visualization of the myocardium by Optical Coherence Tomography ("OCT") has been shown to reliably discriminate between ablated, necrotic tissue and untreated tissue. (See, e.g., References 9-13). However, inherent depth limitation of OCT (e.g., <1 mm in cardiac tissue) renders the procedure unsuitable for lesion transmurality assessment. NADH autofluorescence imaging has been demonstrated to correspond well with epicardial lesion boundaries. (See, e.g., References 14 and 15). Such procedure generally relies on the fact that ablated tissues exhibit impaired mitochondrial function compared to viable tissues. More recently, atrial lesion assessment has been demonstrated based on spectral signatures of UV-excited autofluorescence using a benchtop hyperspectral imaging system. (See, e.g., References 16 and 17). Although there have been several reports on optical lesion assessment, few studies have shown lesion size estimation within a configuration conducive for deploying in an intraoperative setting.

Alternatively, diffuse reflectance spectroscopy ("DRS"), using fiber-integrated ablation catheters, has been previously discussed as a method for assessing the degree of RF treatment to cardiac tissue. A correlation has been observed between scattering-induced changes in reflectance slope and lesion depth in bovine ventricular samples. (See, e.g., Reference 18). This procedure can be contingent upon changes in tissue microstructure and cellular morphology occurring as a result of RF treatment. An alternative approach can be to examine variations in tissue absorption; absorption related changes within DR spectra reflect changes in tissue biomolecular composition, which can indicate permanent change in viability. Fiber optical geometries could be adjusted to balance the relative sensitivity of DR measurements to absorption verses scattering changes. (See, e.g., References 19 and 20). Recently our group has demonstrated a strong relationship between DRS-derived absorption and chromophore concentrations and endocardial lesion size within porcine atrial specimens. (See, e.g., References 21-23). However, this procedure requires the computationally intensive step of solving an inverse problem to recover tissue optical properties for feature extraction, which can limit its applicability for real-time lesion assessment.

Thus, it may be beneficial to provide an exemplary systems, methods and computer-accessible mediums for (i) determining at least one characteristic of at least one tissue and (ii) real-time monitoring of cardiac lesion progression using a diffuse reflectance spectroscopy integrated ablation catheter which can overcome at least the deficiency described herein above.

SUMMARY OF EXEMPLARY EMBODIMENTS

An exemplary system, method and computer-accessible medium for determining a characteristic(s) of a tissue(s), can be provided which can include, for example, ablating the tissue(s), illuminating the tissue(s) during the ablation procedure; and continuously determining the characteristic(s) based on the ablation and illumination procedures. The tissue(s) can be ablated using radiofrequency ablation. The illumination procedure can be performed with a radiation in a visible spectrum.

In some exemplary embodiments of the present disclosure, diffuse reflectance spectra can be received based on the illumination procedure, and the characteristic(s) can be determined based on the received diffuse reflectance spectra. The tissue(s) can be illuminated and the diffuse reflectance spectra can be received using a single fiber. The diffuse reflectance spectra can be inverted using an inverse Monte Carlo procedure. In certain exemplary embodiments of the present disclosure, a concentration of an oxy-myoglobin, a deoxy-myoglobin or a met-myoglobin can be determined based on the inverted diffuse reflectance spectra. An exemplary analysis of variance test or a Tukey's multiple comparison test can be performed on the concentration (e.g., the met-myoglobin concentration).

In some exemplary embodiments of the present disclosure, the inverted diffuse reflectance spectra can utilize a wavelength dependent model. A plurality of coefficients can be received based on the fitting, and the characteristic(s) can be determined based on the coefficients. The characteristic(s) can include a classification of the tissue, which can include the tissue(s) having a lesion thereon. The ablation and illumination procedures can be repeated until a permanent lesion is formed on the tissue(s).

In certain exemplary embodiments of the present disclosure, a baseline diffuse reflectance spectra associated with the tissue(s) can be determined before the ablation procedure. In some exemplary embodiments of the present disclosure, the tissue(s) can be flushed and/or the surface of the tissue can be electrically mapped An exemplary system for determining a characteristic(s) of a tissue(s) can be provided, which can include, for example a first electromagnetic radiation source configured to (i) generate a first radiation(s) and (ii) provide the first radiation(s) to the tissue(s) so as to partially ablate the tissue(s), a second electromagnetic radiation source configured to (i) generate a second radiation(s), and (ii) provide the second radiation(s) to the tissue(s), a detector arrangement configured to (i) obtain a return radiation from the tissue(s) that can be based on the second radiation(s) impacting the tissue(s) and the partial ablation(s) caused by the first radiation(s), and (ii) provide data associated with a further characteristic(s) of the returned radiation, and a computer processing arrangement configured to determine the characteristic(s) based on the data. The data can include information as to whether the tissue(s) has been permanently damaged.

In some exemplary embodiments of the present disclosure, the second radiation can be in a visible spectrum. The characteristic(s) can include a classification of the tissue, which can include the tissue(s) having a lesion thereon. A flushing arrangement(s) can be included, which can be configured to flush the tissue(s). In certain exemplary embodiments of the present disclosure, a voltage arrangement can be included, which can be configured to generate a voltage(s), where the detector arrangement can be further configured to obtain a return voltage from the tissue(s) that can be based on the second radiation(s) impacting the tissue(s). A map(s) of a surface of the tissue(s) can be generated based on the return voltage. The first radiation(s) or the second radiation(s) can be provided in a single fiber, and the detector can receive the return radiation from the single fiber.

An exemplary method for ablating tissue(s) can be provide, which can include, for example, determining a location(s) of a dead(s) portion of the tissue(s), providing the location(s) to an ablative source arrangement, moving the ablative source arrangement to a further location(s) based on one location(s), and ablating the further location(s) of the tissue(s). The determination procedure can be based on an intensity(ies) and a wavelength(s) of a radiation produced by the ablative source arrangement. In some exemplary embodiments of the present disclosure, the tissue can be flushed using a flushing arrangement and/or the tissue can be mapped using a voltage generator.

An exemplary catheter can be provided, which can include, for example a near infrared radiation generation first arrangement; a visible radiation generating second arrangement, and an ablative arrangement. The catheter can also include a flushing arrangement and/or a voltage generator.

According to another exemplary embodiment of the present disclosure, exemplary system, method and computer-accessible medium can be provided for determining a size or a dimension of a lesion(s) provided on or in an anatomical structure can be provided, which can include, for example, receiving first spectra information for the lesion(s) based on an electro-magnetic information provided to the lesion(s), extracting a feature(s) related to the lesion(s) from a model(s) provided in an electronic storage arrangement, filtering out particular spectra from the first spectra information to generate second spectra information by classifying a contact(s) for the lesion(s), and determining the size or the dimension of the lesion(s) based on the feature(s), the second spectra information, and a lesion regression model. The first spectra information can be generated based on an inverse Monte Carlo procedure. The particular spectra can be spectra determined to be unsuitable for lesion size estimation. The lesion regression model can be based on a feature vector that can include lesion optical indices and squares of the lesion optical indices. The lesion(s) can be illuminated using a fiber, and the reflectance spectra can be received based on the illumination using the fiber, and the first spectra information can be generated based on the reflectance spectra.

In some exemplary embodiments of the present disclosure, the lesion regression model can be based on a feature vector that can include lesion optical indices and squares of the lesion optical indices. The spectra determined to be unsuitable for a lesion size estimation can be determined based on a blood contamination. The generating the second spectra information can be based on a linear discriminant analysis (LDA). The second spectra information can be categorized as non-contact class or contact class using the LDA. The lesion regression model can be further based on a lesion depth of a further lesion. The lesion(s) can be illuminated using a fiber, a reflectance spectra based on the illumination can be received using the fiber, and the first spectra information can be generated based on the reflectance spectra.

In a further exemplary embodiments of the present disclosure, exemplary system for determining a size or a dimension of a lesion(s) provided on or in an anatomical structure can be provided, which can include, for example, an electromagnetic radiation source configured to generate an electromagnetic radiation, a catheter configured to (i) provide the electromagnetic radiation to the lesion(s) and (i) sample a tissue diffuse reflectance at the lesion(s) that is based on the electromagnetic radiation impacting the lesion(s); and a computer processing arrangement configured to determine the size or the dimension of the lesion(s) based on the sampled tissue diffuse reflectance. The electromagnetic radiation source can be or include a broadband light source. A longpass filter can be located between the electromagnetic radiation source and the catheter configured to filter the electromagnetic radiation.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 13 is a flow diagram of an exemplary method for treating a lesion according to an exemplary embodiment of the present disclosure;

FIG. 14 is an exemplary diagram of the exemplary catheter according to an exemplary embodiment of the present disclosure;

FIG. 23A is an exemplary schematic diagram of an exemplary catheter ablation system according to an exemplary embodiment of the present disclosure;

FIG. 23B is an exemplary diagram of a close-up view of a distal end of an ablation catheter according to an exemplary embodiment of the present disclosure;

FIG. 24 is an exemplary flow diagram for processing diffuse reflectance spectra according to an exemplary embodiment of the present disclosure;

FIG. 29B is a set of exemplary images of cross-sections of lesions according to an exemplary embodiment of the present disclosure;

FIG. 30B is an exemplary image of an ablation site according to an exemplary embodiment of the present disclosure;

FIG. 30C is a set of exemplary images of HROCT B-scans showing superficial structural features for the various tissue treatments according to an exemplary embodiment of the present disclosure;

FIG. 30D is a set of exemplary image Hematoxylin and eosin staining histological correlates according to an exemplary embodiment of the present disclosure;

FIG. 30E is an exemplary image of trichrome staining according to an exemplary embodiment of the present disclosure;

FIG. 31A is a graph of an exemplary spectral measurement of irrigated lesions according to an exemplary embodiment of the present disclosure;

FIG. 31B is an exemplary image of a triphenyl-2H-tetrazolium chloride-stained specimen according to an exemplary embodiment of the present disclosure;

FIGS. 39A-39F are exemplary graphs illustrating fiber-bundle ablation assessment and exemplary image showing ablated tissue according to an exemplary embodiment of the present disclosure;

FIGS. 51A-51F are exemplary image and graphs illustrating a width analysis for non-transmural and transmural ablation according to an exemplary embodiment of the present disclosure;

FIGS. 52A-52F are exemplary image and graphs illustrating a depth analysis for non-transmural and transmural ablation according to an exemplary embodiment of the present disclosure;

FIGS. 53A-53E are exemplary image and graphs illustrating a steam-pop analysis according to an exemplary embodiment of the present disclosure;

Figure 1:
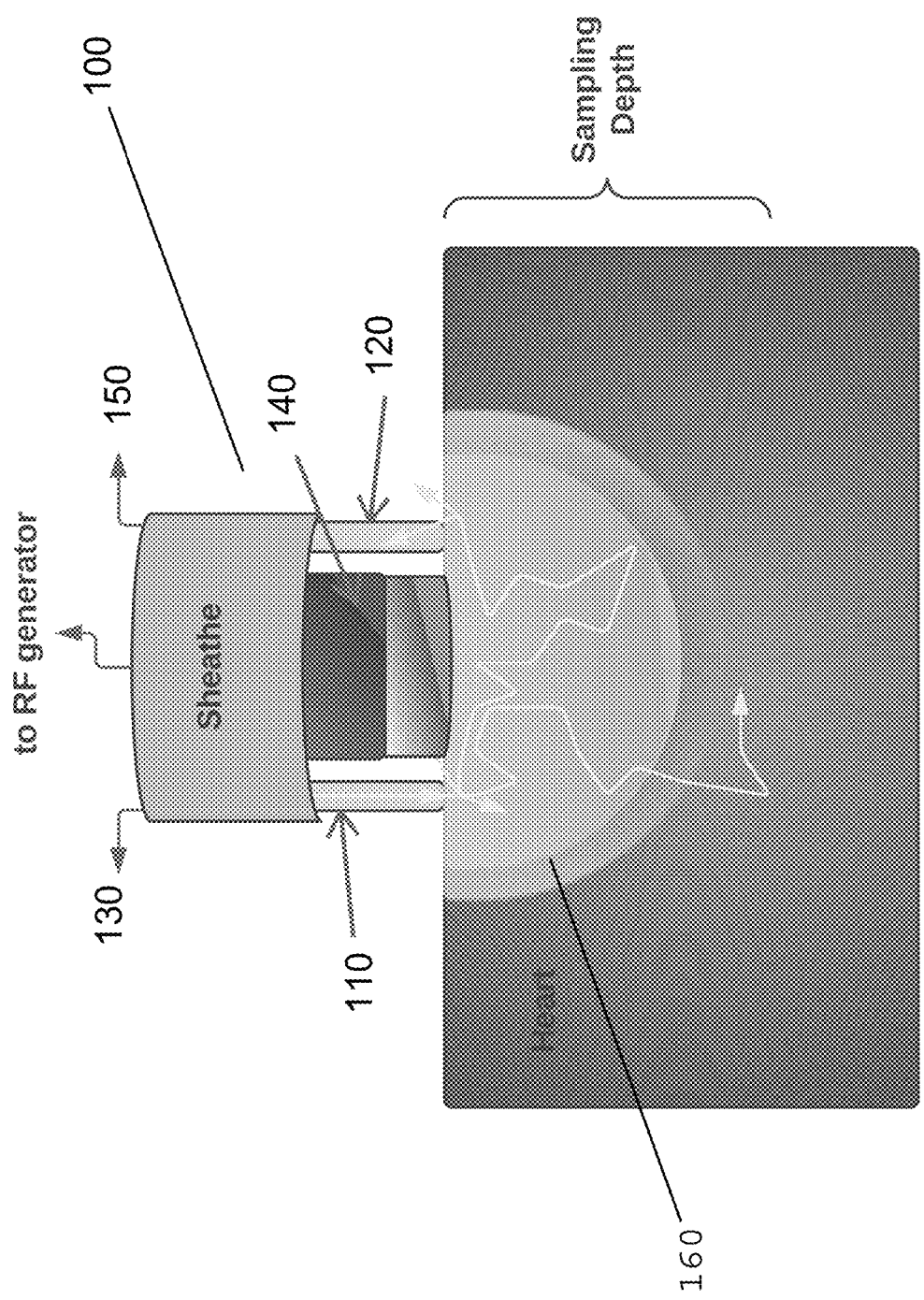
FIG. 1 is a diagram illustrating an exemplary catheter ablating and illuminating tissue according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Exemplary Catheter-Based Optical Determination of Met-Myoglobin Content for Estimating Radiofrequency Ablated, Chronic Lesion Formation in Tissue
Exemplary Method According to one exemplary embodiment of the present disclosure, a fiber-optic integrated RFA catheter was used to obtain broadband (e.g., 500-650 nm) diffuse reflectance measurements at a source-detector separation of 0.8 mm at the catheter tip. Atrial samples were excised from two fresh swine hearts and supraperfused in warm (e.g., 37° C.) phosphate buffered saline. Optical measurements were taken for three RFA-treated tissue groups: untreated (e.g., n=7), mildly treated (e.g., n=3), and moderately treated (e.g., n=4). An inverse Monte Carlo procedure was used to invert diffuse reflectance spectra to recover concentrations of oxy-myoglobin ("MbO"), deoxy-myoglobin ("Mb"), and met-myoglobin ("Mmb"). Comparisons across the groups revealed significantly greater Mmb concentrations (e.g., p<0.0001) in the moderately treated group as compared to the other two. Additionally, an increasing trend in Mmb concentration was observed for increased tissue treatment. Absorption contributions to the measured signal was modeled as a weighted sum of MbO, Mb, and Mmb extinction spectra ε (e.g., FIG. 3) as shown in the expression below:

$$\mu_a(\lambda)=c_{MbO}\times\varepsilon_{MbO}(\lambda)+c_{Mb}\times\varepsilon_{Mb}(\lambda)+c_{Mmb}\times\varepsilon_{Mmb}(\lambda) \quad (1)$$

where c can be the chromophore concentration. Reduced scattering was modeled as a weighted sum of Rayleigh and Mie scatterer as described below:

$$\mu'_s(\lambda) = a\left(\frac{\lambda}{600\ nm}\right)^{-4} + b\left(\frac{\lambda}{600\ nm}\right)^{-d}. \quad (2)$$

An analysis of variance ("ANOVA"), along with Tukey's multiple comparison test, were performed for the extracted concentrations of Mmb across the groups. A p-value of 0.5 was used to denote significance.

An optically-integrated catheter was used to measure three groups of RFA-treated, swine atria: untreated, mildly treated, and moderately treated. Concentrations for oxy-myoglobin, deoxy-myoglobin and met-myoglobin were determined using an inverse Monte Carlo scheme. Met-myoglobin concentrations were significantly greater (e.g., p<0.0001) for the moderately treated group compared to the others groups.

FIG. 1 illustrates an exemplary system setup 100 for obtaining measurements from myocardial tissues as well as the zone of resistive heating during ablation. Optical fibers can be embedded in a sheathe whose inner channel accepts an ordinary commercial RFA catheter 140. Two sets of fibers can typically be employed: illumination fiber(s) 110 and collection fibers 120. Broadband light 130 can be delivered onto the heart 160 via the illumination fiber(s). The tissue diffusely backscattered light can then be recovered by the collection fiber(s) 120 placed at some distance away from the illumination point and recorded by a spectrometer 150. Collected photons can sample the myocardium and can contain information on physiological makeup and ultrastructure of the traverse path. Fibers can be integrated into the sheath or into the ablation catheter.

Figure 2:
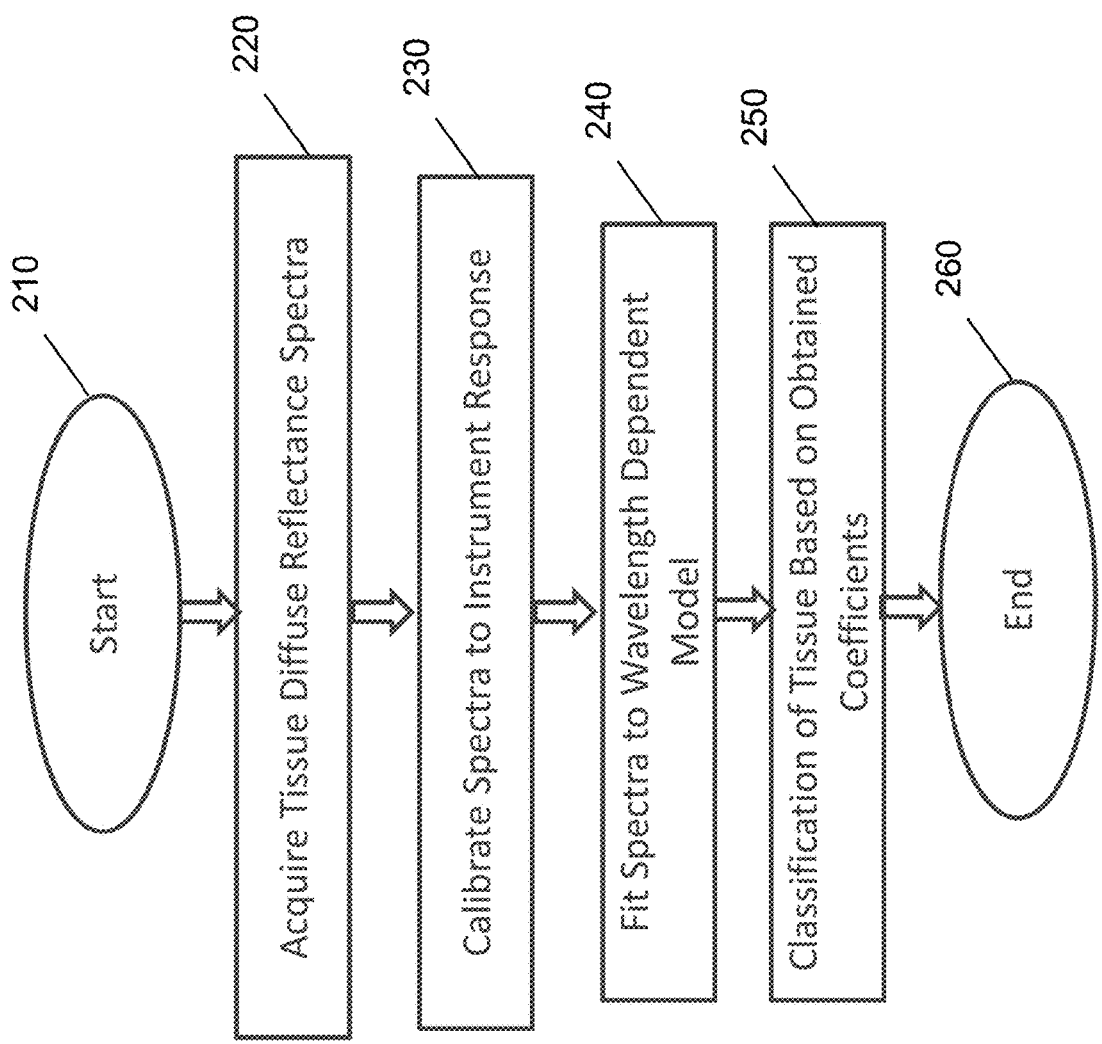
FIG. 2 is a flow diagram of an exemplary method for classifying tissue according to an exemplary embodiment of the present disclosure.

FIG. 2 shows a flow diagram of an exemplary method for tissue classification according to an exemplary embodiment of the present disclosure. For example, at procedure 210, the exemplary method can begin, or can run continuously as initiated by a computer or a user. At procedure 220, a diffuse reflectance spectra can be acquired. At procedure 230, a calibration procedure can be carried out with respect to reference standards. At procedure 240, a wavelength dependent model can be used to fit to the reflectance spectra. Subsequent properties can be derived from the model, such as absorption spectra, scattering spectra and chromophore composition. At procedure 250, using the properties/features extracted from the reflectance spectra using the wavelength dependent model, classification of the tissue can be performed. This can include identification of fat, fibrous tissue, collagen, normal myocardium, infarction, chronic ablation lesion or acute ablation lesion. At procedure 260, the exemplary procedure can be run continuously, classifying tissue until the procedure can be over or until the user stops the processing.

Figure 3:
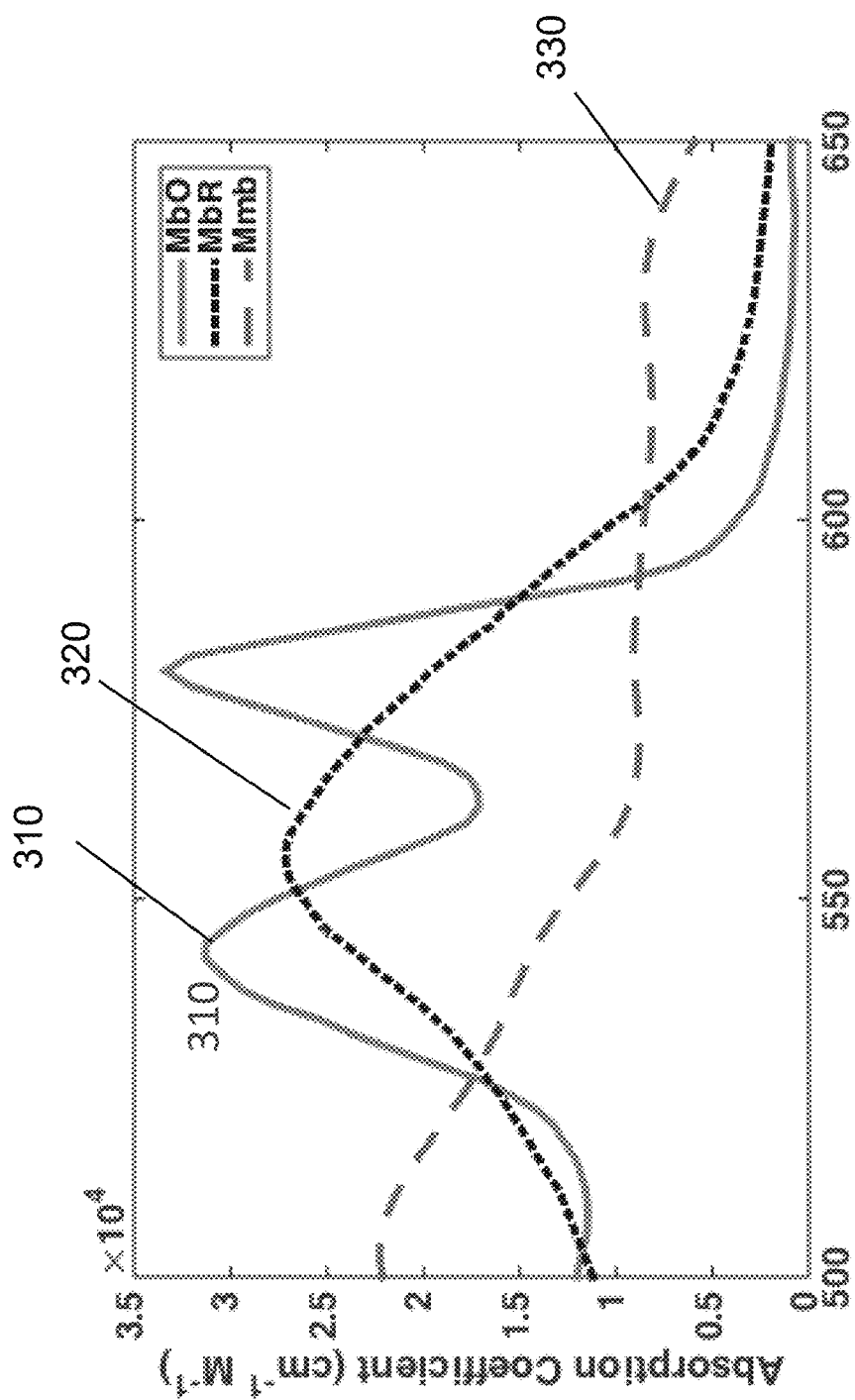
FIG. 3 is a graph illustrating extinction spectra of dominant chromophores in the visible range in the swine atria according to an exemplary embodiment of the present disclosure.
Figure 4:
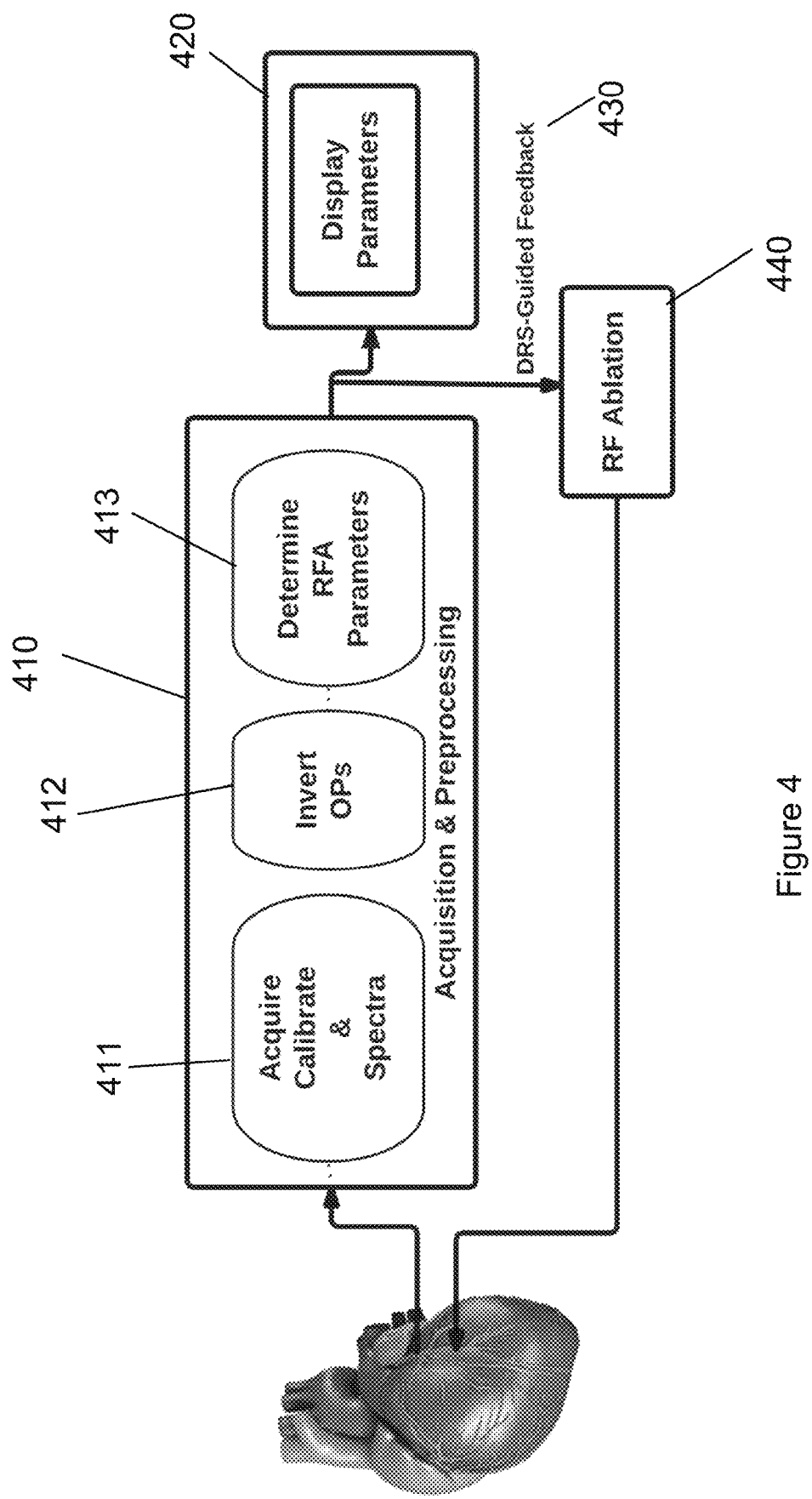
FIG. 4 is a flow diagram of an exemplary method for radiofrequency ablation according to an exemplary embodiment of the present disclosure.

As illustrates in the graph shown in FIG. 3, Extinction spectra for dominant chromophores in the visible range can be used for fitting cardiac tissue. Spectra were derived from equine heart (e.g., MbO-oxymyoglobin 310, Mb-deoxymyoglobin 320, Mmb-metmyoglobin 330). Protocol for real-time guidance of RF ablation procedures (e.g., shown in the flow diagram of FIG. 4) can include an acquisition and pre-processing of reflectance spectra procedure 410. The acquisition and pre-processing of reflectance spectra procedure can include, e.g., the acquisition of the calibration information and the spectra at procedure 411, the inversion of the Ops at procedure 412 and the determination of the RFA parameters at procedure 413. The parameters and the tissue classification can be displayed at procedure 420, with the parameters being used to guide feedback at procedure 430, including titrating ablation power, intensity, temperature, or dose. The adjustment of ablation source energy parameters can be performed at procedure 440 until the desired parameters (e.g., lesion depth) can be achieved.

Figure 5:
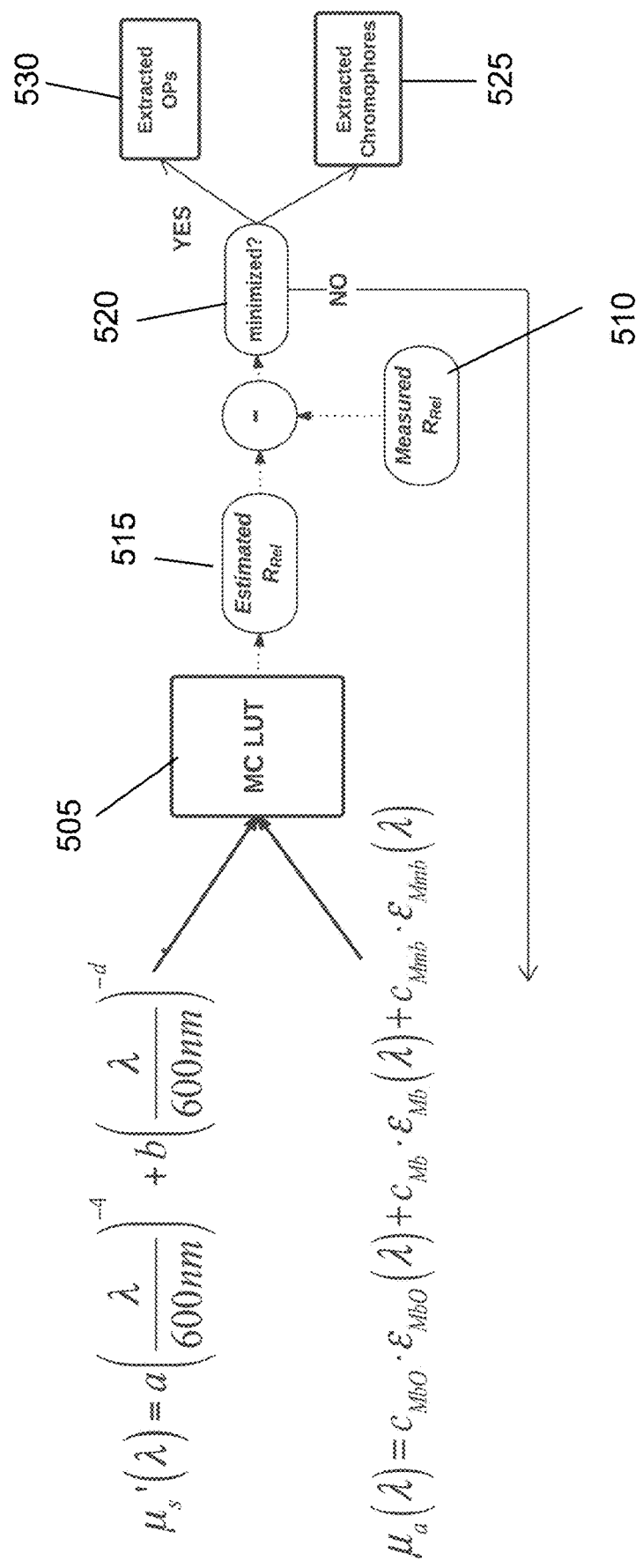
FIG. 5 is an exemplary diagram illustrating exemplary results for inverting diffuse reflectance measurements to RF parameters according to an exemplary embodiment of the present disclosure.

FIG. 5 illustrates exemplary results of inverting Diffuse Reflectance measurements to RF parameters according to an exemplary embodiment of the present disclosure. A precomputed look-up table 505 can be used as a forward model that takes in a combination of absorption and reduced scattering coefficients and outputs the diffuse reflectance for the illumination-collection geometry. For example, the absorption profile can be modeled as a weighted sum of dominant chromophores oxy-myoglobin, deoxy-myoglobin and met-myoglobin. Reduced scattering spectra can be modeled as a sum of Rayleigh and Mie scatterers. The error between the measured relative reflectance ("Rrel") 510 and the predicted (e.g., estimated) Rrel 515 can be minimized 520 or otherwise reduce in the least-squares sense by finding the optimal coefficient values within the absorption and reduced scattering expressions. The extracted chromophores 525 and optical properties 530 could then be used for tissue substrate determination and inferring lesion characteristics.

Exemplary Results

Figure 6:
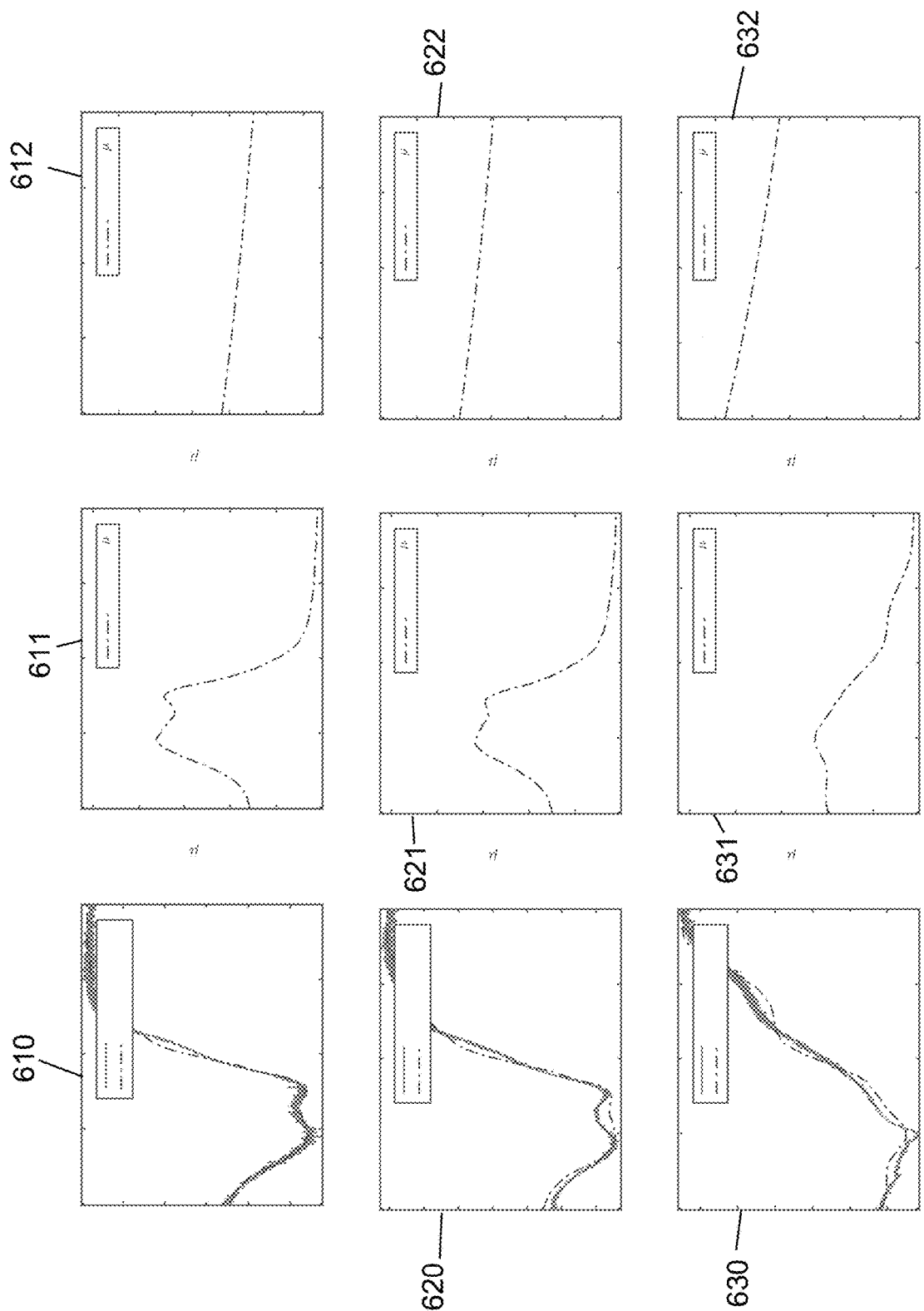
FIG. 6 is a set of graphs illustrating exemplary representative spectra and corresponding fitting results for three exemplary groups: untreated (e.g., top row), mildly treated (e.g., middle row), moderately treated (e.g., bottom row) according to an exemplary embodiment of the present disclosure.
Figure 7:
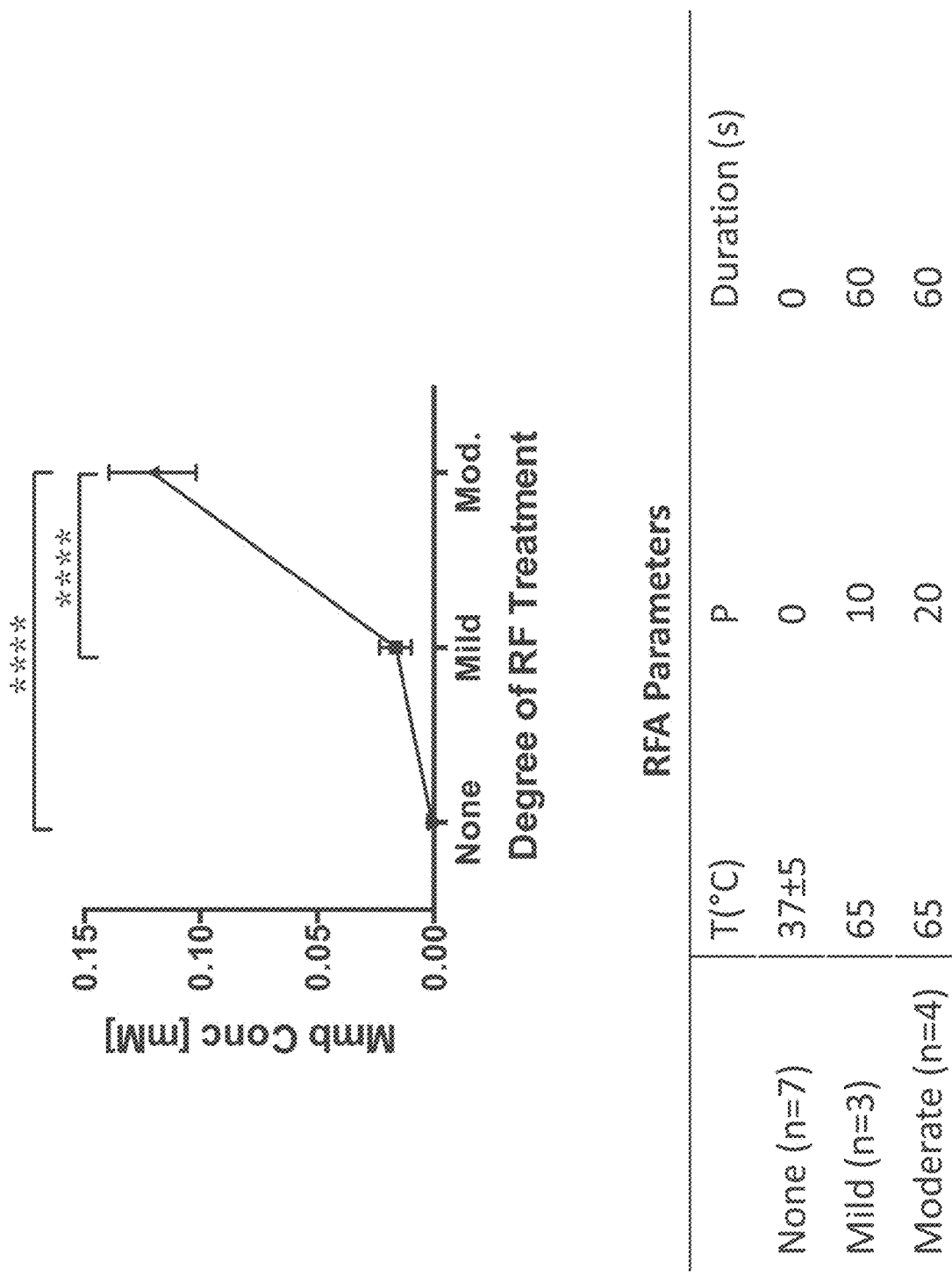
FIG. 7 is a graph illustrating exemplary statistical comparison of optically determined Mmb concentrations for varying degrees of RF treated tissue according to an exemplary embodiment of the present disclosure.

FIG. 6 shows a set of exemplary graphs of representative optical measurements for three group according to an exemplary embodiment of the present disclosure. For example, the exemplary graphs shown in FIG. 6 illustrate the effect of radiofrequency ablation on measurements in ex vivo right atrium samples (e.g., swine). For example, graphs 610, 611 and 612 show representative spectral fitting and optical property extraction for the untreated myocardium. Graphs 620, 621 and 622 and graphs 630, 631 and 632 indicate similar measurements obtained for the light treated myocardium (e.g., graphs 620, 621 and 622) and moderately treated myocardium (e.g., graphs 630, 631 and 632) moderately treated myocardium. An increase in scattering can be observed with increasing lesion depth. In addition, the spectral shape of the absorption curve changes with moderate treatment, compared with untreated and lightly treated. FIG. 7 shows a chart illustrating that the comparisons across the groups revealed significantly greater Mmb concentrations (e.g., $p<0.0001$) in the moderately treated group as compared to the other two groups (e.g., the effect of RF treatment on optically determined tissue met-myoglobin concentration in the swine right atrium). Additionally, an increasing trend in Mmb concentration was observed for increased tissue treatment (e.g., see graph shown in FIG. 7).

Figure 8:
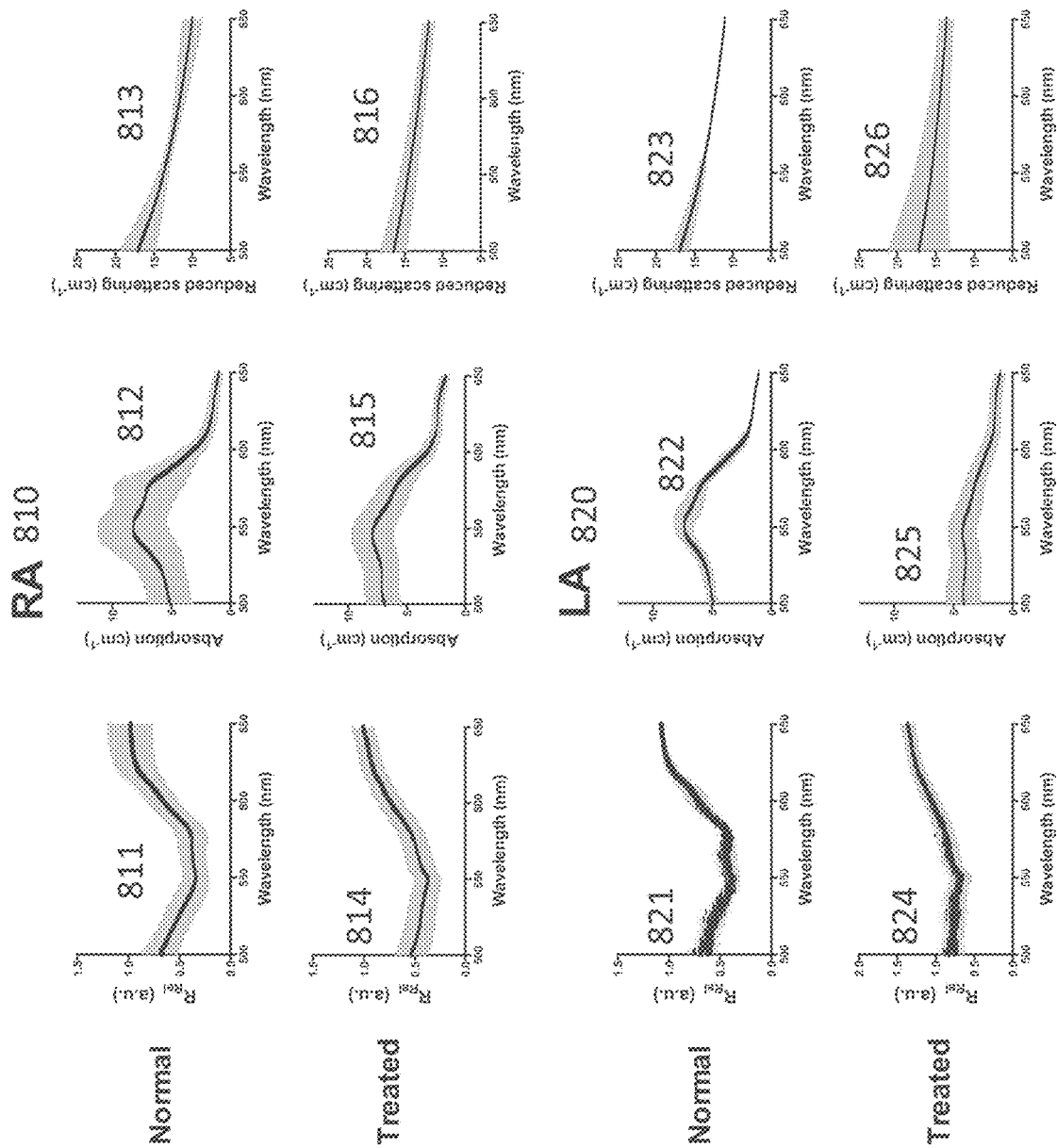
FIG. 8 is a set of graphs illustrating reflectance spectra, extracted absorption and scattering spectra from visible light spectroscopy according to an exemplary embodiment of the present disclosure.

FIG. 8 shows a set of exemplary graphs illustrating examples of reflectance spectra (e.g., graphs 811, 814, 821 and 824), extracted absorption (e.g., graphs 812, 815, 822 and 825) and scattering spectra (e.g., graphs 813, 816, 823, 826) from visible light spectroscopy. Mean and standard deviations for optical measurements in right atrium (e.g., RA 810) and left atrium (e.g., LA 820) from four swine hearts, for normal untreated areas and areas treated with radiofrequency ablation. The change in absorption spectra morphology for treated tissue (e.g., graphs 815 and 825) suggests a difference in biochemical composition compared to untreated tissue.

Figure 9:
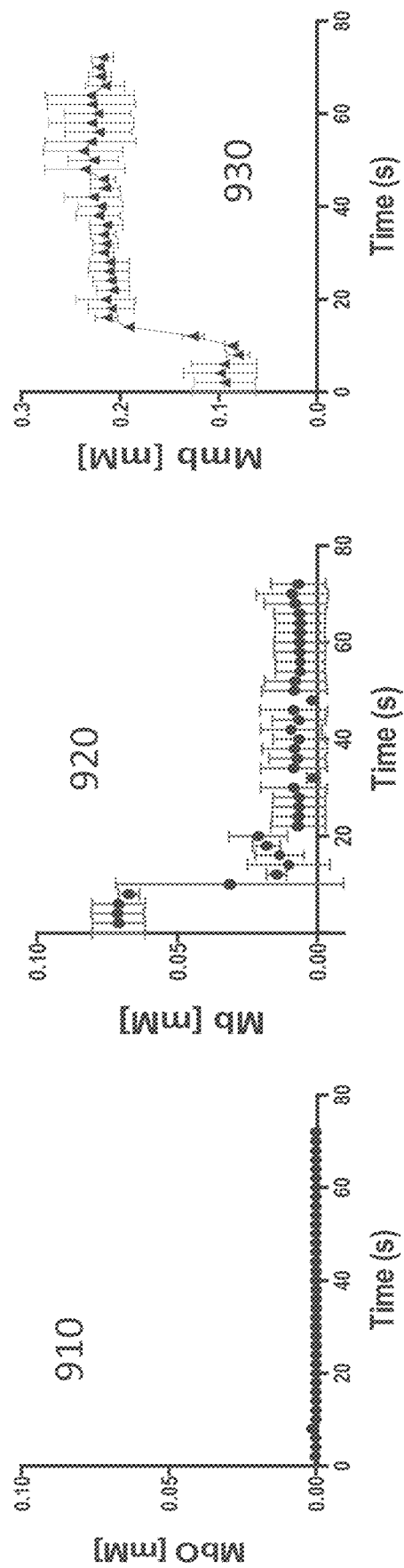
FIG. 9 is a set of graphs illustrating examples of real-time monitoring of RF ablation according to an exemplary embodiment of the present disclosure.

FIG. 9 illustrates a set of graphs illustrating examples of real-time monitoring of RF ablation in human atrial tissue with visible light spectroscopy. Ablation started at $t=8$ s. For example, graph 920 shows a decrease in deoxy-myoglobin can be observed from the onset of RF ablation. Graph 930 shows a corresponding increase in met-myoglobin content can be observed as RF energy can be continually applied to the tissue. Graph 910 shows concentrations of oxy-myoglobin were negligible and did not change significantly during ablation.

Figure 10:
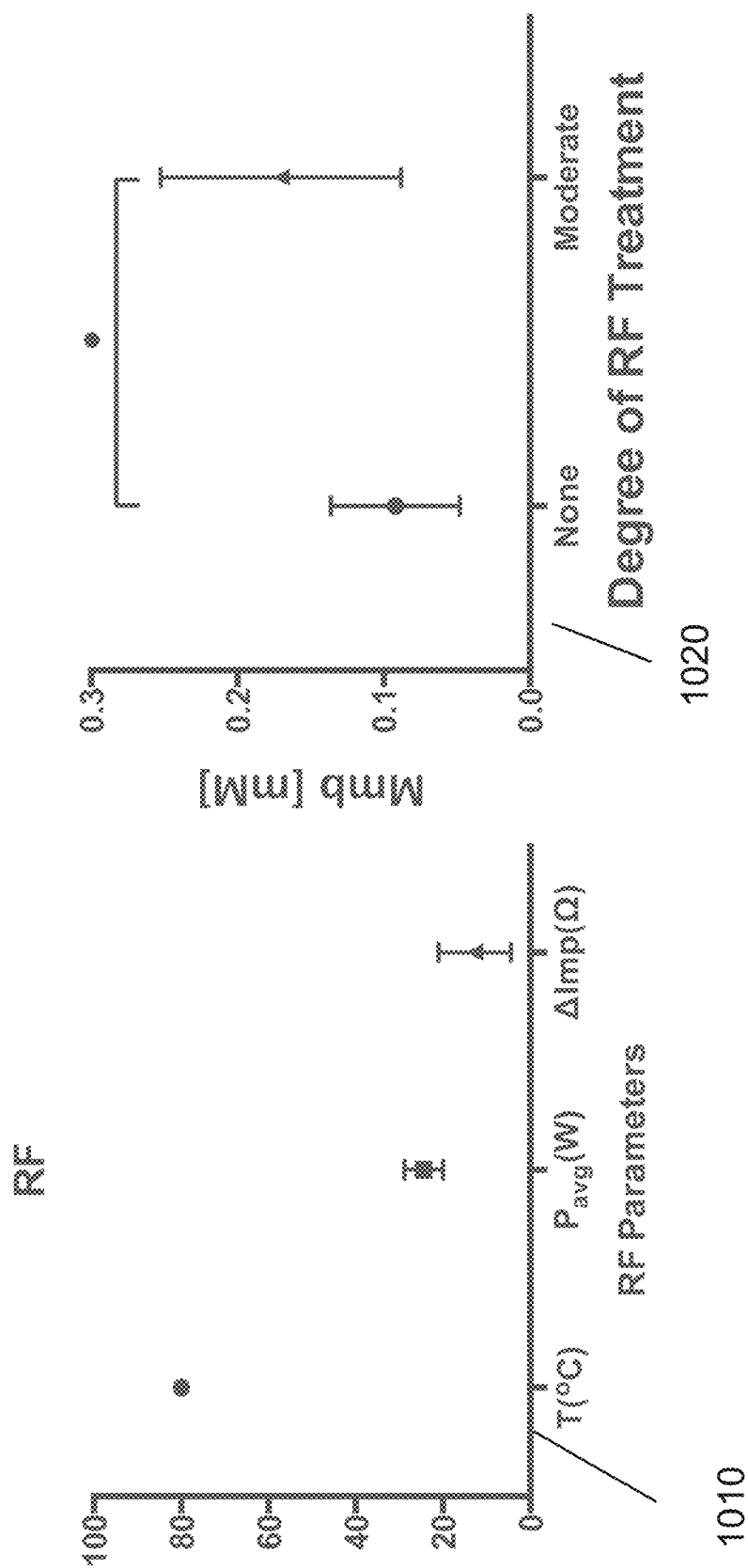
FIG. 10 is a set of graphs illustrating the effect of RF treatment on optically determined met-myoglobin concentration according to an exemplary embodiment of the present disclosure.

FIG. 10 shows a set of graphs illustrating examples of the affect or RF treatment on optically determined met-myoglobin concentration in an ex-vivo human right atrium. For example, graph 1010 shows the standard parameters measured from the ablation catheter, temperature ("T"), Average Power ("Pavg") and change in impedance (e.g., $\Delta \text{imp}(\Omega)$). Met-myoglobin concentration significantly increased between untreated and moderately treated lesions, (e.g., $P<0.05$).

Figure 11:
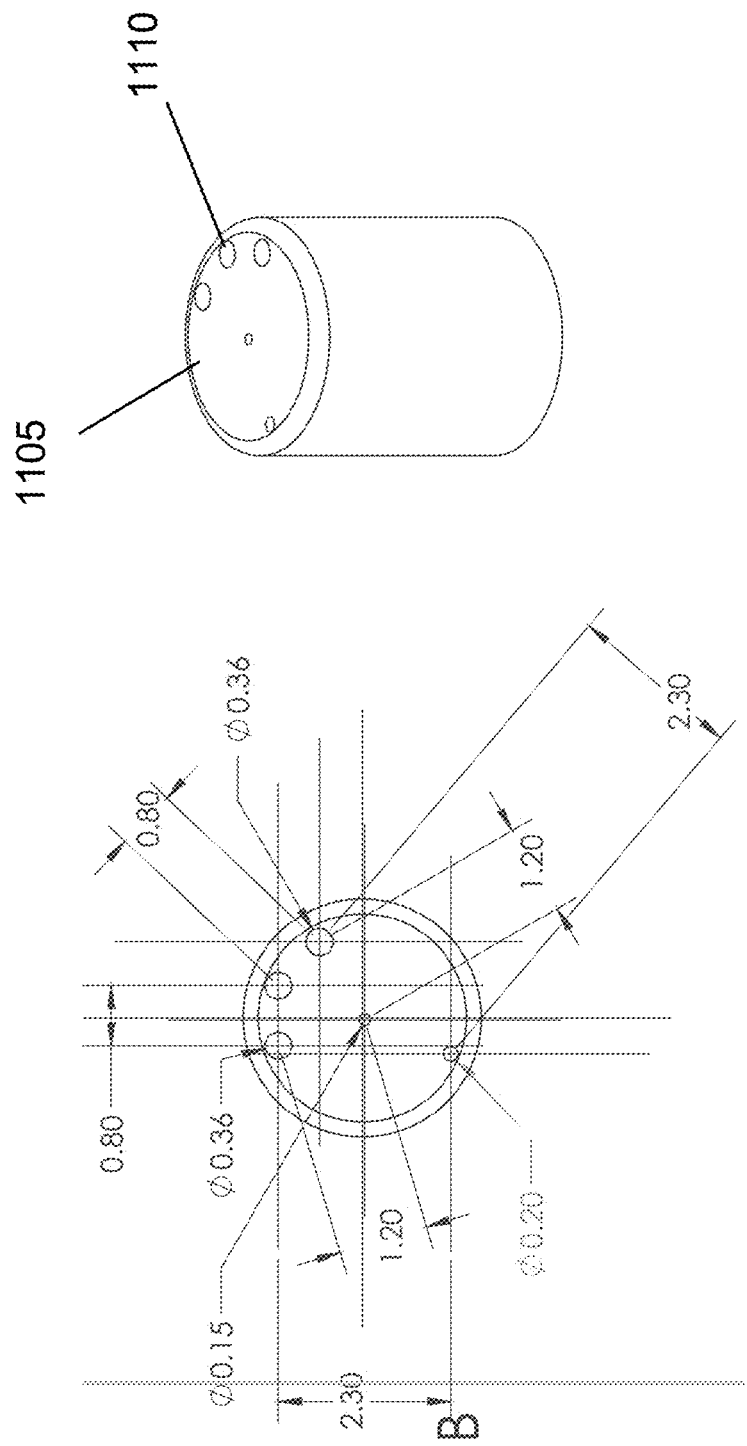
FIG. 11 is a diagram of an exemplary catheter according to an exemplary embodiment of the present disclosure.

FIG. 11 shows a diagram of an exemplary design for a catheter tip 1105 containing slots 1110 for multiple optical fibers according to an exemplary embodiment of the present disclosure. Sensitivities to absorption and scattering can vary with source detector separation. Thus, full-spectrum reflectance data can be leveraged by simultaneously acquiring data from multiple distances away from the source. Furthermore, multiple source-detector pairs can be used to determine relative contact angle of catheter to tissue surface. Collection fibers can be used for visible light spectroscopy, near infrared spectroscopy, autofluorescence or optical coherence tomography.

Figure 12:
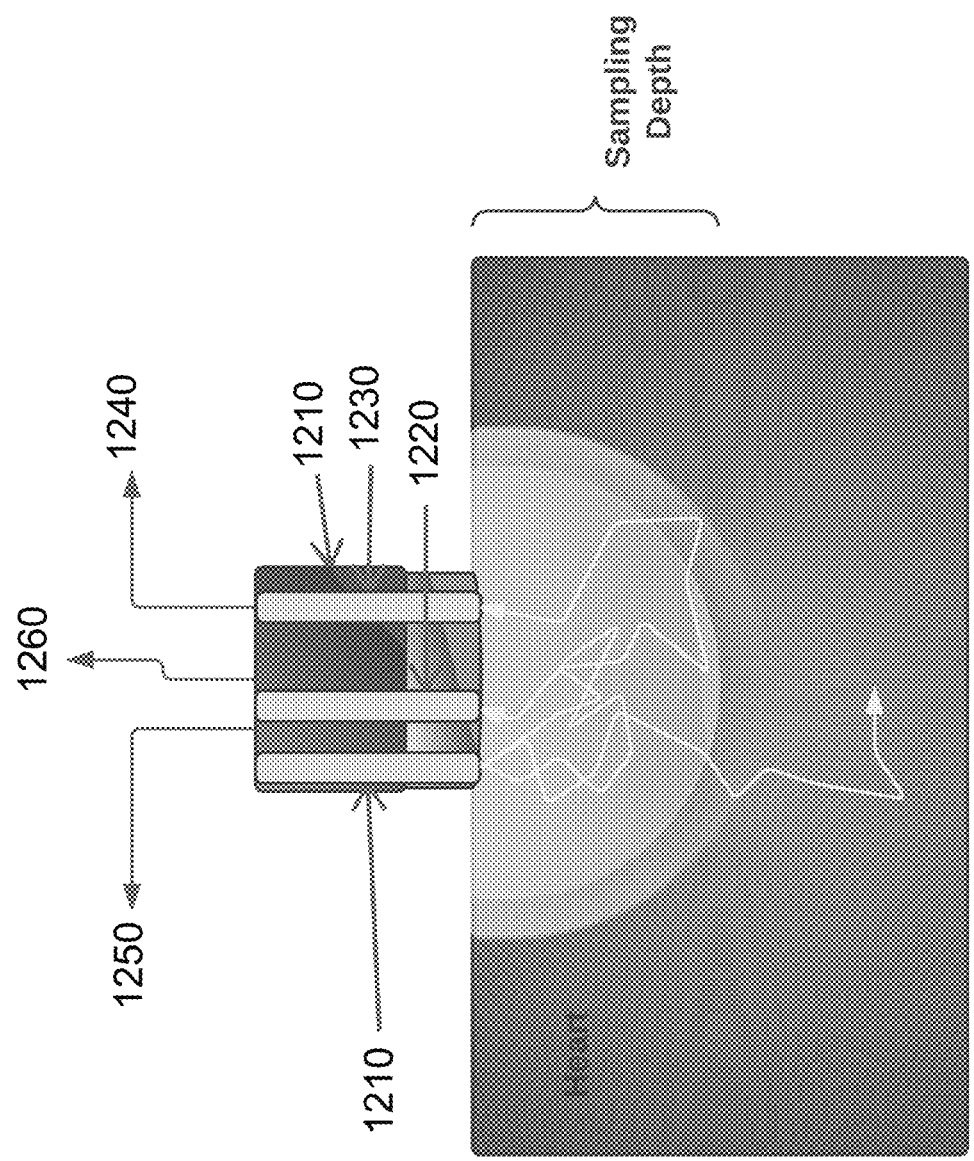
FIG. 12 is a diagram illustrating an exemplary catheter ablating and illuminating tissue according to an exemplary embodiment of the present disclosure.

As shown in the diagram of FIG. 12, a fiber-integrated catheter 1200 can be used to combine visible and NIR spectral measurements. The target tissue sample can be illuminated with a source energy 1250 with an illumination fiber 1210. The close source-detector fiber separations ("SDFS") can probe light that does not travel very deep into the tissue (e.g., using close collection fiber 1220). The wide SDFS 1230 can measure light that can probe deeper into the tissue and can be more sensitive tissue absorption. Because the absorption of dominant metalloproteins in cardiac tissue can be orders of magnitude higher in the visible region than the NIR, close SDFS can be used to measure the apparent large absorption in the visible region while using wide SDFS collection to appreciate the more modest absorption changes in the NIR regime. Both light collected through close collection fiber 1220 and wide SDFS 1230 can return to the spectrometer 1240 for detection. Reflectance spectra from both detection fibers can enable tissue characterization, chromophore composition analysis, and contact angle determination during the process of the ablation procedure for pre-procedural substrate classification and real time evaluation during the application of ablation energy 1260.

FIG. 13 shows a flow diagram of an exemplary method for lesion depth monitoring according to an exemplary embodiment of the present disclosure. Visible light spectroscopy can aid in verifying that the lesion produced in permanent and NIR spectroscopy can verify lesion depth. For example, at procedure 1310 the exemplary method can be run continuously or initiated by user. At procedure 1320, diffuse reflectance spectra can be acquired. At procedure 1330, ablation treatment can begin by turning on source energy, such as radiofrequency, laser, ultrasound or cryo. At procedure 1340, real-time spectra can be acquired during the ablation treatment time course. A wavelength dependent model can be used to fit to the reflectance spectra. Subsequent properties can be derived from the model, such as absorption spectra, scattering spectra and chromophore composition. At procedure 1350, using the properties/features extracted from the reflectance spectra using the wavelength dependent model, classification of the tissue can be performed. Status of the ablation lesion formation can be provided, included proxies for ablation lesion depth, whether permanent injury has occurred, whether a steam pop has occurred, and whether contact is being maintained with the tissue. At procedure 1360, the exemplary method can run continuously, classifying tissue until the procedure can be over when the target lesion depth has been achieved.

FIG. 14 shows an exemplary diagram of the exemplary catheter according to an exemplary embodiment of the present disclosure. For example, as shown in the diagram of FIG. 14, the exemplary catheter 1400 can be used for optical fiber-integrated radiofrequency ablation. The exemplary catheter 1400 can include one or more electrode tip houses 1410 illumination and one or more sets of collection optodes 1420, as well as openings 1430 for a saline irrigation/ flushing. Both fiber can be are distributed along the circumference and face of the metal tip of catheter 1400. High speed 1440 fiber optic switches can be used to alternate between source and detector positions. The contact orientation with the tissue surface can be estimated using catheter 1400 by multi-detector measurements for all possible given source positions. The tissue characteristics can then be determined by fitting an exemplary light transport model to the geometry spanned by the subset of optodes that are in contact.

Further, the illumination location can be alternated while stimulation of the tip side can be distributed throughout the arranged to position, which can be alternatingly scanned throughout any given sets of holes. The exemplary catheter 1400 can be used for obtaining measurements from myocardial tissues as well as the zone of resistive heating during ablation. Optical fibers can be in a sheathe where an inner channel can accept a commercially available RFA catheter. Two sets of fibers can typically be employed (e.g., illumination and collection). Broadband light can be delivered onto the heart via one or more of the illumination fiber. The tissue can be diffusely backscattered light, which can then be recovered by the collection fibers, which can be placed at some distance away from the illumination point. Collected photons samples of the myocardium can contain information on physiological makeup and ultrastructure of the traverse path.

Figure 15A:
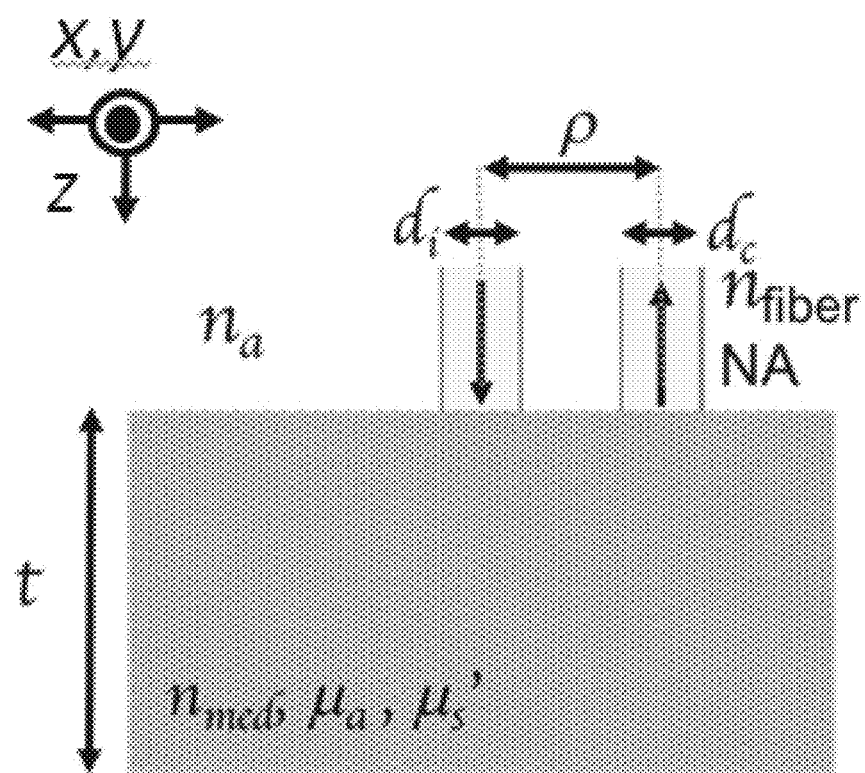
FIG. 15A is a diagram illustrating a source-detector separation according to an exemplary embodiment of the present disclosure.
Figure 15B:
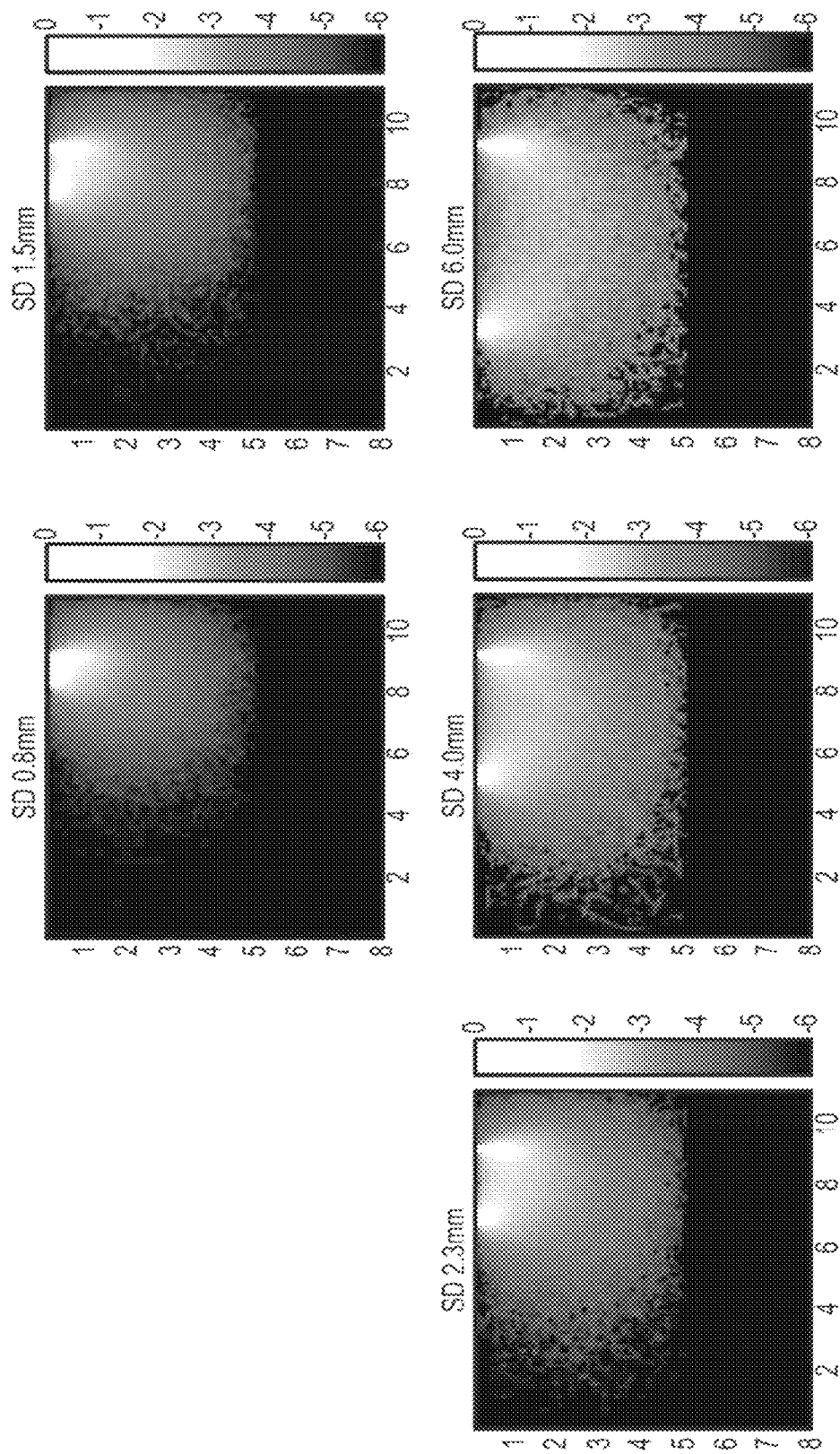
FIG. 15B is a set of maps illustrating the source-detector separation on measured signals according to an exemplary embodiment of the present disclosure.

FIG. 15A shows a diagram illustrating source-detector separation and FIG. 15B shows a set of charts illustrating the impact of source-detector separation on measured signals according to an exemplary embodiment of the present disclosure. Monte Carlo simulations were performed for various illumination-collection geometries for a 5 mm thick slab with a fixed optical properties. (See, e.g., FIG. 15B). The Jacobian shows a greater depth of tissue interrogated with increased fiber separations.

Figure 16:
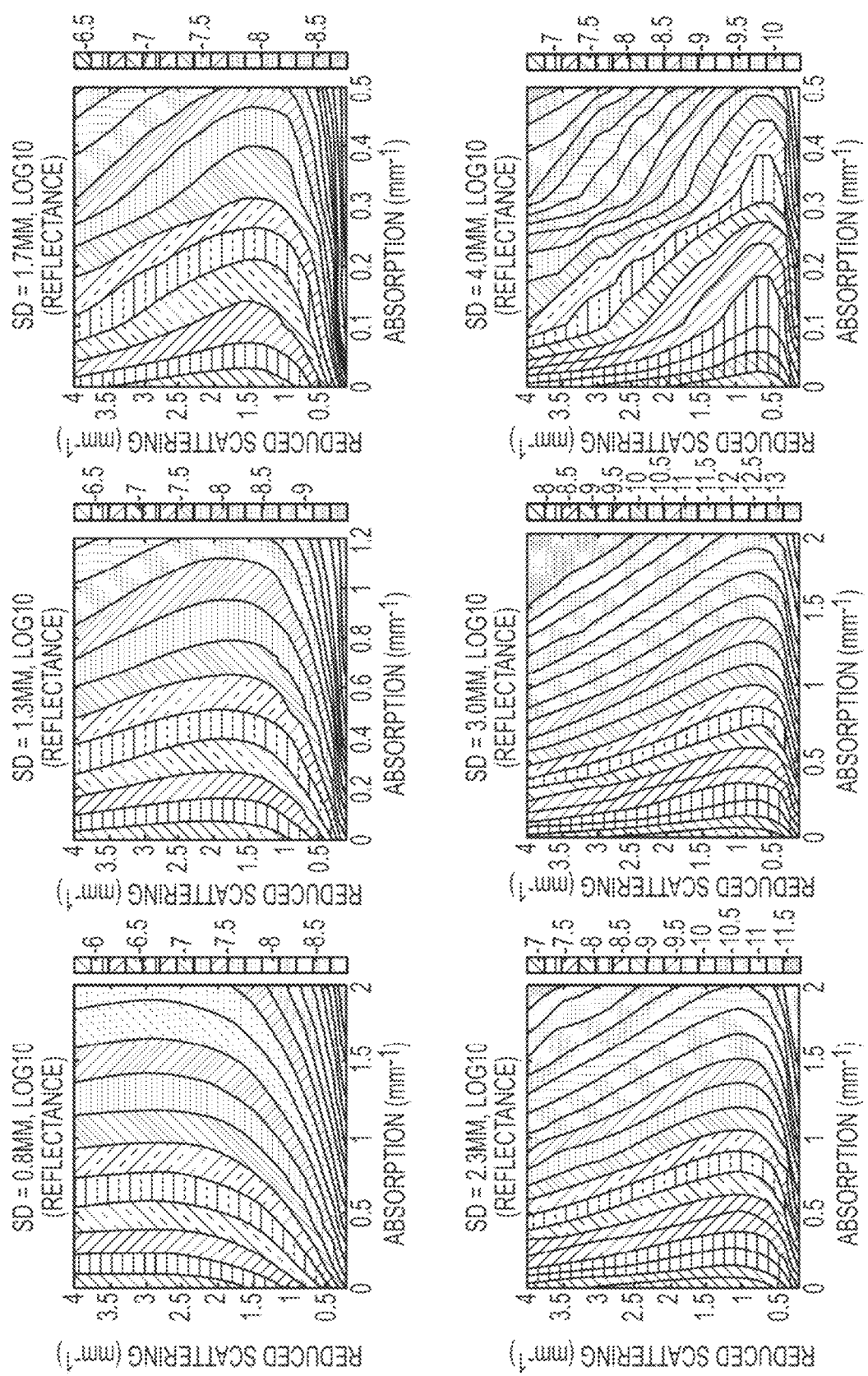
FIG. 16 is a set of maps illustrating the impact of tissue absorption and scattering parameters on the measured reflectance for various source-detector separations according to an exemplary embodiment of the present disclosure.

FIG. 16 shows a set of exemplary maps illustrating the impact of tissue absorption and scattering parameters on measured reflectance for various source-detector separations according to an exemplary embodiment of the present disclosure. For example, as shown in FIG. 16, for smaller fiber separations, increases in reduced scattering generally results in increased signal intensity. For larger separations, a momentary increase is shows, followed by a gradually decrease in the signal. The increased separation alters the scattering value at which this inflection point occurs, as well as the rate of decrease due to scattering. Additionally, larger source detector separations experience greater sensitivities to absorption due to the longer path length traveled by collected photons.

Figure 17:
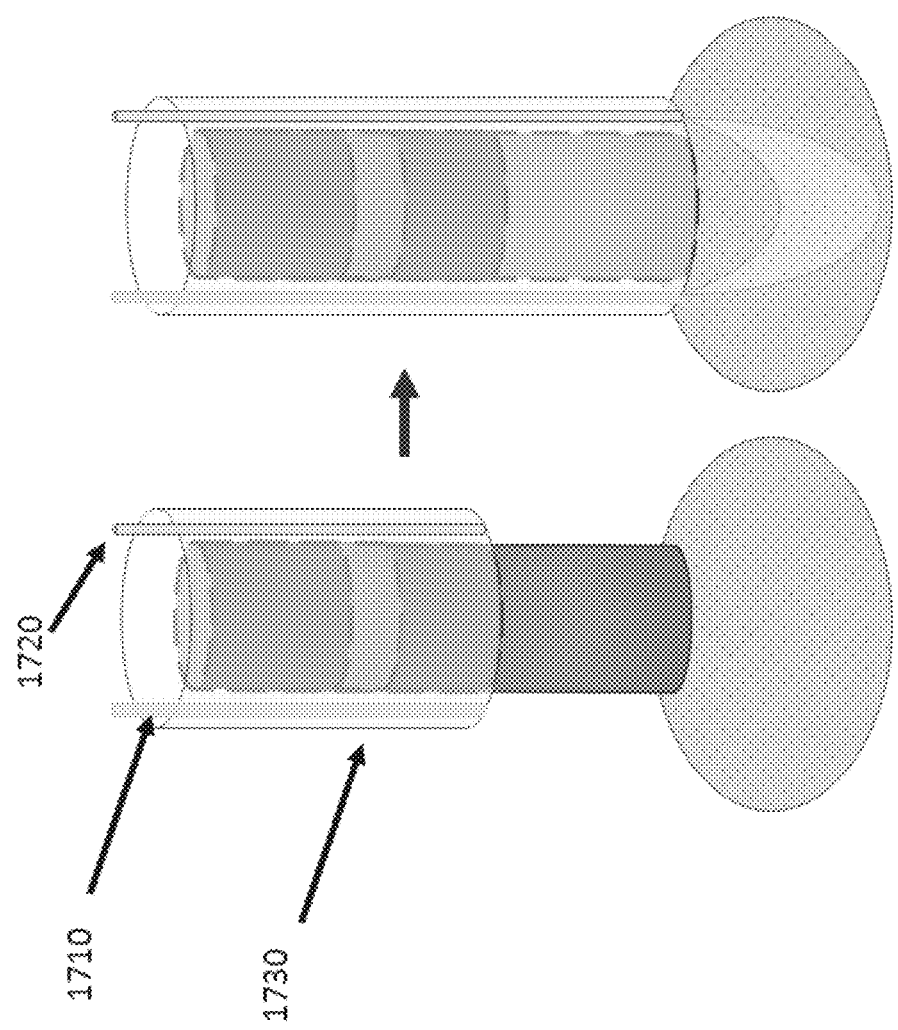
FIG. 17 is a set of diagrams of exemplary catheter sheaths according to an exemplary embodiment of the present disclosure.

FIG. 17 shows a set of diagrams of exemplary catheter sheaths according to an exemplary embodiment of the present disclosure. The exemplary sheaths can be optically-integrated, and can utilize the sheathes for tissue characterization during the exemplary RF procedures. Illumination fibers 1710 and collection fibers 1720 can be placed along the sheathe wall 1730. An insertion through the inner channel can facilitate supplemental optical measurements to be taken using any commercial catheter.

Figure 18:
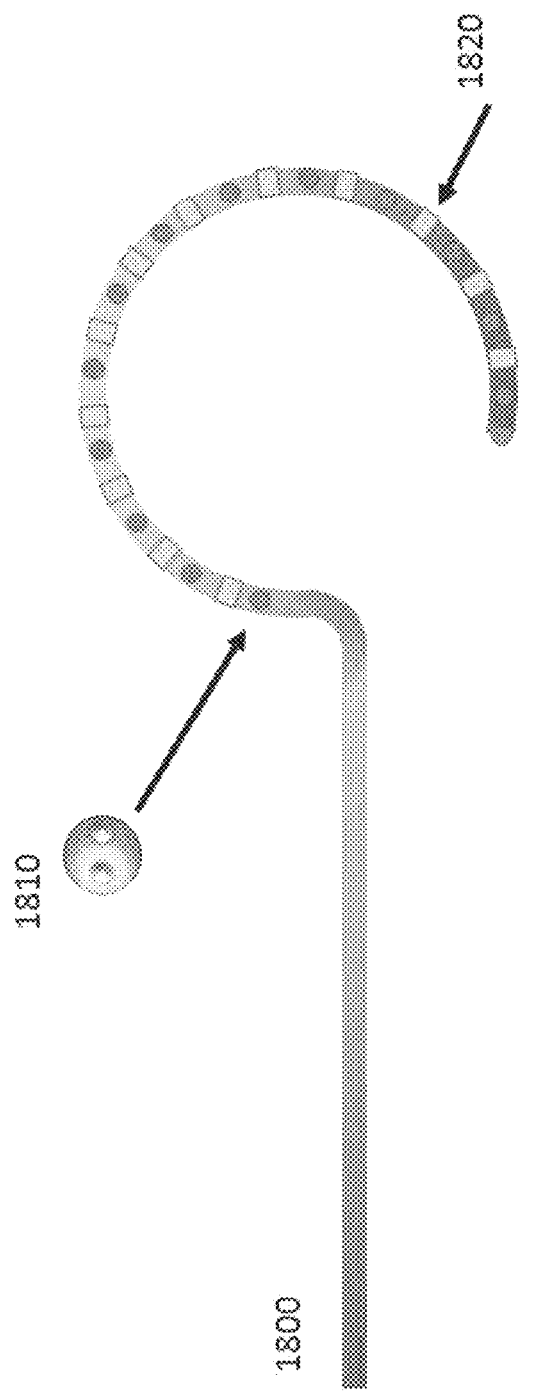
FIG. 18 is a diagram of an optically-integrated mapping catheter according to an exemplary embodiment of the present disclosure.

FIG. 18 shows a diagram of an optically-integrated mapping catheter 1800 according to an exemplary embodiment of the present disclosure. For example, as shown in FIG. 18, illumination-collection pairs 1810 can be placed alongside electrodes 1820, to facilitate simultaneous electrical measurements along with local optical tissue characterization. Optical parameters point clouds, or surface maps, can be generated using positional information provided by navigational systems and can provide information on lesion gaps and lesion inadequacy.

Figure 19:
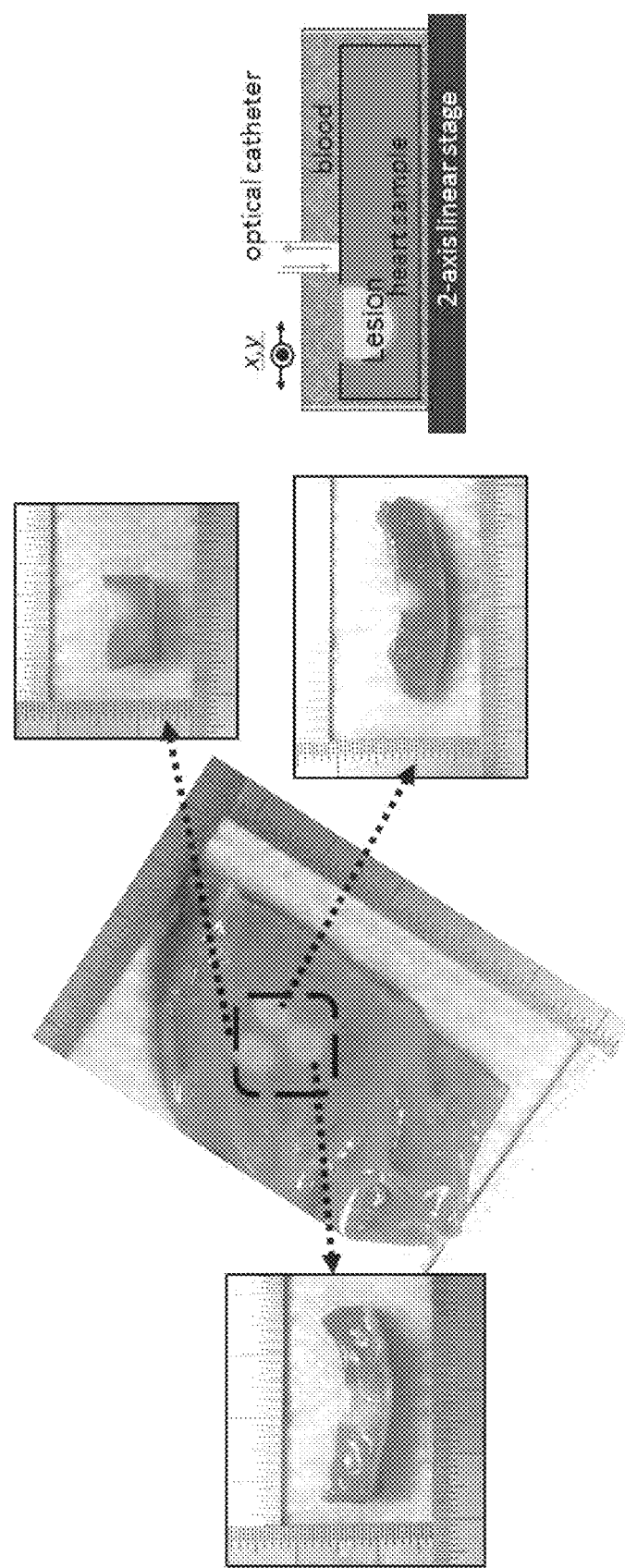
FIG. 19 is a set of images illustrating ex-vivo lesion mapping setup according to an exemplary embodiment of the present disclosure.

FIG. 19 shows a set of images illustrating ex-vivo lesion mapping setup according to an exemplary embodiment of the present disclosure. A swine right ventricular wedge was ablated with various lesion sizes. The sample was submerged in blood, and optical measurements were made across the surface. The catheter was translated using a two-axis linear stage, which provided spatial coordinates for optical parameters maps. Lesion depth was determined using an approximately 1% tetrazolium chloride staining post-optical measurements.

Figure 20:
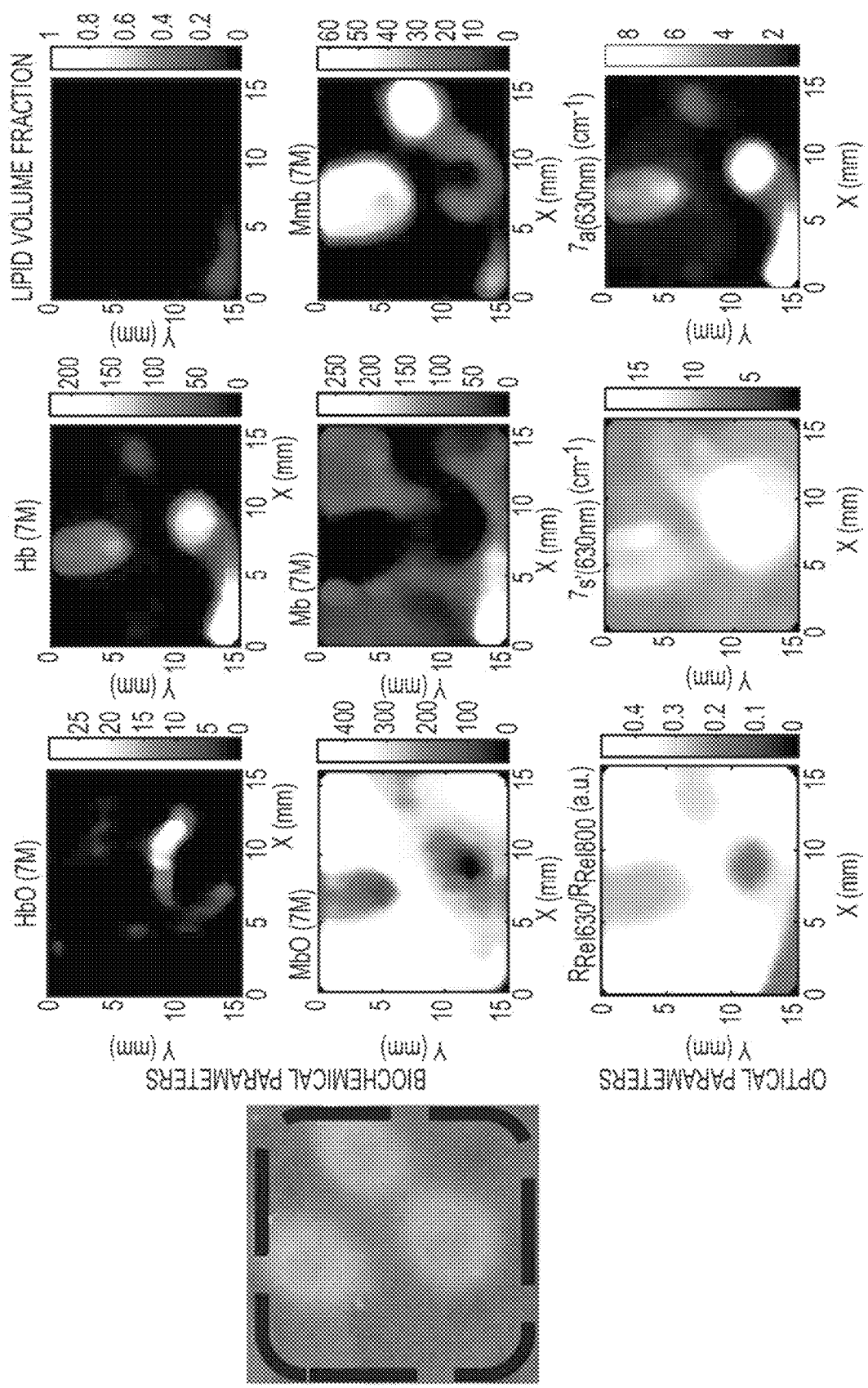
FIG. 20 is a set of exemplary optical parameter maps of the swine right ventricular lesion set produced using the exemplary catheter according to an exemplary embodiment of the present disclosure.

FIG. 20 shows a set of optical parameter maps of the swine right ventricular lesion set produced using the exemplary catheter according to an exemplary embodiment of the present disclosure. For example, the Metmyoglobin maps shown in FIG. 20 illustrate particular sensitivity to treated sites in biochemical maps. Non-specific signals can be a result of cross-talk effects due to the high absorption in blood pools where the catheter may not be in full contact. Optical parameters show strong concordance with the extent of treatment. Additionally, the scattering maps are relatively insensitive to blood pooling sites.

Figure 21A:
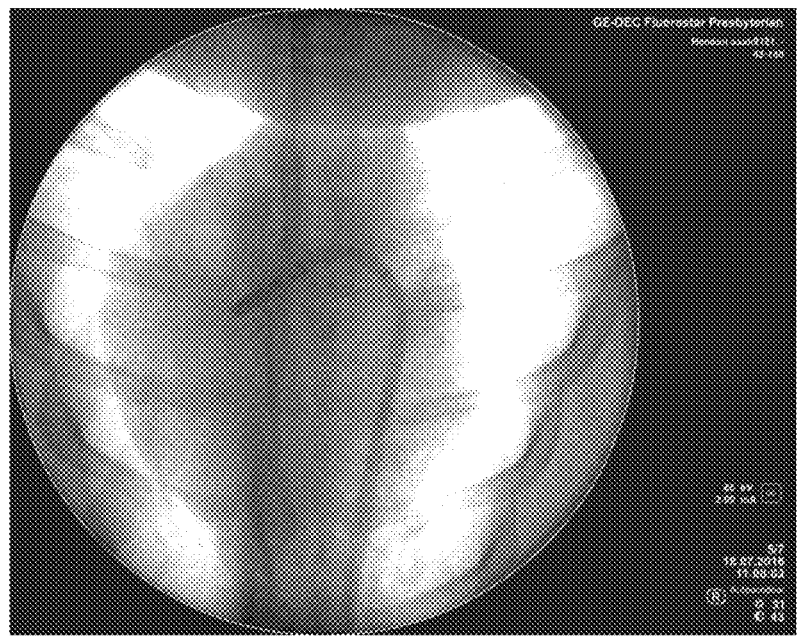
FIG. 21A is an exemplary fluoroscopy image produced using the exemplary catheter according to an exemplary embodiment of the present disclosure.
Figure 21B:
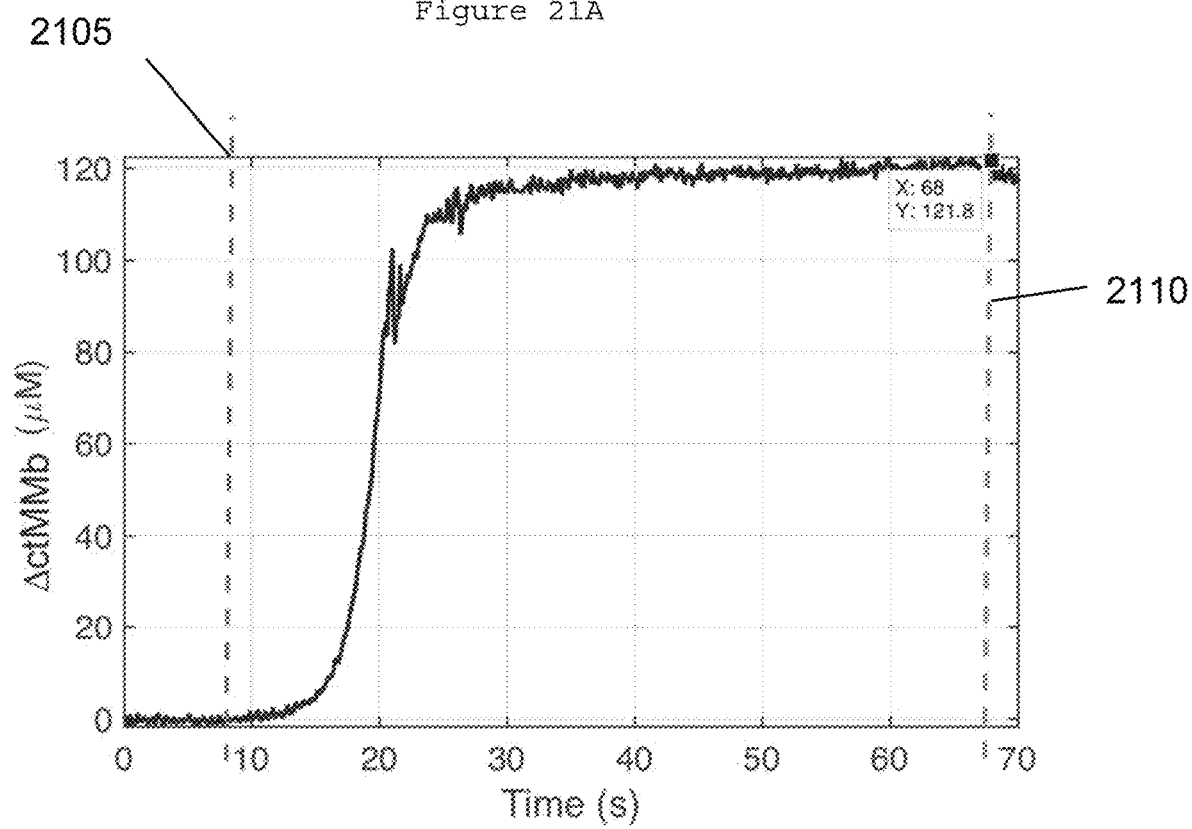
FIG. 21B is an exemplary graph illustrating extracted metmyoglobin dynamics during a 60 second cardiac ablation according to an exemplary embodiment of the present disclosure.
Figure 21C:
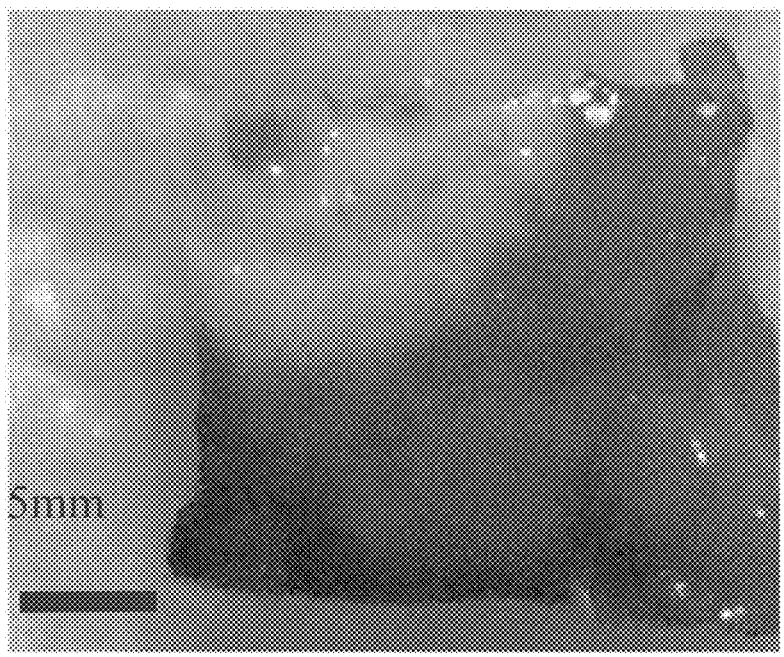
FIG. 21C is an exemplary image of a resulting lesion after tetrazolium chloride staining according to an exemplary embodiment of the present disclosure.

FIG. 21A shows an exemplary fluoroscopy image of the exemplary catheter being steered within the heart produced using the exemplary catheter according to an exemplary embodiment of the present disclosure. FIG. 21B shows an exemplary graph illustrating extracted metmyoglobin dynamics during a 60 second cardiac ablation according to an exemplary embodiment of the present disclosure. RF initiation is marked by the dashed line 2105 while RF termination is marked by the dashed line 2110. FIG. 21C shows an exemplary image of a resulting lesion after tetrazolium chloride staining according to an exemplary embodiment of the present disclosure.

Figure 22A:
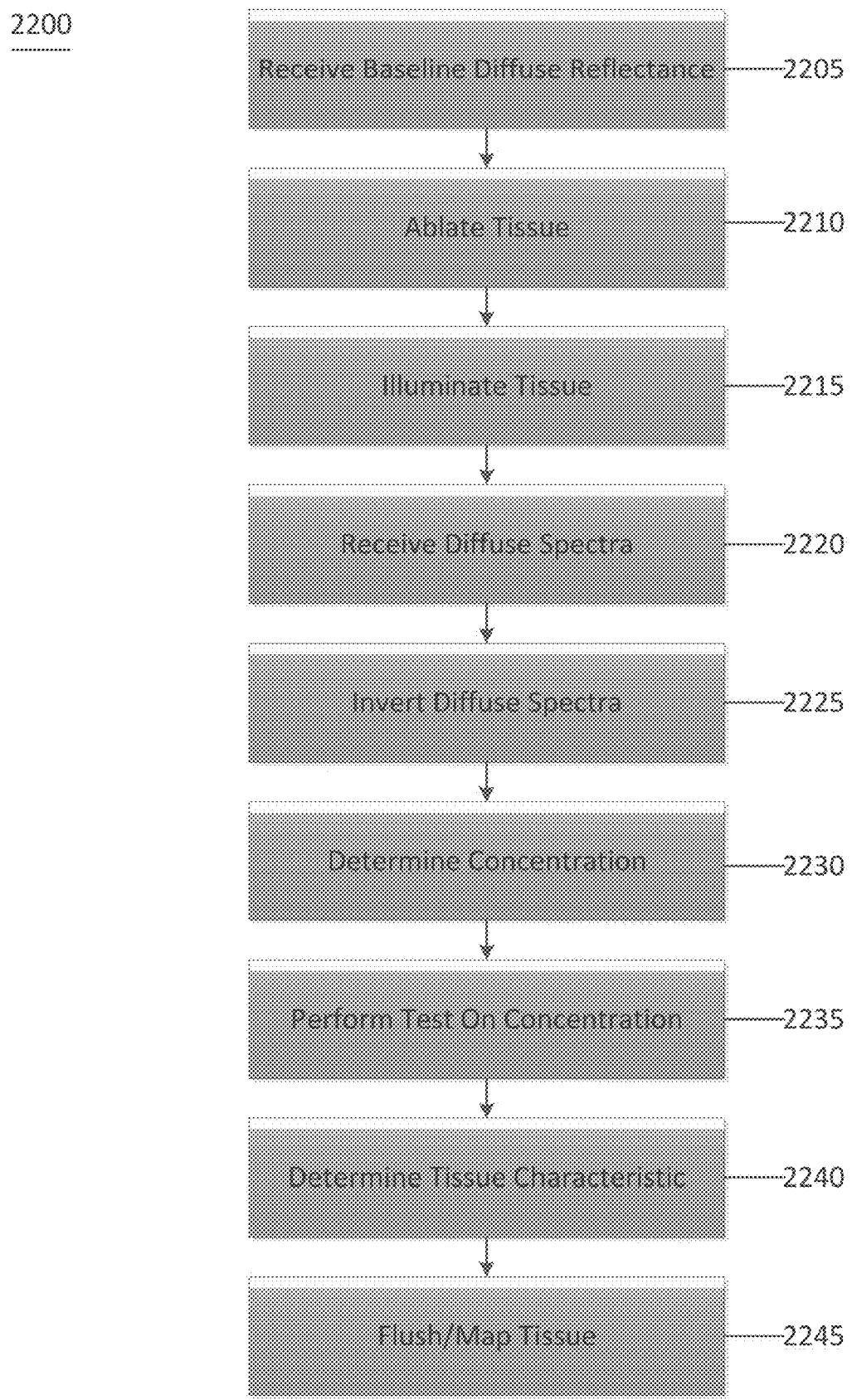
FIG. 22A is a flow diagram of an exemplary method for determining a characteristic of a tissue according to an exemplary embodiment of the present disclosure.

FIG. 22A shows a flow diagram of an exemplary method 2200 for determining a characteristic of a tissue according to an exemplary embodiment of the present disclosure. For example, at procedure 2205, a baseline diffuse reflectance spectra of the tissue can be received. At procedure 2210, the tissue can be ablated, and at procedure 2215, the tissue can be illuminated. At procedure 2220, diffuse reflectance spectra can be received based on the illumination from procedure 2215, which can be inverted at procedure 2225. At procedure 2230, a concentration (e.g., oxy-myoglobin, a deoxy-myoglobin and a met-myoglobin) can be determines based on the inverted diffuse reflectance spectra. At procedure 2235, a test (e.g., an analysis of variance test or Tukey's multiple comparison test) can be performed on the met-myoglobin. At procedure 2240, a characteristic of the tissue can be determined. Additionally, at procedure 2245, the tissue can be flushed, or the tissue can be mapped (e.g., using voltage mapping).

Figure 22B:
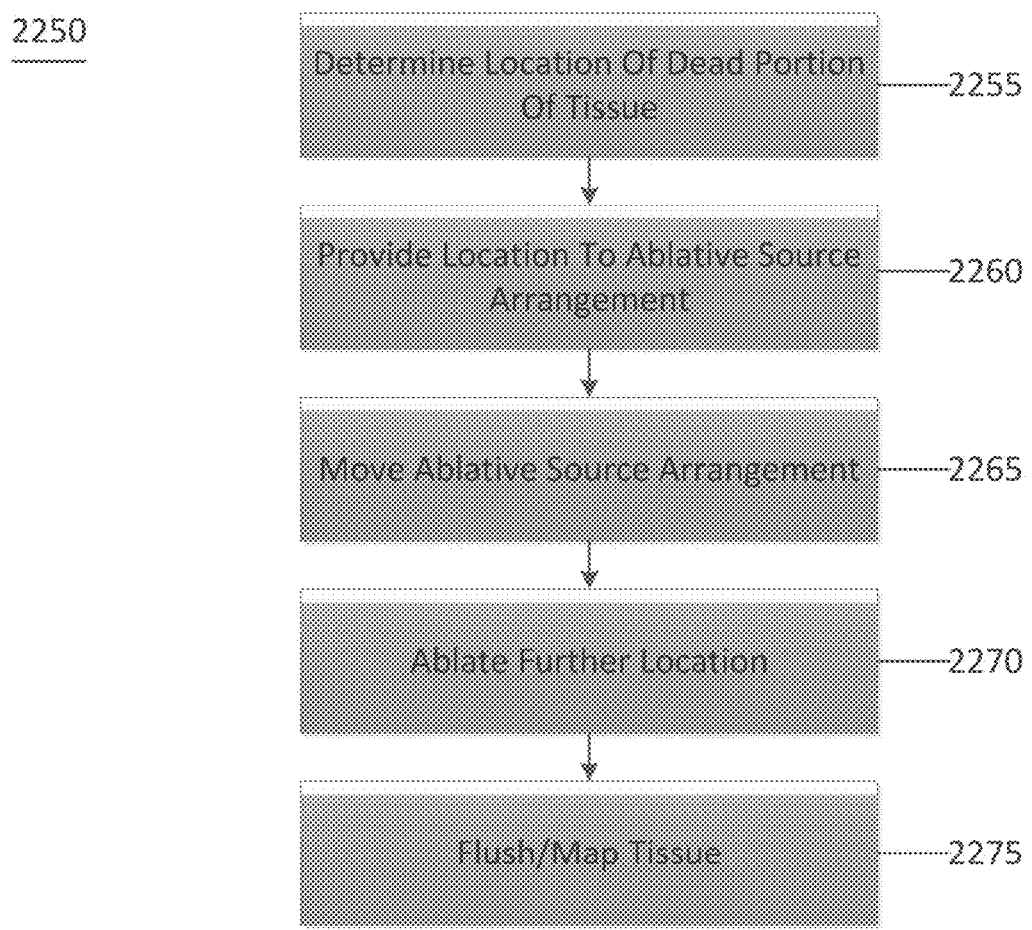
FIG. 22B is a flow diagram of an exemplary method for ablating a tissue according to an exemplary embodiment of the present disclosure.

FIG. 22B shows a flow diagram of an exemplary method 2250 for ablating a tissue according to an exemplary embodiment of the present disclosure. For exemplary, at procedure 2255, a location of a dead portion of a tissue can be determined. This location can be provided to an ablative source arrangement at procedure 2260. At procedure 2265, the ablative source arrangement can be moved to a further location, and the further location can be ablated at procedure 2270. Additionally, at procedure 2275, the tissue can be flushed, or the tissue can be mapped (e.g., using voltage mapping).

DISCUSSION

Exemplary results indicate that met-myoglobin quantification can serve as an important marker for estimating increased tissue treatment. Furthermore, these measurements can be facilitated by real-time optical measurements made at the RFA catheter tip.

The following are provided as exemplary aspects of the present disclosure.

Aspect 1: A method for determining at least one characteristic of at least one tissue, comprising: ablating the at least one tissue; illuminating the at least one tissue during the ablation procedure; and using a computer hardware arrangement, continuously determining the at least one characteristic based on the ablation and illumination procedures.

Aspect 2: The method of aspect 1, further comprising ablating the at least one tissue using radiofrequency ablation.

Aspect 3: The method of aspect 1, wherein the illumination procedure is performed with a radiation in a visible spectrum.

Aspect 4: The method of aspect 1, further comprising receiving diffuse reflectance spectra based on the illumination procedure, wherein the at least one characteristic is determined based on the received diffuse reflectance spectra.

Aspect 5: The method of aspect 4, further comprising inverting the diffuse reflectance spectra using an inverse Monte Carlo procedure.

Aspect 6: The method of aspect 5, further comprising determining a concentration of at least one of (i) an oxy-myoglobin, (ii) a deoxy-myoglobin or (iii) a met-myoglobin based on the inverted diffuse reflectance spectra.

Aspect 7: The method of aspect 5, further comprising: determining a concentration of a met-myoglobin based on the inverted diffuse reflectance spectra; and performing at least one of (i) an analysis of variance test or (ii) a Tukey's multiple comparison test on the met-myoglobin concentration.

Aspect 8: The method of aspect 5, further comprising fitting the inverted diffuse reflectance spectra to a wavelength dependent model.

Aspect 9: The method of aspect 8, further comprising receiving a plurality of coefficients based on results of the fitting step, wherein the at least one characteristic is determined based on the coefficients.

Aspect 10: The method of aspect 1, wherein the at least one characteristic includes a classification of the tissue.

Aspect 11: The method of aspect 10, wherein the classification is regarding the at least one tissue having a lesion thereon.

Aspect 12: The method of aspect 1, further comprising repeating the ablation and illumination procedures until a permanent lesion is formed on the at least one tissue.

Aspect 13: The method of aspect 1, further comprising determining a baseline diffuse reflectance spectra associated with the at least one tissue before the ablation procedure.

Aspect 14: The method of aspect 1, further comprising flushing the at least one tissue.

Aspect 15: The method of aspect 1, further comprising electrically mapping a surface of the at least on tissue.

Aspect 16: A system for determining at least one characteristic of at least one tissue, comprising: a computer hardware arrangement configured to: ablate the at least one tissue, illuminate the at least one tissue during the ablation procedure, and determine the at least one characteristic based on the ablation and illumination procedures.

Aspect 17: The system of aspect 16, wherein the computer hardware arrangement is further configured to ablate the at least one tissue using radiofrequency ablation.

Aspect 18: The system of aspect 16, wherein the computer hardware arrangement is further configured to perform the illumination procedure with a radiation in a visible spectrum.

Aspect 19: The system of aspect 16, wherein the computer hardware arrangement is further configured to: receive diffuse reflectance spectra based on the illumination procedure; and determine the at least one characteristic based on the received diffuse reflectance spectra.

Aspect 20: The system of aspect 19, wherein the computer hardware arrangement is further configured to invert the diffuse reflectance spectra using an inverse Monte Carlo procedure.

Aspect 21: The system of aspect 20, wherein the computer hardware arrangement is further configured to determine a concentration of at least one of (i) an oxy-myoglobin, (ii) a deoxy-myoglobin and (iii) a met-myoglobin based on the inverted diffuse reflectance spectra.

Aspect 22: The system of aspect 20, wherein the computer hardware arrangement is further configured to: determine a concentration of a met-myoglobin based on the inverted diffuse reflectance spectra; and perform at least one of (i) an analysis of variance test or (ii) a Tukey's multiple comparison test on the met-myoglobin.

Aspect 23: The system of aspect 20, wherein the computer hardware arrangement is further configured to fit the inverted diffuse reflectance spectra to a wavelength dependent model.

Aspect 24: The system of aspect 23, wherein the computer hardware arrangement is further configured to: receive a plurality of coefficients based on the fitting; and determine the at least one characteristic based on the coefficients.

Aspect 25: The system of aspect 16, wherein the at least one characteristic includes a classification of the tissue.

Aspect 26: The system of aspect 25, wherein the classification is regarding the at least one tissue having a lesion thereon.

Aspect 27: The system of aspect 16, wherein the computer hardware arrangement is further configured to repeat the ablation and illumination procedures until a permanent lesion on the at least one tissue is formed.

Aspect 28: The system of aspect 16, wherein the computer hardware arrangement is further configured to determine a baseline diffuse reflectance spectra associated with the at least one tissue before the ablation procedure.

Aspect 29: The system of aspect 16, wherein the computer hardware arrangement is further configured to flush the at least one tissue.

Aspect 30: The system of aspect 16, wherein the computer hardware arrangement is further configured to electrically map a surface of the at least on tissue.

Aspect 31: A non-transitory computer-accessible medium having stored thereon computer-executable instructions for determining at least one characteristic of at least one tissue, wherein, when a computer arrangement executes the instructions, the computer arrangement is configured to perform procedures comprising: ablating the at least one tissue; illuminating the at least one tissue during the ablation procedure; and determining the at least one characteristic based on the ablation and illumination procedures.

Aspect 32: The computer-accessible medium of aspect 31, wherein the computer hardware arrangement is further configured to ablate the at least one tissue using radiofrequency ablation.

Aspect 33: The computer-accessible medium of aspect 31, wherein the computer hardware arrangement is further configured to perform the illumination procedure with a radiation in a visible spectrum.

Aspect 34: The computer-accessible medium of aspect 31, wherein the computer hardware arrangement is further configured to: receive diffuse reflectance spectra based on the illumination procedure; and determine the at least one characteristic based on the received diffuse reflectance spectra.

Aspect 35: The computer-accessible medium of aspect 34, wherein the computer hardware arrangement is further configured to invert the diffuse reflectance spectra using an inverse Monte Carlo procedure.

Aspect 36: The computer-accessible medium of aspect 35, wherein the computer hardware arrangement is further configured to determine a concentration of at least one of (i) an oxy-myoglobin, (ii) a deoxy-myoglobin and (iii) a met-myoglobin based on the inverted diffuse reflectance spectra.

Aspect 37: The computer-accessible medium of aspect 35, wherein the computer hardware arrangement is further configured to: determine a concentration of a met-myoglobin based on the inverted diffuse reflectance spectra; and perform at least one of (i) an analysis of variance test or (ii) a Tukey's multiple comparison test on the met-myoglobin.

Aspect 38: The computer-accessible medium of aspect 35, wherein the computer hardware arrangement is further configured to fit the inverted diffuse reflectance spectra to a wavelength dependent model.

Aspect 39: The computer-accessible medium of aspect 38, wherein the computer hardware arrangement is further configured to: receive a plurality of coefficients based on the fitting; and determine the at least one characteristic based on the coefficients.

Aspect 40: The computer-accessible medium of aspect 31, wherein the at least one characteristic includes a classification of the tissue.

Aspect 41: The computer-accessible medium of aspect 41, wherein the classification is regarding the at least one tissue having a lesion thereon.

Aspect 42: The computer-accessible medium of aspect 16, wherein the computer hardware arrangement is further configured to repeat the ablation and illumination procedures until a permanent lesion on the at least one tissue is formed.

Aspect 43: The computer-accessible medium of aspect 31, wherein the computer hardware arrangement is further configured to determine a baseline diffuse reflectance spectra associated with the at least one tissue before the ablation procedure.

Aspect 44: The computer-accessible medium of aspect 31, wherein the computer hardware arrangement is further configured to flush the at least one tissue.

Aspect 45: The computer-accessible medium of aspect 31, wherein the computer hardware arrangement is further configured to electrically map a surface of the at least on tissue.

Aspect 46: A system for determining at least one characteristic of at least one tissue, comprising: a first electromagnetic radiation source configured to (i) generate at least one first radiation and (ii) provide the at least one first radiation to the at least one tissue so as to partially ablate the at least one tissue; a second electromagnetic radiation source configured to (i) generate at least one second radiation, and (ii) provide the at least one second radiation to the at least one tissue; a detector arrangement configured to (i) obtain a return radiation from the at least one tissue that is based on the at least one second radiation impacting the at least one tissue and the at least partial ablation caused by the at least one first radiation, and (ii) provide data associated with at least one further characteristic of the returned radiation; and a computer processing arrangement configured to determine the at least one characteristic based on the data.

Aspect 47: The system of aspect 46, wherein the data includes information as to whether the at least one tissue has been permanently damaged.

Aspect 48: The system of aspect 46, wherein the at least one second radiation is in a visible spectrum.

Aspect 49: The system of aspect 46, wherein the at least one characteristic includes a classification of the tissue.

Aspect 50: The system of aspect 49, wherein the classification is regarding the at least one tissue having a lesion thereon.

Aspect 51: The system of aspect 46, further comprising at least one flushing arrangement configured to flush the at least one tissue.

Aspect 52: The system of aspect 46, further comprising a voltage arrangement configured to generate at least one voltage, wherein the detector arrangement is further configured to obtain a return voltage from the at least one tissue that is based on the at least one second radiation impacting the at least one tissue.

Aspect 53: The system of aspect 52, wherein the computer processing arrangement is further configured to generate at least one map of a surface of the at least one tissue based on the return voltage.

Aspect 54: A method for ablating at least one tissue, comprising: determining at least one location of at least one dead portion of the at least one tissue; providing the at least one location to an ablative source arrangement; moving the ablative source arrangement to at least one further location based on the at least one location; and ablating the at least one further location of the at least one tissue.

Aspect 55: The method of aspect 54, wherein the determination procedure is based on at least one intensity and at least one wavelength of a radiation produced by the ablative source arrangement.

Aspect 56: The method of aspect 54, further comprising flushing the at least one tissue using a flushing arrangement.

Aspect 57: The method of aspect 54, further comprising mapping a surface of the at least one tissue using a voltage generator.

Aspect 58: A catheter, comprising: a near infrared radiation generating first arrangement; a visible radiation generating second arrangement; and an ablative arrangement.

Aspect 59: The catheter of aspect 58, further comprising a flushing arrangement.

Aspect 60: The catheter of aspect 58, further comprising a voltage generator.

Exemplary Real-Time Monitoring of Cardiac Lesion Progression Using a Diffuse Reflectance Spectroscopy Integrated Ablation Catheter The exemplary system, method, and computer-accessible medium, according to an exemplary embodiment of the present disclosure, can be used for rapid processing of DR spectra to approximate lesion depth in various cardiac tissue regions including the right ("RA") and left atria ("LA") and right ventricular ("RV") regions. A set of parameters termed "lesion optical indices" ("LOI") encapsulating observations of spectral morphological differences between ablated and unablated tissue can be defined. Utilizing these features, the classification of DR spectral integrity and subsequent estimation of lesion depth was demonstrated. A procedure for real-time monitoring of lesion progression can be applied in ex vivo swine specimens. The exemplary method can be capable of performing DR-facilitated lesion estimation in <5 ms using un-optimized code on a commercial laptop. Exemplary experimental validation was performed by comparing procedure estimates to vital stained cross-sections for various lesion sizes showed strong correspondence. Microscopic evaluation of DRS-predicted, heavily ablated tissue using high-resolution OCT ("HR-OCT") and histopathology were coincident with markers for irreversible damage; conversely, little to no evidence of irreversible damage was noted in DRS-predicted lightly to untreated tissue.

Exemplary DR Spectroscopy System

An exemplary schematic diagram of the exemplary catheter ablation system 2300 is shown in FIGS. 23A and 23B. Optically integrated ablation catheters (e.g., catheter 2305) was used to facilitate simultaneous sampling of tissue diffuse reflectance at the ablation site (e.g., sampled 2310) during RF energy delivery. Custom aluminum catheter tips were designed to house an illumination and collection fiber pair 2315 separated by a distance of 2.35+/−0.05 mm. This separation was selected to yield particular sensitivity to tissue absorption effects. (See, e.g., References 19 and 20). The fiber-embedded custom tip was mounted onto a commercially available RF catheter (e.g., Biosense Webster, Diamond Bar, CA) and electrically coupled using conductive epoxy. Impedance comparisons for the fiber-integrated catheter with an unmounted identical catheter yielded values within 6% of each other. The final integrated catheter diameter was <13F. Typical ablation catheters range on the order of 6F-14F.

Broadband light from a tungsten halogen source (e.g., HL-2000-HP) was delivered onto the tissue via a 200 µm optical fiber. A 450 nm longpass filter was placed between the lamp output and the source fiber input to avoid tissue and operator exposure to UV light. Diffusely backscattered light was received by an identical collection fiber and routed to a spectrometer (e.g., 600-1000 nm) (e.g., C9405CB, Hamamatsu). Spectral measurements were recorded at 30-50 Hz. A custom LabVIEW program was used to facilitate data acquisition. Unless otherwise mentioned, DR measurements were converted to relative reflectance spectra, $R_{Rel}$, using a similar process as described in (see, e.g., Reference 22); which included dark subtraction, removal of instrument response, and normalization at 650 nm from $TiO_2$-based, silicone phantom measurement of known optical properties.

Exemplary Sample Preparation

A total of ten fresh swine hearts were acquired. Experiments were conducted within 24 hours of sacrifice. Wedges were surgically resected from LA, RA, and RV regions and submerged in 37° C. maintained phosphate buffered saline ("PBS") under pulsatile flow. Catheter ablation and simultaneous optical measurements were performed on the endocardial surface in atrial samples and on the epicardial surface in RV samples. An additional set of lesions were created on the endocardial RV using open-irrigated catheters (e.g., n=7) to assess the impact of irrigation on lesion spectra.

Lesions were sagittally bisected immediately after spectral data acquisition. To evaluate the extent of microscopic tissue injury, one half was preserved in formalin for 24 hours and paraffin embedded for further histopathological assessment. Hematoxylin and eosin ("H&E") staining in addition to Masson's Trichrome staining was performed on adjacent 5 µm sections to evaluate markers for tissue injury. A set of lesions were imaged prior to bisection under HR-OCT (e.g., 2.72 µm-5.52 µm axial-lateral resolution) to examine microscopic features while the specimen remained intact. Details of the HR-OCT system have been described elsewhere. (See, e.g., Reference 24). The remaining half of the gross specimen was immersed in 1% 2,3,5-triphenyl-2H-tetrazolium chloride ("TTC") vital stain for 25 minutes at room temperature to delineate tissue injury. To avoid the variation in tissue size caused by histological preparation, lesion size was evaluated using digitized camera images of gross, TTC-stained specimens. Agreement between optical measurements and lesion depth values were quantified in terms of the Pearson correlation coefficient.

Exemplary Optical Measurement of RF Ablated Samples

The fiber-integrated catheter was connected to a commercial RF generator (e.g., Stockert 70, Biosense Webster, Diamond Bar, CA) under the manual unipolar, power-controlled mode. Target power settings were varied between 3-25 W for durations between 10-120 s to vary the extent of tissue injury. Tissue bioelectrical impedance and delivered power were recorded continuously throughout the ablation process using a commercial DAQ system (e.g., NI USB-6218 BNC, National Instruments).

Preliminary experiments were first conducted to evaluate possible features in spectral morphology that were distinct in treated and untreated specimens. In these lesions, continuous data acquisition was maintained from three to five seconds prior to application of RF energy until several seconds post ablation. Spectra retrospectively chosen from confirmed lesions with depths>=5 mm in RV samples (e.g., n=6) were used to guide LOI choices. In atrial preparations (e.g., n=6 each) spectra taken from confirmed transmural lesions were used. These lesions were not included in the final analysis. A similar ablation-optical measurement protocol was applied for generating a total of 24 epicardial lesions in the RV and 33 and 31 endocardial lesions in RA and LA samples, respectively. To evaluate the influence of open irrigation on treated tissue spectra, a set of 7 lesions were generated in swine LA specimens using irrigated ablation at a flow rate of 30 ml/min. Spectral measurements were obtained post-ablation since the irrigated ablation catheters used in this study were not optically integrated.

Exemplary Feature Extraction From DR Spectra

FIG. 24 shows an exemplary flow chart of a method 2400 for processing DR spectra (e.g., acquired spectra 2405) according to an exemplary embodiment of the present disclosure. Five features were utilized based on observations of differences in spectral morphology associated with treated and normal tissue sites (e.g., Eqs. 1-5). These were computed as follows:

$$LOI_1 = \frac{R_{Rel,965nm}}{R_{Rel,616nm}} \quad (1)$$

$$LOI_2 = \frac{R_{Rel,930nm}}{R_{Rel,785nm}} \quad (2)$$

$$LOI_3 = \int_{\lambda_a}^{\lambda_b} R_{Rel} / R_{Rel,961nm} \, d\lambda \quad (3)$$

$$LOI_4 = \underset{\lambda \in \Lambda}{\operatorname{argmin}} \, R_{Rel} \quad (4)$$

$$LOI_5 = \frac{R_{Rel,893nm}}{R_{Rel,835nm}} \quad (5)$$

where $\lambda_a$ and $\lambda_b$ can be 600 nm and 1000 nm, respectively. Λ can be taken to be the set of wavelengths between the 730-800 nm region. It should be noted that these parameters can be self-contained and do not need baseline normalization.

Thermal treatment of the myocardium induces changes in the underlying physiological and chemical properties. Therefore, features derived from a physical model (e.g., using feature extraction procedure 2410) can be used to further enhance lesion assessment. The exemplary features can be stored in an electronic database for access during the exemplary procedure for determining the lesion size. In addition to LOI parameters, absorption and reduced scattering spectra were derived from DR spectra using an inverse Monte Carlo ("iMC") method. (See, e.g., Reference 22). Briefly, a look up table-based forward model was generated through MC simulations run for the catheter optical geometry over a range of absorption (e.g., 0-10 cm$^{-1}$) and reduced scattering (e.g., 2-60 cm$^{-1}$) values. Absorption was modeled as a weighted sum of dominant cardiac chromophores in the near-infrared region, namely oxygenated and deoxygenated hemoglobin (e.g., "HbO", "Hb") and myoglobin ("MbO", "Mb"), metmyoglobin ("Mmb"), lipid and water (Eq. 6).

$$\mu_a(\lambda) = B \cdot (S \cdot \varepsilon_{HbO} + (1-S) \cdot \varepsilon_{HbO}) + C_{MbO} \cdot \varepsilon_{MbO} + C_{Mb} \cdot \varepsilon_{Mb} + C_{Mmb} \cdot \varepsilon_{Mmb} + f_{water} \cdot \mu_{water} + f_{lipid} \cdot \mu_{lipid} \quad (6)$$

Reduced scattering was assumed to exhibit a power law dependence with wavelength and was modeled to accommodate both Rayleigh and Mie scattering contributions, as follows:

$$\mu'_s(\lambda) = A[f_{Ray}(\lambda/600 \text{ nm})^{-4} + (1-f_{Ray})(\lambda/600 \text{ nm})^{-b_{Mie}}] \quad (7)$$

where A and $f_{Ray}$ can be the Scattering Amplitude and Rayleigh fraction, respectively. $b_{Mie}$ can be the unitless scattering slope parameter and gives an indication on Mie equivalent radii of spherical scatterers. These parameters, along with absorber concentrations were determined using a Levenberg-Marquardt optimization scheme. To reduce the effects of local minima convergence, a series of 6 optimizations were run per spectra with different initial guesses. The optimal solution was taken to be the result which achieved the greatest $R^2$ value.

Exemplary Contact Classification

As shown in FIG. 24, a preliminary contact classification stage (e.g., contact classifier 2415) was implemented to filter out spectra that were unsuitable for lesion size estimation (e.g., blood contaminated). For this, a linear discriminant analysis ("LDA") classifier was employed to categorize spectra into either one of two classes: non-contact (e.g., blood) and contact (e.g., measured from untreated and treated tissue). An unbiased estimate of classification performance was obtained using "leave one out" cross-validation using the cvpartiton and crossval functions within MATLAB. A rapid (e.g., subsecond) spectral analysis can be used for lesion assessment. Therefore, the feature set for classification was limited to parameters that did not utilize iterative optimization for extraction (e.g., LOIs). These parameters were also analyzed using repeated measure ANOVA and Tukey's multiple comparison tests to evaluate statistical significance between groups and diagnostic potential for treatment discrimination.

Exemplary Lesion Size Estimation

Spectra classified as in contact underwent further processing to determine the corresponding extent of treatment. To accomplish lesion size estimation, as shown in FIG. 24, a lesion regression model 2420 was generated by obtaining solution weights, W, to the second order normal equation in Eq. 8, where X can be an N×2M feature vector comprised of LOI values and their squares, and Y can be the N×1 lesion depth.

$$W = (X^T X)^{-1} X^T Y \quad (8)$$

A quadratic relationship was chosen based on prior studies in ventricular tissue that demonstrated a second order correspondence. (See, e.g., Reference 18). Due to anatomical differences between the chambers a set of weights were computed separately for each chamber.

In order to compare the influence of optical parameter inclusion on estimation performance, a separate estimation model was determined which consisted of both the LOI values, in addition to $\mu_{a,630 \text{ nm}}$ and b. These were selected based on previous literature examining optical and physical changes within the thermally treated myocardium. (See, e.g., References 22, 25 and 26). All calculations were performed on a 2013 MacBook Air equipped with a 1.7 GHz Intel i7 CPU and 8 GB RAM.

Exemplary Results

Exemplary Effect of RFA on DR Measurements

Figure 25A:
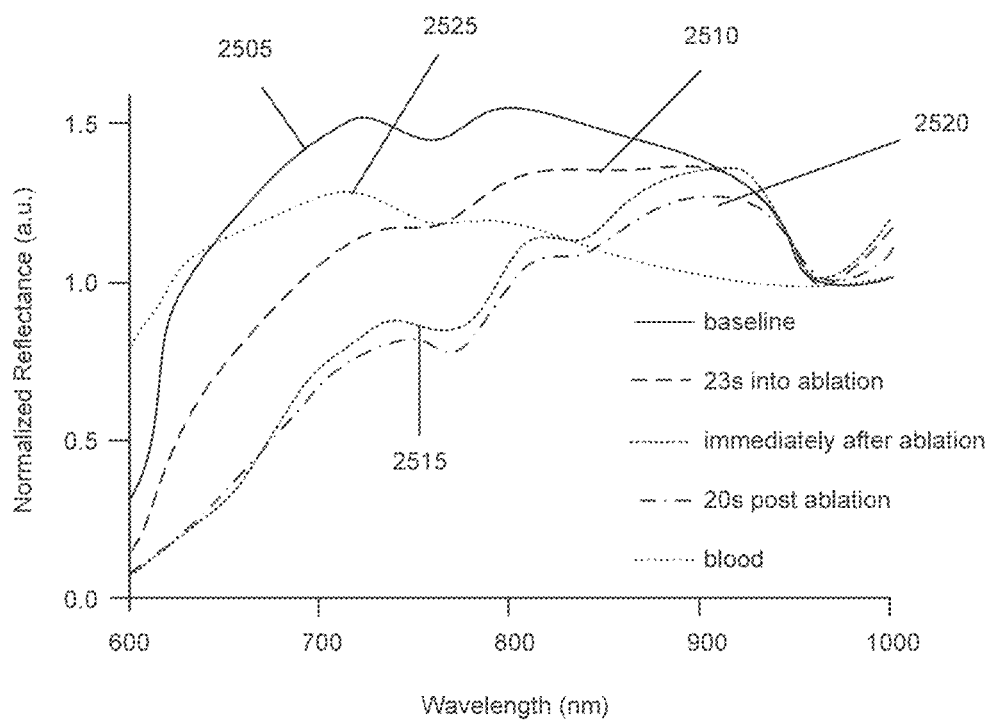
FIGS. 25A-25F are exemplary graphs of exemplary effects of radiofrequency ablation on recovered $R_{Rel}$ spectra according to an exemplary embodiment of the present disclosure.
Figure 25B:
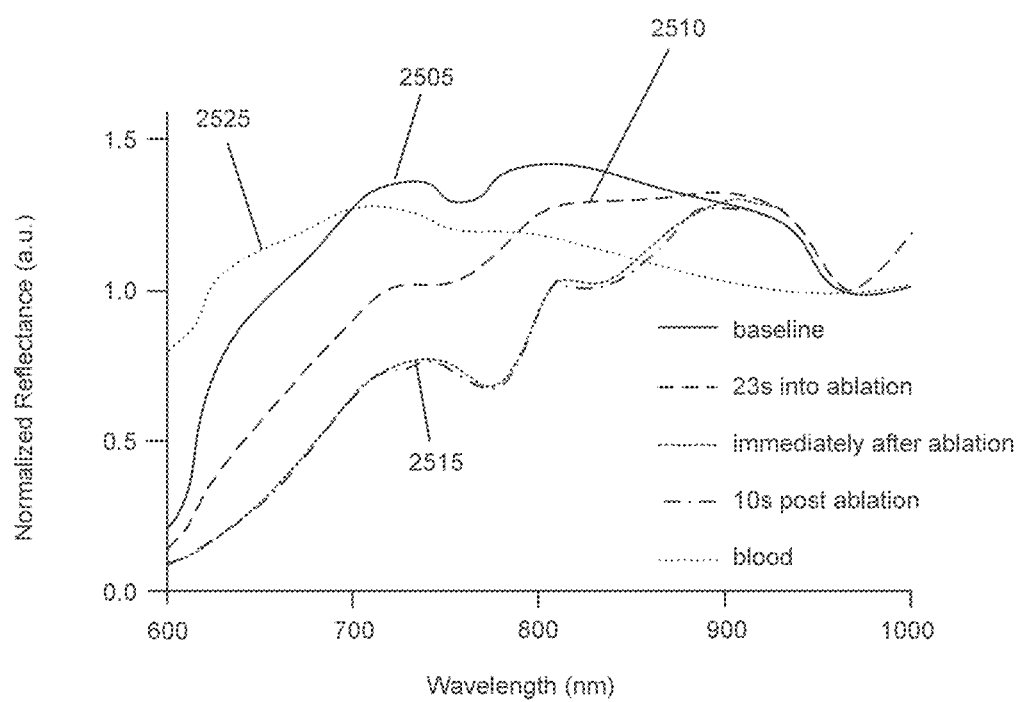
Figure 25C:
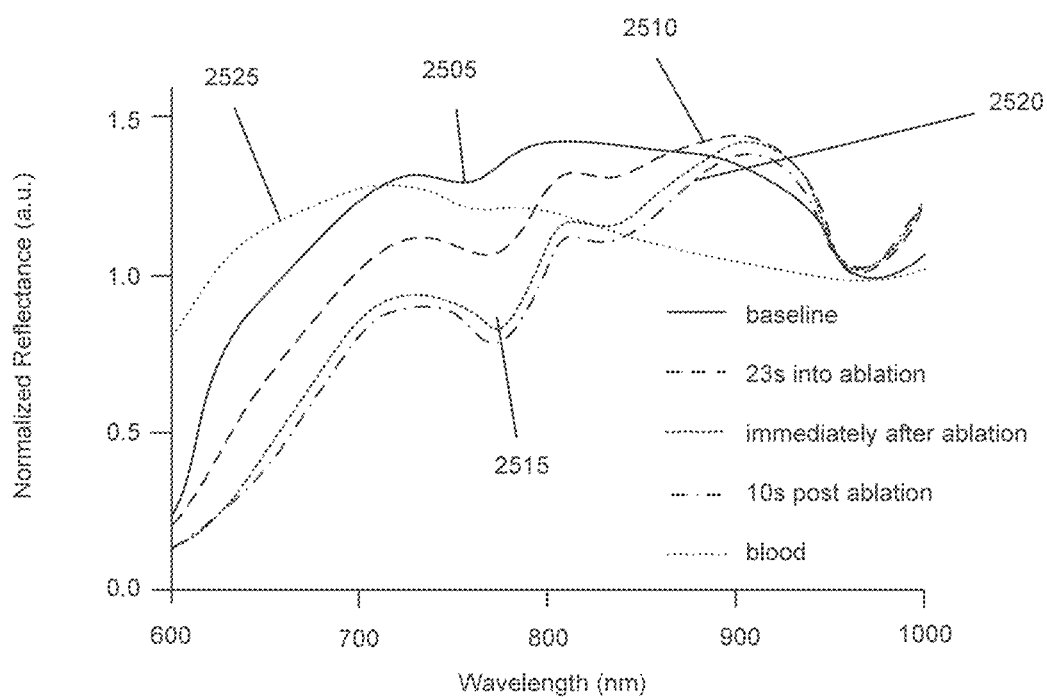
Figure 25D:
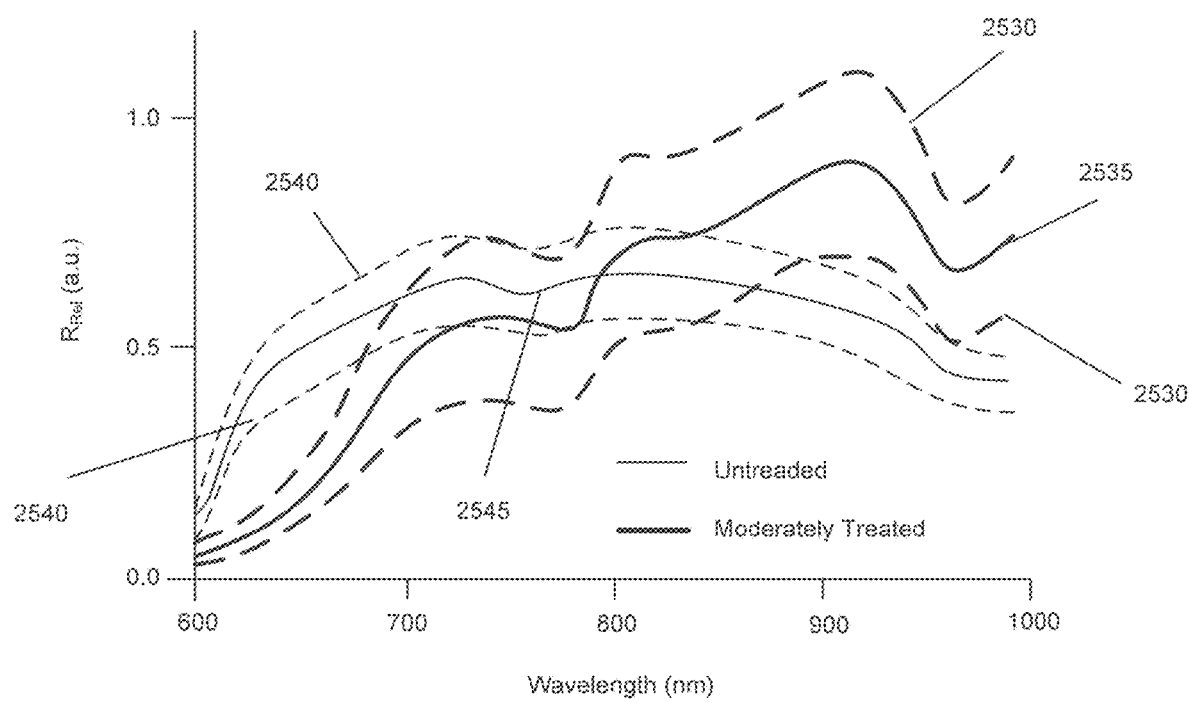
Figure 25E:
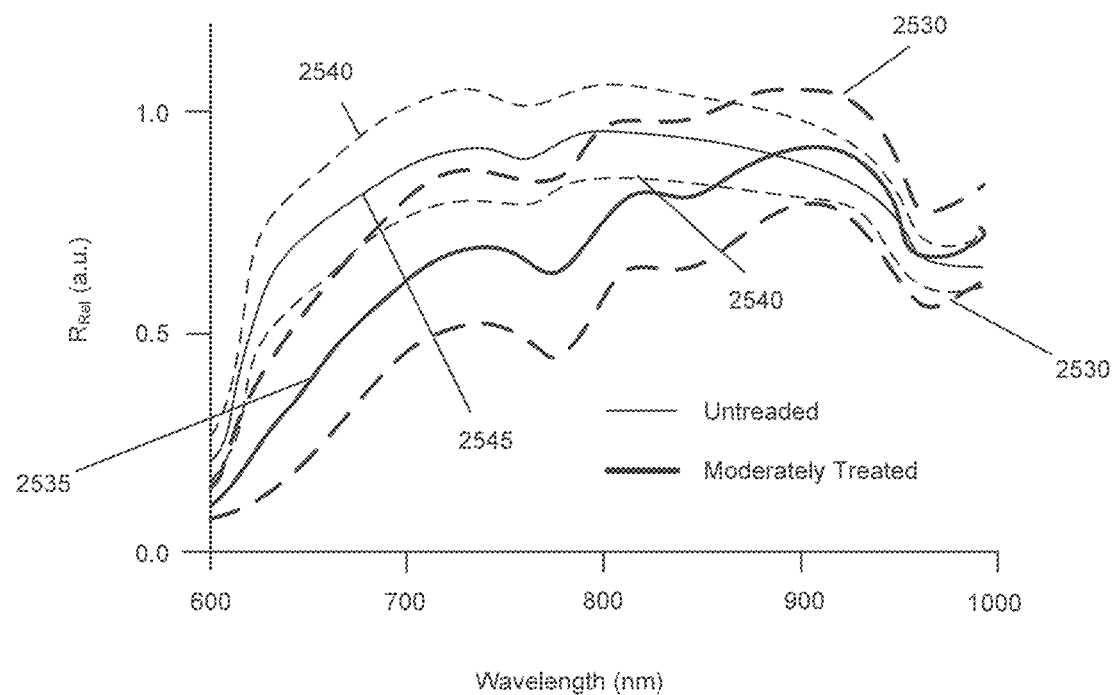
Figure 25F:
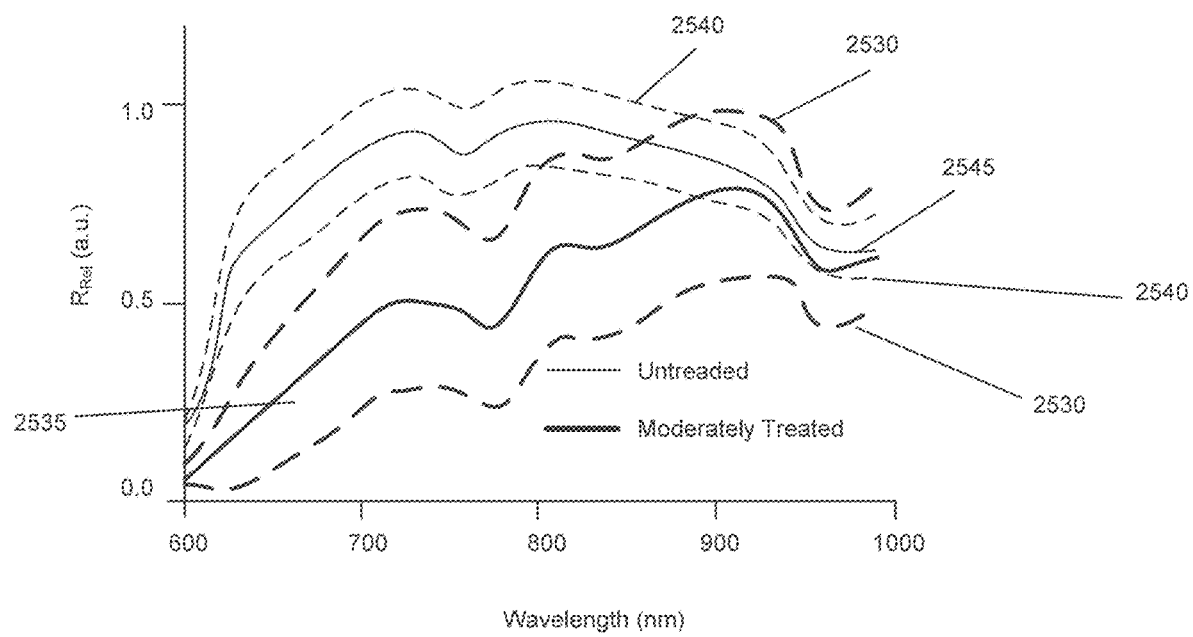

The effect of RFA treatment (e.g., lines 2530 and 2535 shown in FIGS. 25D-25F) on measured tissue reflectance was evaluated and compared to that of untreated cardiac tissue (e.g., lines 2540 and 2545 shown in FIGS. 25D-25F). Spectral measurements were retrospectively taken from TTC-confirmed transmural lesions in the atria and ventricular lesions extending beyond 4 mm. FIGS. 25A-25F show exemplary graphs of the wavelength dependent responses in tissue reflectance with progressive RF energy deposition for representative atrial and ventricular specimens for baseline (line 2505), 23 second into ablation (line 2510), immediately after ablation (line 2515), 10 second post ablation (line 2520), and for blood (line 2525). Marked differences in spectral shape were apparent throughout the entire spectral range and became more prominent with treatment. A distinct and broad reduction in $R_{Rel}$ spectral shape was noted between 600-700 nm. A broad increase in reflectance was observed>approximately 800 nm in ventricular specimens and >approximately 870 nm in atrial tissues. This rise was concurrent with a dip in reflectance at approximately 835 nm and an approximately 18 nm red shift in the local minima lying between 730-800 nm. Ablated spectra also exhibited a subtle sharpening of the peak near 960 nm. Overall the relative ratio between mean $R_{Rel}$ values in the 600-700 nm region and 830-965 nm region were considerably lower than in untreated spectra than with increased treatment. These observations were consistent across chambers and were used as a basis to parameterize LOIs.

Changes in spectral shape in ablated tissue exhibited characteristic features primarily in regions coinciding with prominent Mmb absorption (see e.g., FIGS. 25A-25F), in addition to a scattering-induced spectral offset and tilting. Although generally similar in spectral shape, RV samples exhibited lower mean $R_{Rel}$ values over the entire wavelength range for untreated preparations compared to atrial tissues. In addition, RV treated spectral changes were more dramatic with a larger reduction centered at 630 nm and a greater rise in $R_{Rel}$ at longer wavelengths, followed by RA, then LA. This can be attributed to the inherently greater amounts of myoglobin present in the RV as compared to atrial samples. Because Mmb can be a large contributor to spectral shape changes seen with ablation treatment, a greater myoglobin reservoir can be likely to absorb more at baseline and generate a greater measured response during ferrous to ferric state conversions. It can also be likely that the increased endocardial thickness within atrial samples can limit myocardial sampling and hence scattering-induced reflectance changes therein. The relatively larger confidence intervals range observed in the atria as compared to ventricular samples (see, e.g., FIGS. 25A-25F) could be explained by the interplay between the optical sampling volume and tissue wall thickness. In atrial samples, the selection criterion was lesion transmurality, which may not imply uniform wall thickness across samples. Because typical atrial wall thicknesses can be within the range of longitudinal sampling for this optical geometry, measurements can be likely to be affected by wall thickness as well as lesion extent. In RV samples however, the inherently greater wall thickness can be likely to exceed the sampling depth and mimic a semi-infinite geometry thus less susceptible to these factors.

LOI parameters were then computed for lesions created on each tissue region, their corresponding unablated baseline spectra, as well as spectra acquired from whole swine blood. Statistical analysis revealed significant differences (e.g., p<0.0001) between untreated and treated tissue values as well as treated tissue and blood for all LOIs in both ventricular (see e.g., FIG. 24) and atrial cohorts. These results suggested that these LOIs were potentially suitable for spectra classification and lesion size approximation.

Exemplary Physical Model Fitting Results

Figure 26:
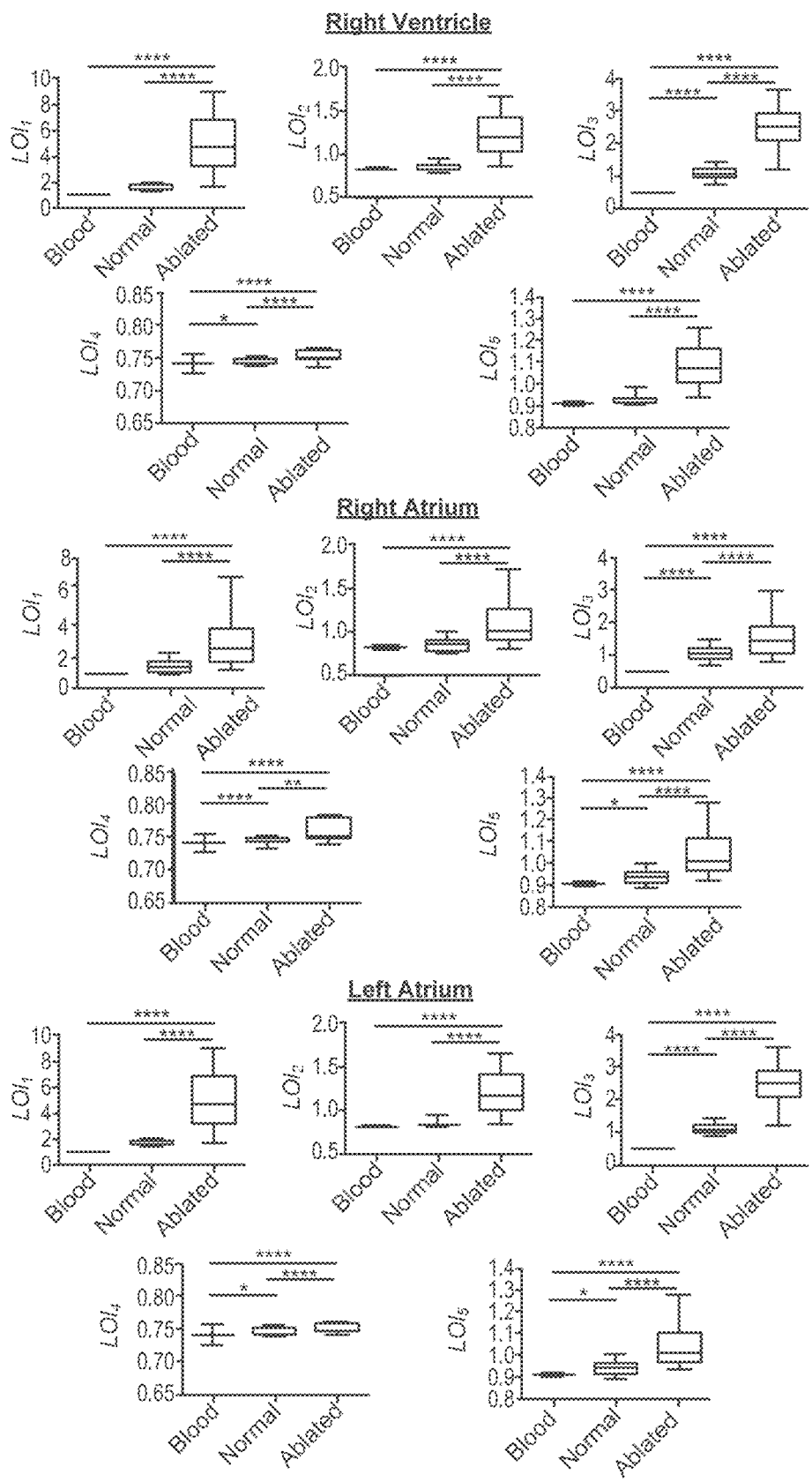
FIG. 26 is a set of graph of exemplary statistical results for lesion optical indices values derived from both atrial and ventricular samples according to an exemplary embodiment of the present disclosure.
Figure 27:
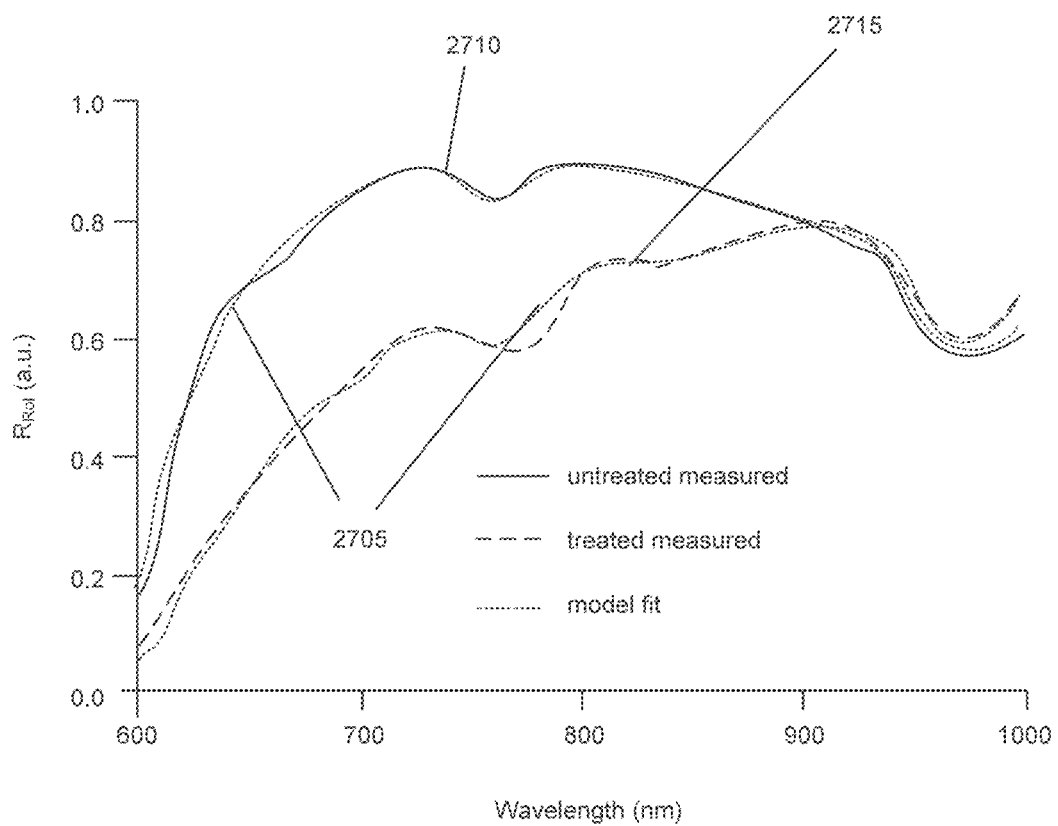
FIG. 27 is a graph of an exemplary model used to fit data for untreated and treated right atria spectra according to an exemplary embodiment of the present disclosure.
Figure 28A:
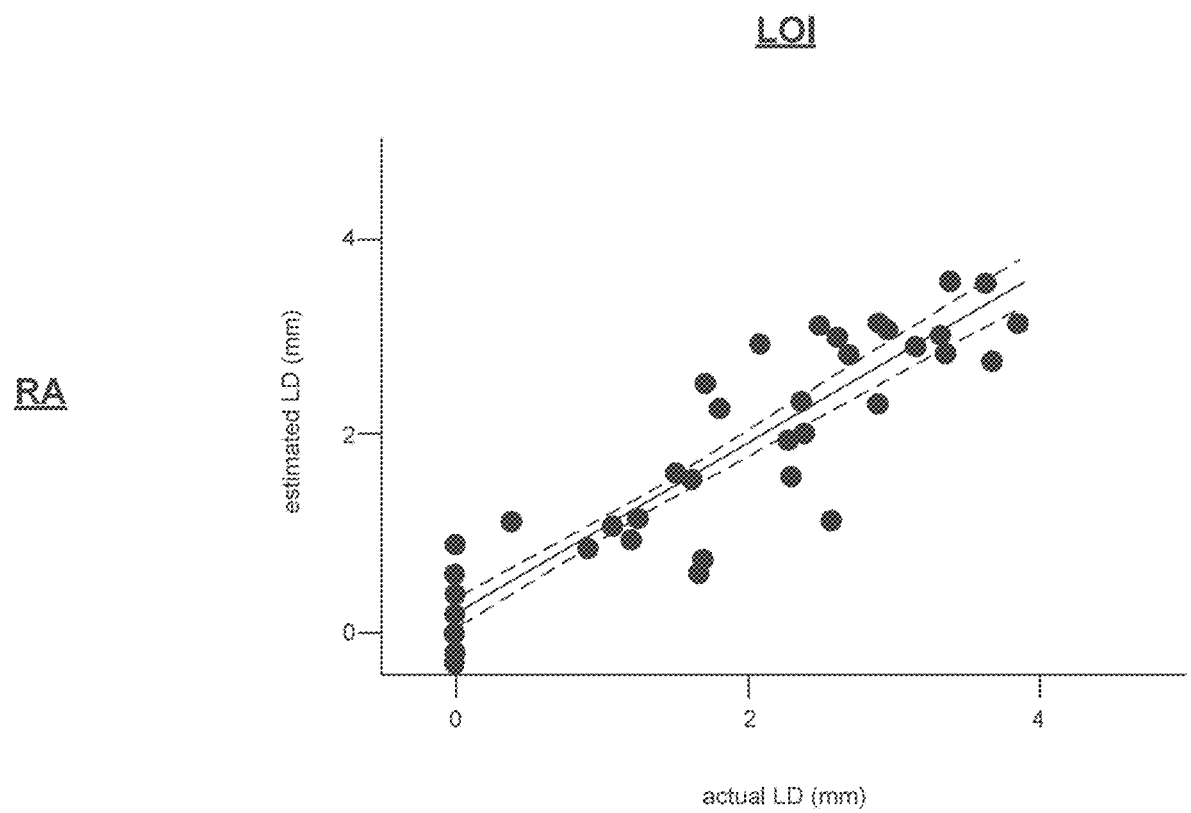
FIGS. 28A-28D are graphs of exemplary lesion estimation results obtained using both lesion optical indices-based and inverse Monte Carlo-based regression models according to an exemplary embodiment of the present disclosure.
Figure 28B:
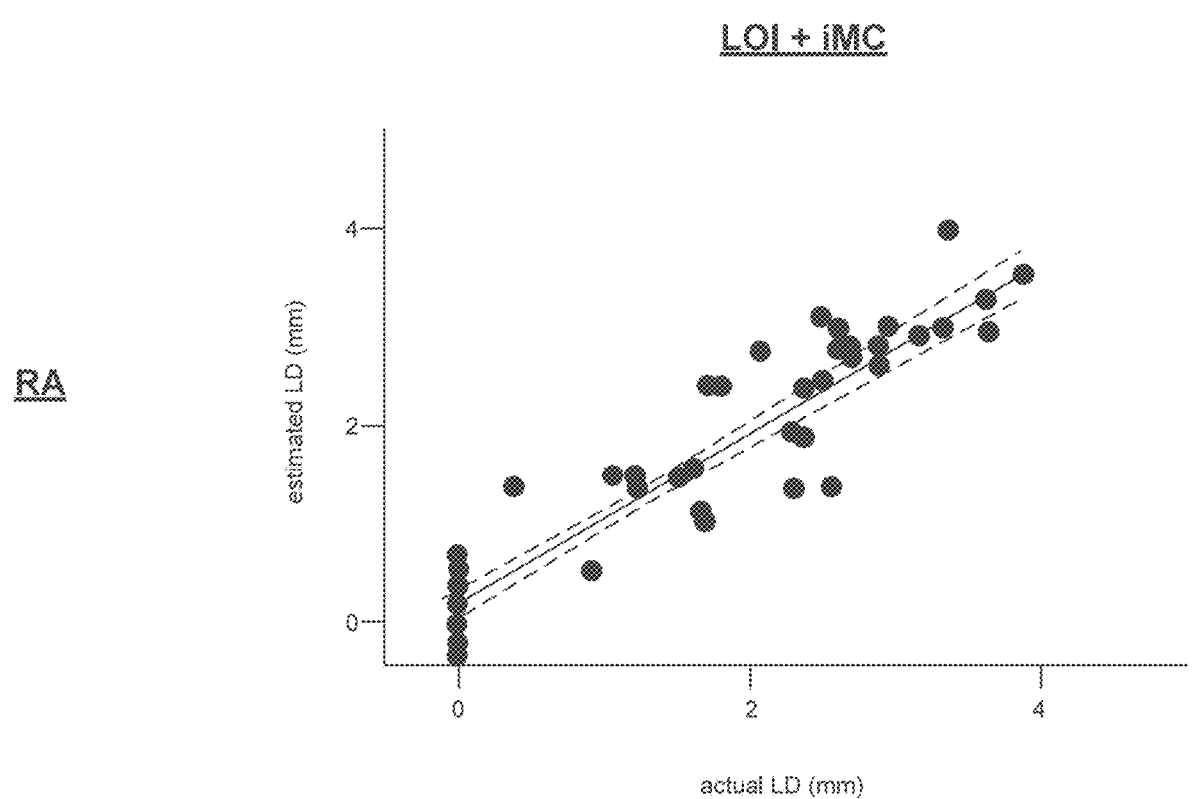
Figure 28C:
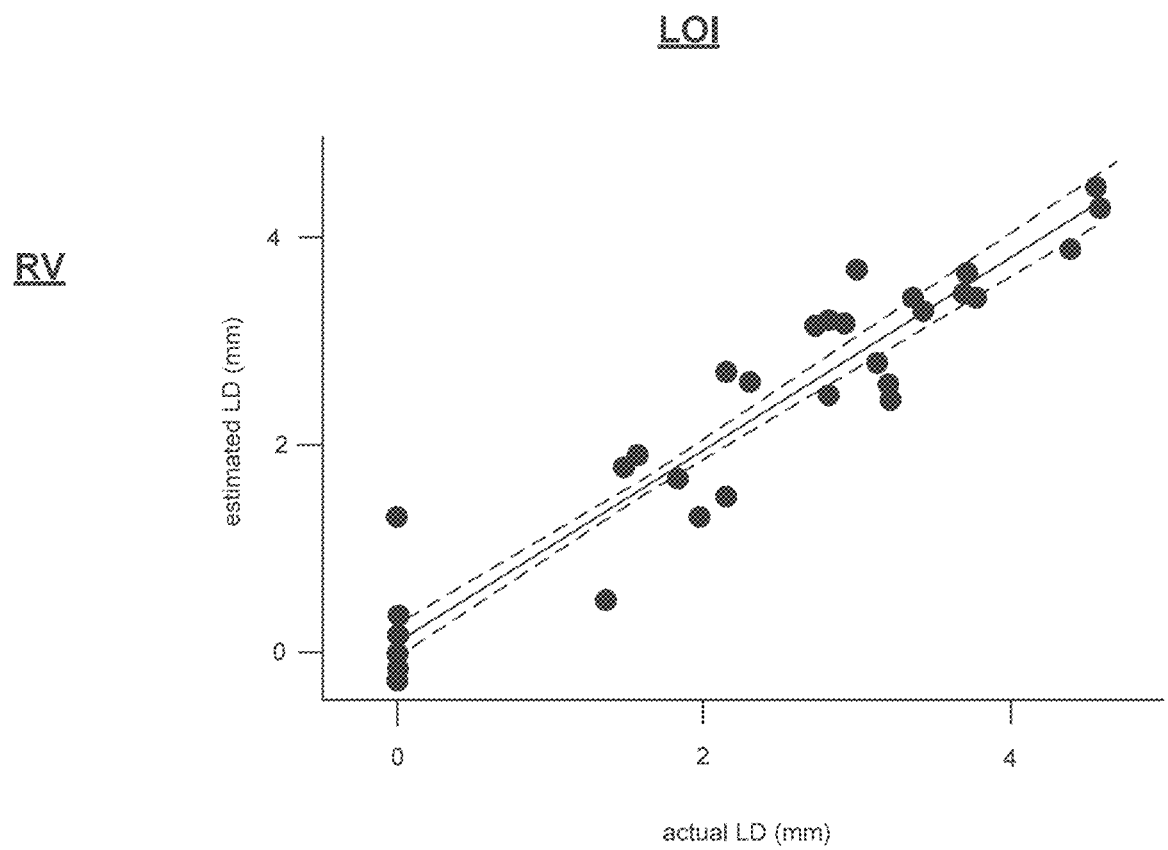
Figure 28D:
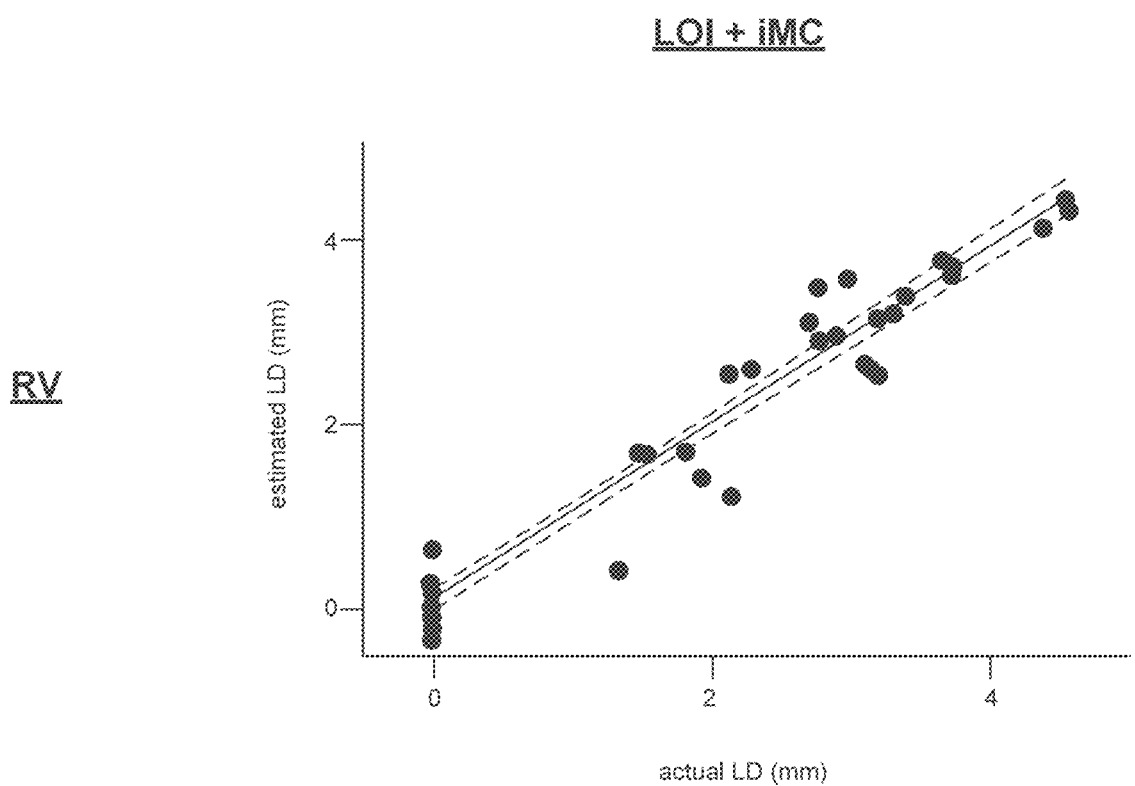

In addition to parameters based on spectral morphology, tissue optical properties were determined using an inverse MC method. FIG. 26 is a set of graph of exemplary statistical results for lesion optical indices values derived from both atrial and ventricular samples according to an exemplary embodiment of the present disclosure. FIG. 27 shows an exemplary graph of a typical example model fitting results (line 2705) obtained from untreated spectra (line 2710) and treated RA spectra (line 2715). Overall, good agreement between estimated and experimental data was observed as judged by low residuals. Mean $R^2$ values for untreated and treated spectral fits were 0.995 and 0.985, respectively. The slightly reduced $R^2$ value for the treated spectra could be explained by greater residuals caused by the apparent broadening and redshifted local minima lying between the 750 nm-800 nm regions. This discrepancy could be attributed to RF-induced Mmb formation and increases in $pH^{23}$.

Exemplary Contact Classification Accuracy

A LDA classifier was generated in order to ensure the fidelity of spectra prior to lesion size estimation. The classifier was designed to accept all seven LOIs as features and determine whether measurements had originated from normal tissue, ablated tissue, or were blood contaminated. Performance of the classifier is depicted in Table 1. Good classification accuracy (e.g., >90%) was observed across all chambers and was best in RA specimens (e.g., n=66). Nevertheless, slight errors (e.g., <3%) were observed RV (e.g., n=48) and LA (e.g., n=62) specimens in discriminating ablated vs. untreated tissue.

TABLE 1

Performance of tissue contact classification.

| Region | CVCR [%] | Sensitivity [%] | Specificity [%] |
|---|---|---|---|
| RA | 99.1 | 100 | 100 |
| LA | 97.5 | 100 | 96.7 |
| RV | 98.1 | 100 | 97.9 |

CVCR - cross-validated classification rate

Exemplary Regression Model Performance

A LOI-based, quadratic regression model was trained to carry out lesion size estimation. FIG. 28A-28D show exemplary graphs of lesion depth predictions generated by the exemplary model in comparison to actual values obtained through digitized lesion cross sections. Table 2 provides Pearson correlation coefficient values for RV, RA, and LA for LOI-based and LOI+iMC-based regression models demonstrating strong concordance with experimental data (e.g., R>0.9) on all chambers tested. It was observed that the inclusion of optical parameters slightly enhanced agreement increasing correlation coefficients at most 2%. Because the addition of iMC-derived terms only showed marginal improvement in lesion size estimation, it can be difficult to justify the additional cost in computational time (e.g., 1-10 s per spectra depending on lesion properties) utilized as a result of iterative optimization and thereby limiting its application for real-time use; LOI-based estimates were computed within 2-5 ms on average. However, this procedure could potentially be used for investigating the underlying temporal dynamics in myocardial biochemistry and ultrastructure as a result of RF ablation.

TABLE 2

Pearson correlation coefficients across chambers

| Region | LOI-based | LOI + iMC-based |
|---|---|---|
| RA | 0.932 | 0.952 |
| LA | 0.912 | 0.925 |
| RV | 0.969 | 0.977 |

Real-time monitoring of lesion formation

Figure 29A:
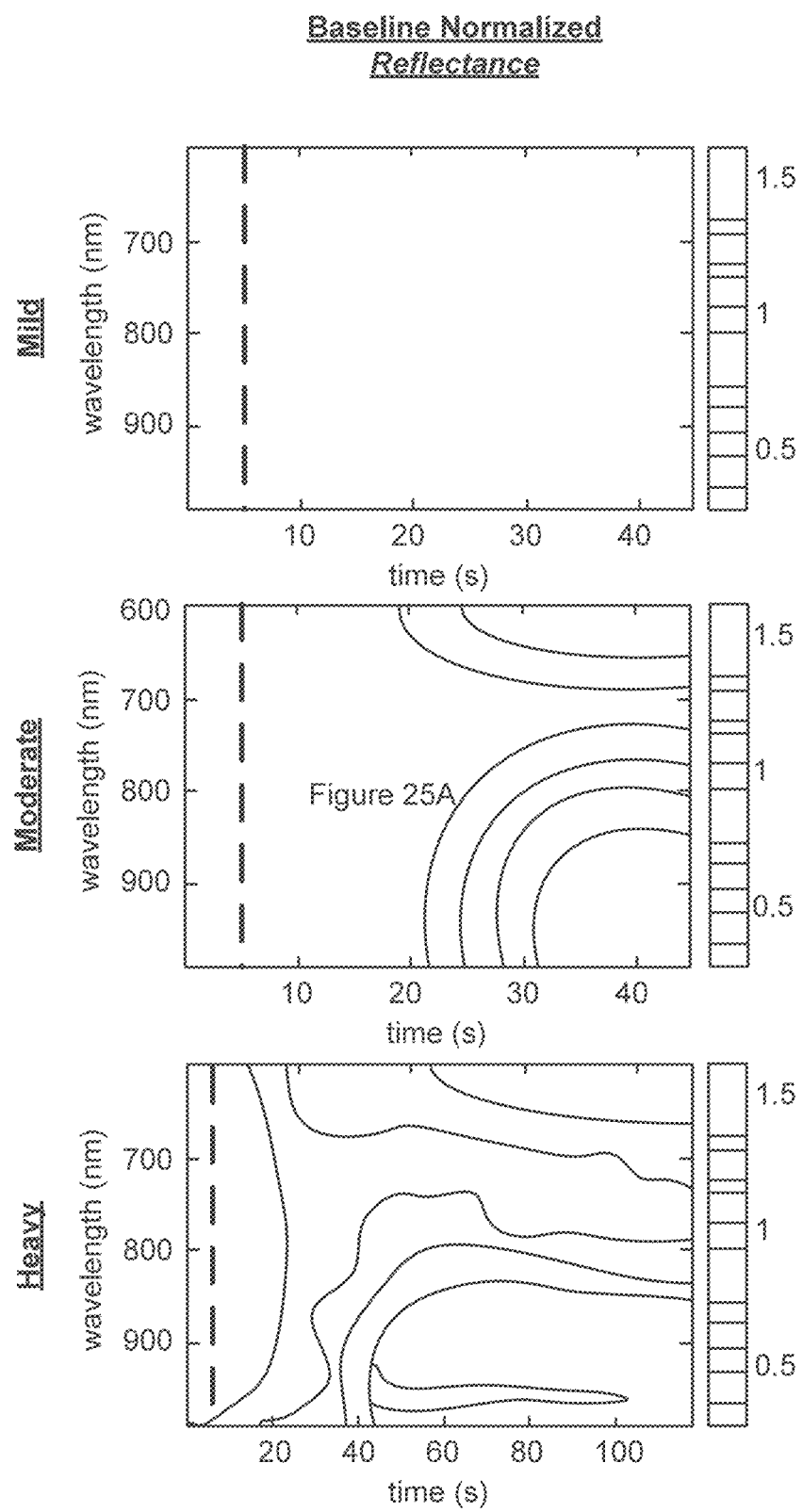
FIG. 29A is an exemplary set of exemplary spectro-temporal responses during radiofrequency energy delivery according to an exemplary embodiment of the present disclosure.
Figure 29C:
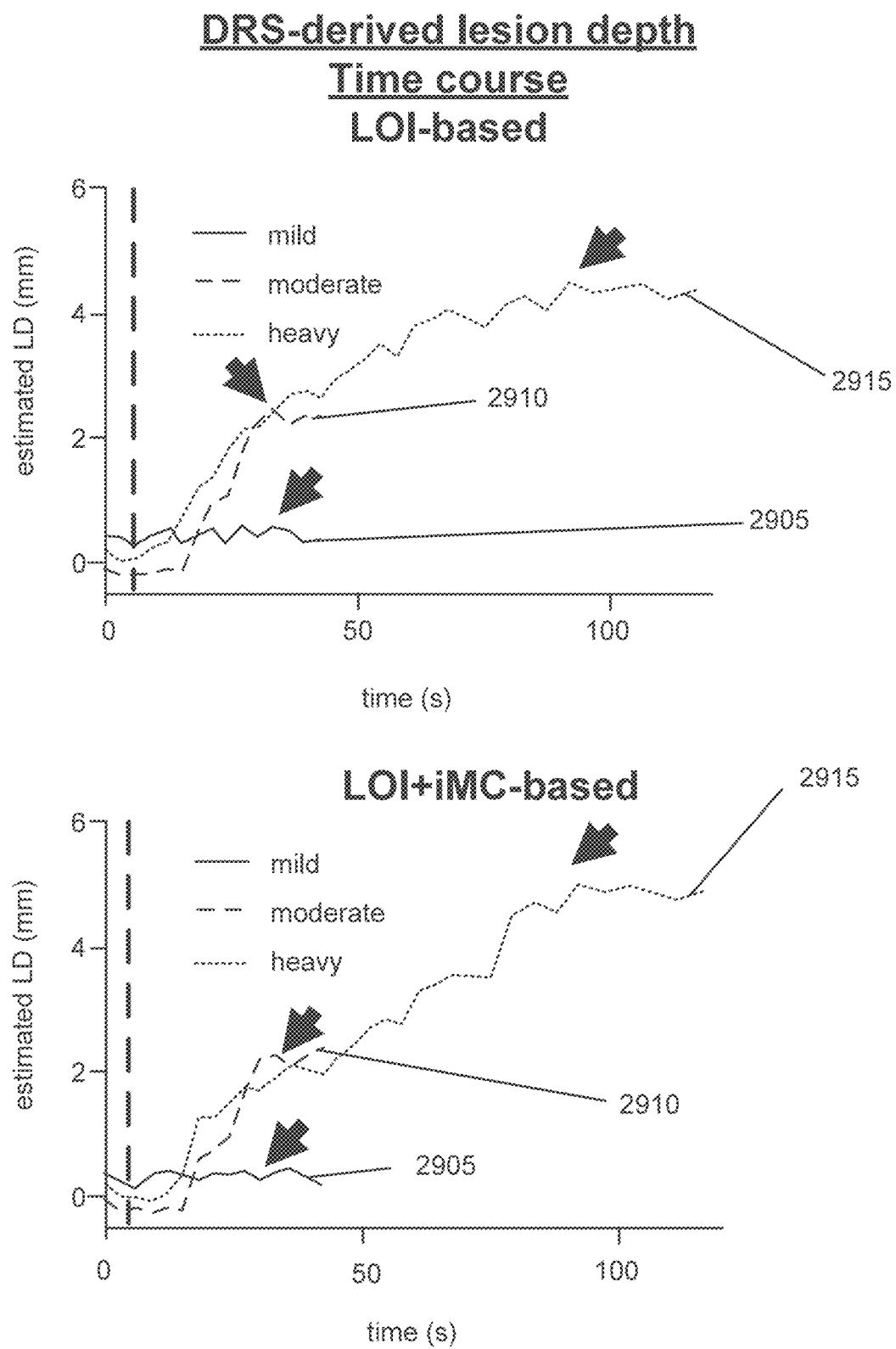
FIG. 29C is a set of graphs of exemplary time courses for lesion optical indices and lesion optical indices+inverse Monte Carlo-based estimations for lesion according to an exemplary embodiment of the present disclosure.

Dynamic lesion size estimates were computed for a set of lesions with varied doses of applied RF energy delivery. (See e.g., FIGS. 29A-30E). For example, FIG. 29C shows a set of exemplary graphs of exemplary time courses for lesion optical indices and lesion optical indices+inverse Monte Carlo-based estimations for lesions (e.g., mild 2905, moderate 2910, and heavy 2915) according to an exemplary embodiment of the present disclosure. In general, a short delay following ablation onset was noted followed by a monotonic increase with progressive treatment. Continuous monitoring after ablation offset demonstrated reasonable stability in estimated values. Resulting lesion depth values for both LOI- and LOI+iMC-based regression models were within 10% of the actual depths measured from digitized TTC stained images.

Exemplary Microscopic Evaluation of RF Treatment

Figure 30A:
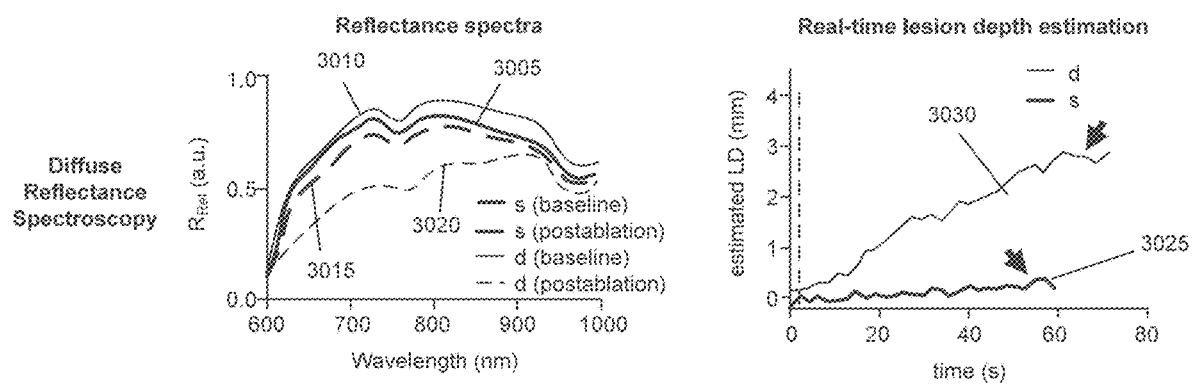
FIG. 30A is a set of graphs of exemplary baseline and final spectral profiles two lesions varying in size according to an exemplary embodiment of the present disclosure.

Following DRS-monitored RF ablation, lesions were fixed and paraffin-embedded prepared for histological examination. In a subset of lesions, OCT imaging was additionally performed in the intact specimen immediately after ablation and prior to sample fixation. Volumetric scans obtained were taken over normal and ablated myocardial tissues to compare microstructural details with DR measurements. A representative RA sample following this workflow is shown in FIGS. 30A-30E. For example, FIG. 30A shows a set of graphs of exemplary baseline spectral profiles (e.g., lines 3005 for lesion s and 3010 for lesion d) and final spectral profiles (e.g., lines 3015 for lesion s and 3020 for lesion d) and real-time lesion depth estimation for two lesions s (line 3025) and d (line 3030) varying in size according to an exemplary embodiment of the present disclosure. In general, untreated sites exhibited a stratified appearance consisting of a thick, well-delineated endocardium and a birefringence band within the myocardium within HROCT. H&E showed a thick elastin and collagen layer with an intact myocardial structure underneath. Trichrome histology correspondingly showed the superposition of collagenous endocardium (blue) over viable myocardium (red). Regions consistent with high DRS-estimated lesion sizes demonstrated markers for treatment and irreversible injury within both HROCT and histology. HROCT images showed evidence of sub-endocardial micro-tears and loss in cellular structure, tissue coagulation indicated by higher myocardial intensity and reduced endocardial differentiation, and the characteristic loss in birefringence band. (See, e.g., Reference 10). Trichrome images showed uniform blue hue within the myocardial layer that became diffusely integrated with red viable myocardium on the lesion boundary. H&E images similarly showed evidence of tissue coagulation at the catheter contact point. In DRS-estimated shallow lesions, HROCT showed similarly the absence of tissue birefringence and superficial coagulation; however micro-tears were not present. H&E and Trichrome images revealed superficial coagulation and loss in viability, respectively.

Exemplary Effect of Irrigation on DRS Measurements

To assess the influence of open in irrigation, a set of eight irrigated transmural lesions were measured using the exemplary optically integrated RFA catheter. (See e.g., FIGS. 31A and 31B). Seven were created with firm contact and one was created with gentle contact. $R_{Rel}$ spectra comparisons with non-irrigated (see, e.g., FIGS. 25A-25F) lesions revealed similar features for the firm contact case, yet less extensive in magnitude. The overall reflectance values were higher across the entire spectral range indicating a strong scattering increase. However, little to no shift in the local minima between 750 nm-800 nm was observed. This can suggest that irrigation can suppress pH changes within the tissue during ablation. Consequently, estimates for lesion depth employing the lesion regression model underestimated actual depths by 52% on average, suggesting that a separate regression model can be used to accommodate such lesions. This result may not quite be unexpected since open irrigation modifies thermal boundary conditions in such a way that protects the catheter contact point and extends damage deeper within the myocardium. In non-irrigated lesions, damage accumulates near the catheter contact point hence there can be greater interaction between the damaged tissue and the optical sampling volume. Nevertheless, all irrigated lesions were successfully classified as ablated. Spectra from lesions that were subject to light contact during irrigation and RF treatment appeared largely like unablated tissue, showing little to no spectral tilt and reflectance decrease. Moreover, extracted values for iMC processing reveal comparable values for concentrations for Mb and MbO and only a slight increase in Mmb content, despite a fairly large lesion size. However, an increase in extracted scattering parameters was still observed. Furthermore, these lesions were often misclassified as normal spectra, further indicating that such lesions can benefit from a separate classifier to reliably determine the injury. Such a method could be based on iMC-derived features since scattering parameters and subtle changes in composition can still be detectable.

Exemplary Discussion

The exemplary results indicate that real-time spectroscopic measurement of absorption-biased diffuse reflectance during application of RF energy has the potential to inform on the extent of thermal injury. (See e.g., FIGS. 28A-30E). Such measurements can be predominantly influenced by changes in the endogenous tissue biochemical composition modified during treatment. Furthermore, a model for lesion size estimation in various chamber tissues has been proposed and validated for rapid on-line monitoring of lesion progression. Current methods for evaluating lesion adequacy rely on the mapping of local electrical activity with concurrent stimulatory provocations to verify voltage abatement. However, with such methods it can be challenging to discriminate permanently damaged tissue from that which has been rendered reversibly unexcitable and functionally inactive in the acute setting. Optical measurements can be sensitive to the underlying biomolecular constituents and tissue architecture, physical parameters directly affected by thermal treatment. (See, e.g., References 25, 26 and 28). Under normal physiological conditions, cardiac tissue can be rich in ferrous myoglobin content and contains trace amounts of the ferric derivative. (See, e.g., References 28 and 29). The application of thermal energy facilitates ferrous to ferric conversions through accelerated oxidation; in this state, these respiratory proteins lose the ability to reversibly bind to oxygen. (See, e.g., References 28 and 29). These biochemical changes influence the spectral morphology of optical measurements sampled at the catheter tip, in particular spectral regions of prominent Mb and Mmb absorption bands. (See, e.g., FIGS. 25A-25F and 29A-31B). The exemplary results indicate that extraction of the indices can be sensitive to these changes and could be used to infer lesion characteristics in situ. (See e.g., FIGS. 28A-30E).

Ascertaining these parameters during ablation treatment could potentially be used in feedback control methods for titrating RF energy dose. Furthermore, permanent tissue damage as judged by coagulative necrosis and loss in cellular structure was observed in microscopic assessment of the lesion core (see e.g., FIGS. 30A-30E) and was consistent with previously reported findings. (See, e.g., References 28 and 30). This suggests that these methods could provide confirmatory measurements that could be implemented together with conventional electroanatomical mapping systems to estimate long-term isolation durability and improve overall procedural efficacy. Although model fitting accuracies in this paper showed good agreement with experimental data (e.g., $R^2 >= 0.95$), most residuals occurred in heavily treated samples near approximately 775 nm and approximately 835 nm. $R_{Rel}$ spectra shown in the exemplary graphs of FIGS. 25A-25F for moderately treated samples exhibited a corresponding local minima in reflectance at approximately 835 nm and an 18 nm red shift and broadening of the minima centered at approximately 758 nm. This observation can be attributed to subtle changes in pH induced by thermal treatment that can have altered the spectral shape of particular cardiac chromophores. Considerable sensitivity of Mmb extinction spectra to changes in pH has been shown. (See, e.g., Reference 27).

In spectrophotometric studies, formation of a broad peak near approximately 835 nm was apparent as pH transitioned from 7.4 to 8.0 and became more pronounced with greater alkalinity. This change was also coupled with considerable reduction in absorption after 860 nm. This observation was consistent with the exemplary measurements of increased reflectance noted after bands>900 nm in atrial samples and >870 nm in ventricular samples. The $LOI_1$ parameter calculations were based on these changes, while further studies can be needed to investigate variations in pH during RF ablation. It can be unlikely that the 2.3 mm source-detector separation employed permits a sampling depth that extends beyond 1-3 mm for the optical properties of ablated tissue. Therefore, the apparent relationship of optically derived parameters to lesions beyond this range can be attributed to proportional changes within the lesion core that correlate with amount of RF energy deposition. This hypothesis can be supported by the classification and regression discrepancies associated with the irrigated ablation lesions which could impel damage away from the catheter contact point. Furthermore, because the method can be sensitive to lesion size, transmurality of measurements may only be ensured when the sampling volume extends beyond the wall and into the pericardial fluid. Consequently, a measurement indicating a lesion size in its current state cannot ensure lesion transmurality without comparing depth to the local wall thickness.

Exemplary Conclusion

An exemplary method for real-time assessment of RFA lesion size in cardiac tissue is described based on thermally induced changes in lesion biochemistry detectable by DRS. These observations have the potential to improve upon current strategies and outcomes with catheter ablation. Direct estimation of lesion size during ablation treatment of AFib could provide useful indication regarding the likelihood of long-term isolation in the acute setting. These findings suggest a framework for rapid monitoring of lesion characteristics in situ using DR spectroscopic methods in the VIS-NIR region.

Provided below are further exemplary aspects of the present disclosure.

Aspect 1. A method for determining a size or a dimension of at least one lesion, comprising receiving first spectra information for the at least one lesion based on an electromagnetic information provided to the at least one lesion; extracting at least one feature related to the at least one lesion from at least one model provided in an electronic storage arrangement; filtering out particular spectra from the first spectra information to generate second spectra information by classifying at least one contact for the at least one lesion; and determining the size or the dimension of the at least one lesion based on the at least one feature, the second spectra information, and a lesion regression model.

Aspect 2. The method of Aspect 1, further comprising generating the first spectra information based on an inverse Monte Carlo procedure.

Aspect 3. The method of Aspect 1, wherein the particular spectra are spectra determined to be unsuitable for a lesion size estimation.

Aspect 4. The method of Aspect 1, wherein the lesion regression model is based on a feature vector that includes lesion optical indices and squares of the lesion optical indices.

Aspect 5. The method of Aspect 4, wherein the spectra determined to be unsuitable for lesion size estimation are determined based on a blood contamination.

Aspect 6. The method of Aspect 1, wherein the generation of the second spectra information is based on a linear discriminant analysis (LDA).

Aspect 7. The method of Aspect 6, further comprising categorizing the second spectra information into one of a non-contact class or a contact class using the LDA.

Aspect 8. The method of Aspect 4, wherein the lesion regression model is further based on a lesion depth of a further lesion.

Aspect 9. A non-transitory computer-accessible medium having stored thereon computer-executable instructions for determining a size or dimension of at least one lesion, wherein, when a computer arrangement executes the instructions, the computer arrangement is configured to perform procedures comprising receiving first spectra information for the at least one lesion based on an electro-magnetic information provided to the at least one lesion; extracting at least one feature related to the at least one lesion from at least one model provided in an electronic storage arrangement; filtering out particular spectra from the first spectra information to generate second spectra information by classifying at least one contact for the at least one lesion; and determining the size or the dimensions of the at least one lesion based on the at least one feature, the second spectra information, and a lesion regression model.

Aspect 10. A system for determining a size or dimension of at least one lesion, comprising a computer hardware arrangement configured to receive first spectra information for the at least one lesion based on an electro-magnetic information provided to the at least one lesion; extract at least one feature related to the at least one lesion from at least one model provided in an electronic storage arrangement; filter out particular spectra from the first spectra information to generate second spectra information by classifying at least one contact for the at least one lesion; and determine the size or the dimensions of the at least one lesion based on the at least one feature, the second spectra information, and a lesion regression model.

Aspect 11. A system for determining a size or a dimension of at least one lesion provided on or in an anatomical structure, comprising an electromagnetic radiation source configured to generate an electromagnetic radiation; a catheter configured to (i) provide the electromagnetic radiation to the at least one lesion, and (i) sample a tissue diffuse reflectance at the at least one lesion that is based on the electromagnetic radiation impacting the at least one lesion; and a computer processing arrangement configured to determine the size or the dimensions of the at least one lesion based on the sampled tissue diffuse reflectance.

Aspect 12. The system of Aspect 11, wherein the electromagnetic radiation source is a broadband light source.

Aspect 13. The system of Aspect 11, further comprising a longpass filter located between the electromagnetic radiation source and the catheter, wherein the longpass filter is configured to filter the electromagnetic radiation.

Exemplary Single Fiber RFA

Figures 32A, 32B:
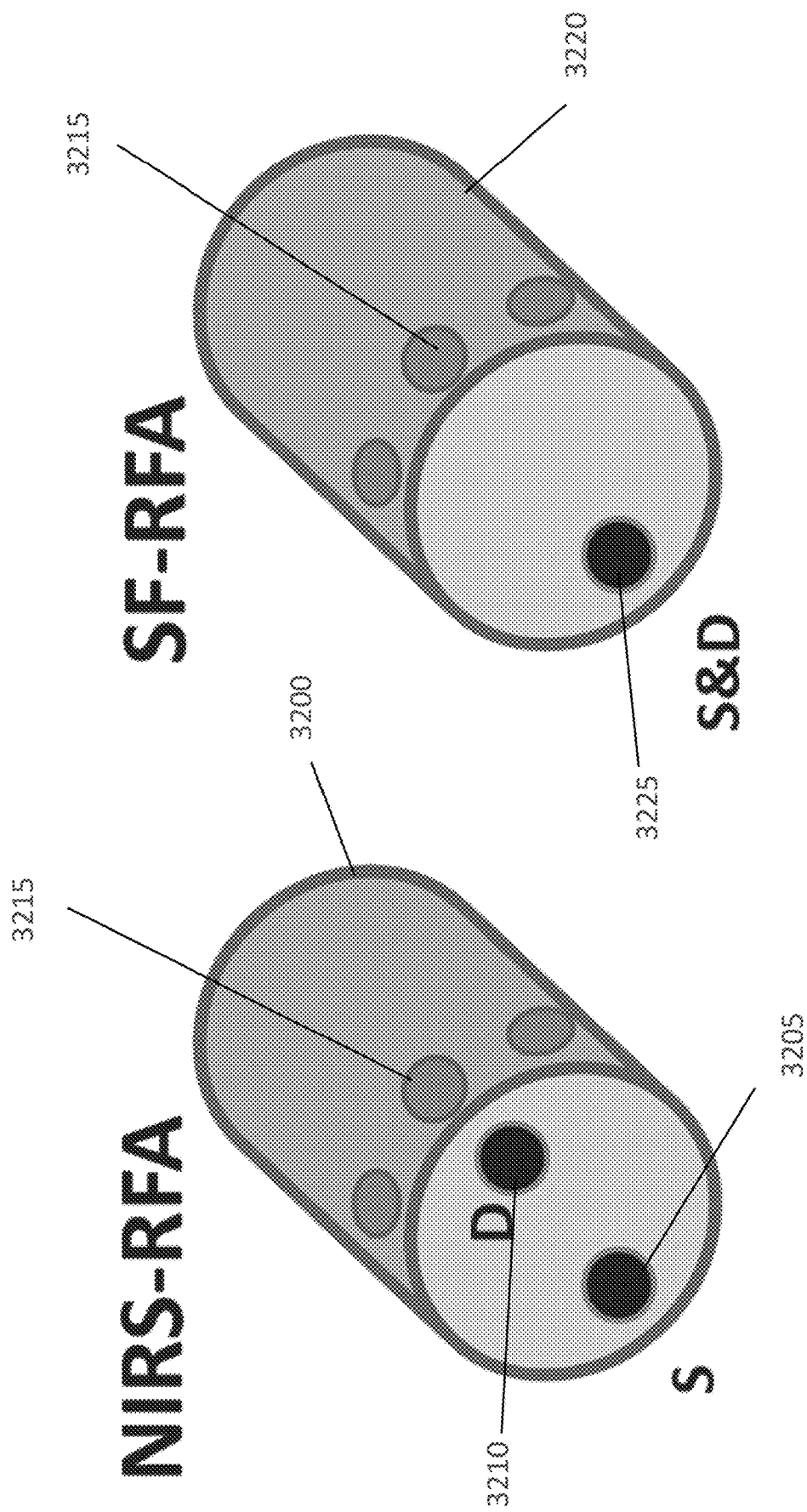
FIG. 32A is an exemplary diagram of the exemplary near-infrared radiofrequency ablation device according to an exemplary embodiment of the present disclosure.
FIG. 32B is an exemplary diagram of the exemplary single-fiber radiofrequency ablation device according to an exemplary embodiment of the present disclosure.

FIG. 32A shows an exemplary diagram of the exemplary Near-Infrared RFA device 3200 according to an exemplary embodiment of the present disclosure. For example, Near-Infrared RFA device 3200 can include a fiber 3205 for near infrared sources and a separate fiber 3210 for detection, as well as multiple irrigation sources 3215. FIG. 32B shows an exemplary diagram of the exemplary Single-Fiber RFA ablation device 3220 according to an exemplary embodiment of the present disclosure. For example, Single-Fiber RFA Ablation device 3220 can also include multiple irrigation sources 3215. Further, instead of separate fibers for the source and detection, Single-Fiber RFA ablation device 3220 can include a single fiber 3225 that can be used for both source and detection. In particular, a single multimode fiber can be used to illuminate the sample. Using the same fiber, the reflected signal can be collected. The reflected signal can be is measured with a camera or photodetector.

Figure 33:
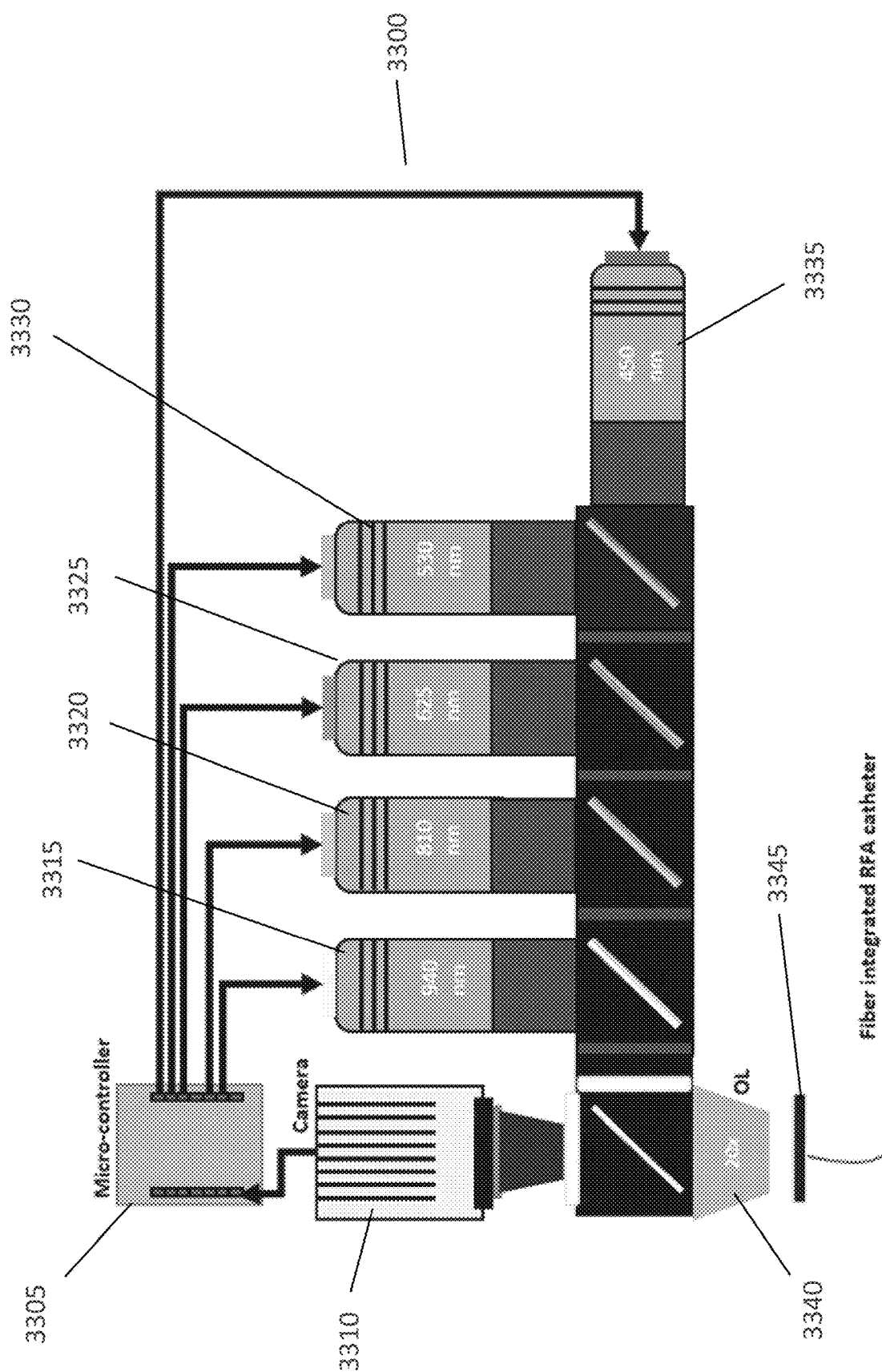
FIG. 33 is an exemplary diagram the exemplary multi-spectral optical system according to an exemplary embodiment of the present disclosure.

FIG. 33 shows an exemplary diagram of the exemplary multispectral optical system according to an exemplary embodiment of the present disclosure. For example, the exemplary multispectral optical system can include a camera 3310, High Power LED sources 3315, 3320, 3325, 3330, 3335, and a microcontroller 3305. A CMOS camera 3310 (e.g., Hamamatsu Flash4.0LT, Hamamatsu City, Japan) can be connected to a communication interface board (e.g., a USB interface board), and can acquire images up to 2048× 2048 pixels. Exemplary software can be used to instruct the camera to capture through an exemplary communication connection (e.g., a USB connection). When camera 3310 is used, a through-the-lens ("TTL") exposure integration time signal can be generated. This can be used to control the timing for each image acquisition. LEDs 3315, 3320, 3325, 3330, and 3335 can be controlled by the TTL signal sent to Microcontroller 3305. At the falling edge of the TTL signal, microcontroller 3305 can switch one or more LEDs to the next LED in the sequence. Objective lens 20× 3340 can be located in camera 3310, and can focus the light on to the single-fiber RFA catheter. The catheter can be connected to a subminiature a ("SMA") fiber adapter 3345.

Figure 34A:
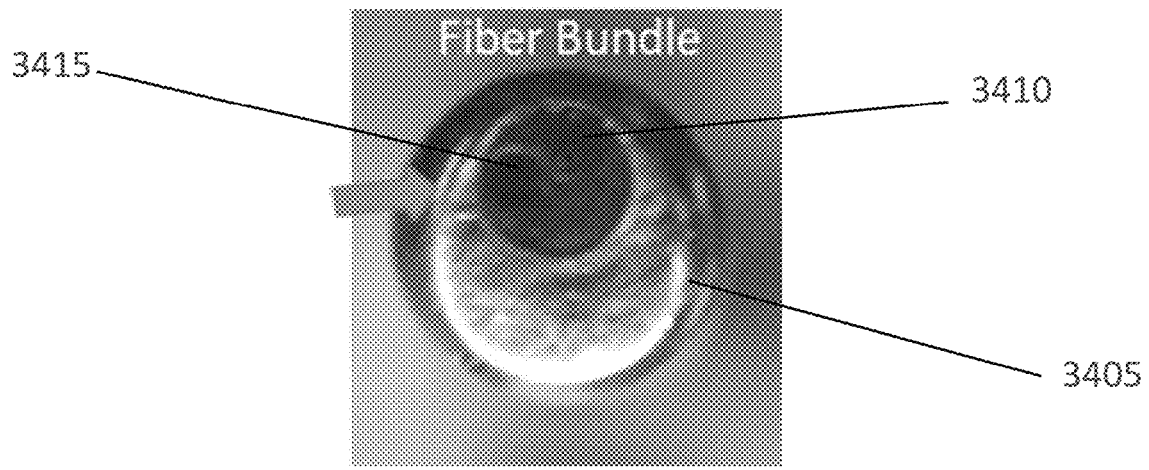
FIG. 34A is an exemplary image of the exemplary near-infrared radiofrequency ablation device with a fiber bundle according to an exemplary embodiment of the present disclosure.
Figure 34B:
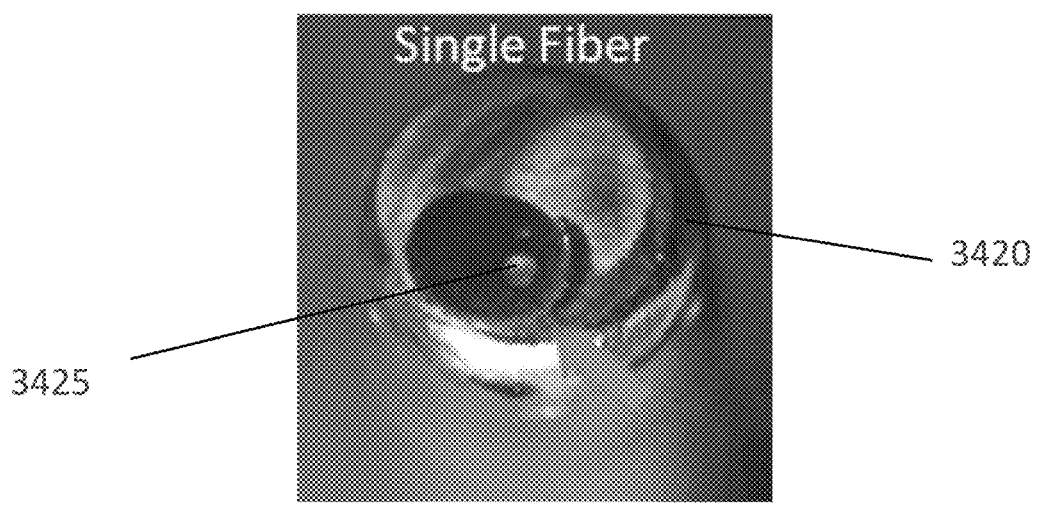
FIG. 34B is an exemplary image of the exemplary single-fiber radiofrequency ablation device according to an exemplary embodiment of the present disclosure.

FIG. 34A shows an exemplary image of an exemplary Near-Infrared RFA device 3405 having separate fibers 3410 and 3415 to be used as or in conjunction with source and detection, according to an exemplary embodiment of the present disclosure. FIG. 34B shows an exemplary image of an exemplary Single-Fiber RFA device 3420 having a single fiber 3420 to be used as or in conjunction with source and detection, according to another exemplary embodiment of the present disclosure.

Figure 35:
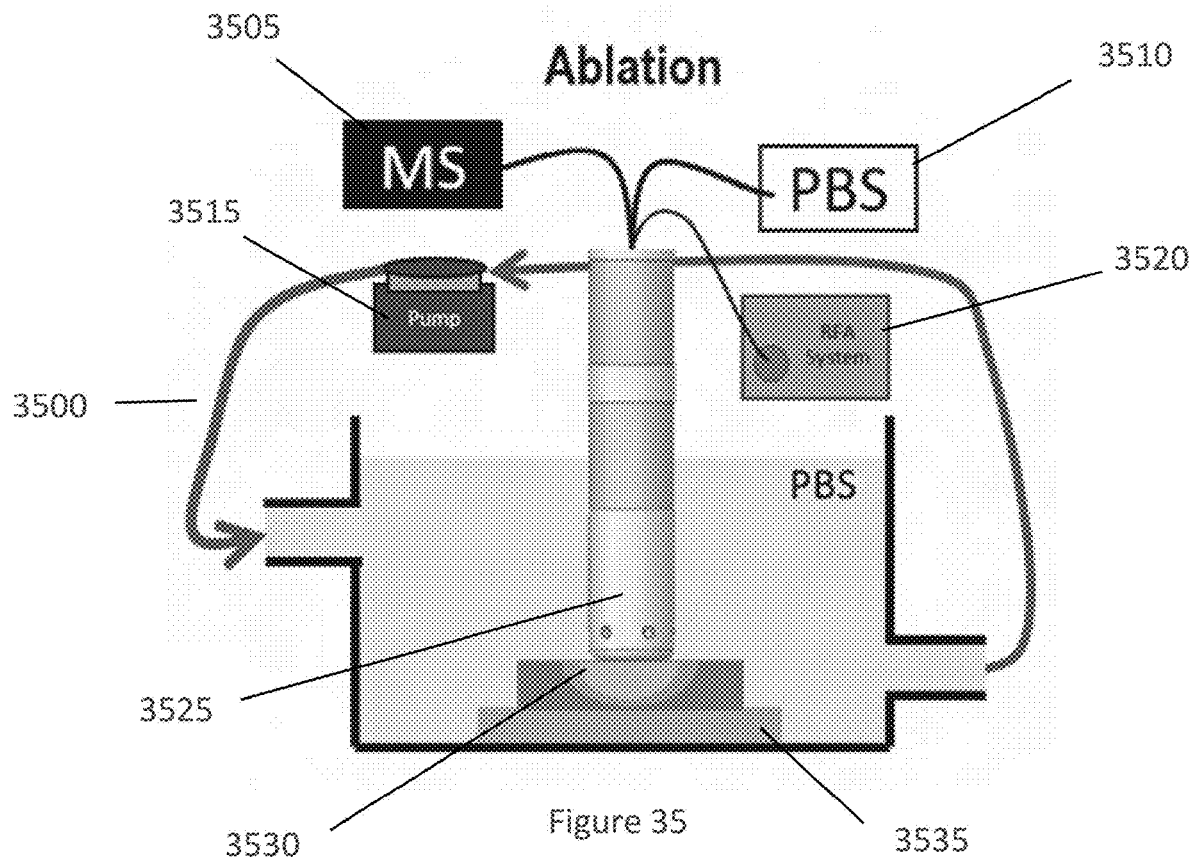
FIG. 35 is an exemplary diagram of an exemplary experiment performed using the exemplary ablation device according to an exemplary embodiment of the present disclosure.

FIG. 35 shows an exemplary diagram of an exemplary experiment performed using the exemplary ablation device according to an exemplary embodiment of the present disclosure. In particular, the exemplary experiment includes a dissected heart chamber 3530 placed in a temperature-maintained phosphate buffered saline ("PBS") bath at 37° C. and laid flat on top of cork board 3535. The PBS bath can be attached to perfusion pump 3515 by a tube 3500 to generate a circulating and pulsatile flow. A set of irrigated lesions were delivered on to a heart tissue 3530 using the exemplary fiber-integrated RFA catheter 3525 and a generator 3520 (e.g., Stockert 70, Biosense Webster, Diamond Bar, CA). The exemplary RFA catheter was connected to an exemplary optical system 3505 as well to irrigation pump 3510 (e.g., BiosenseWebster coolflow pump). The flow rate was fixed at 10 ml/min.

Figure 36:
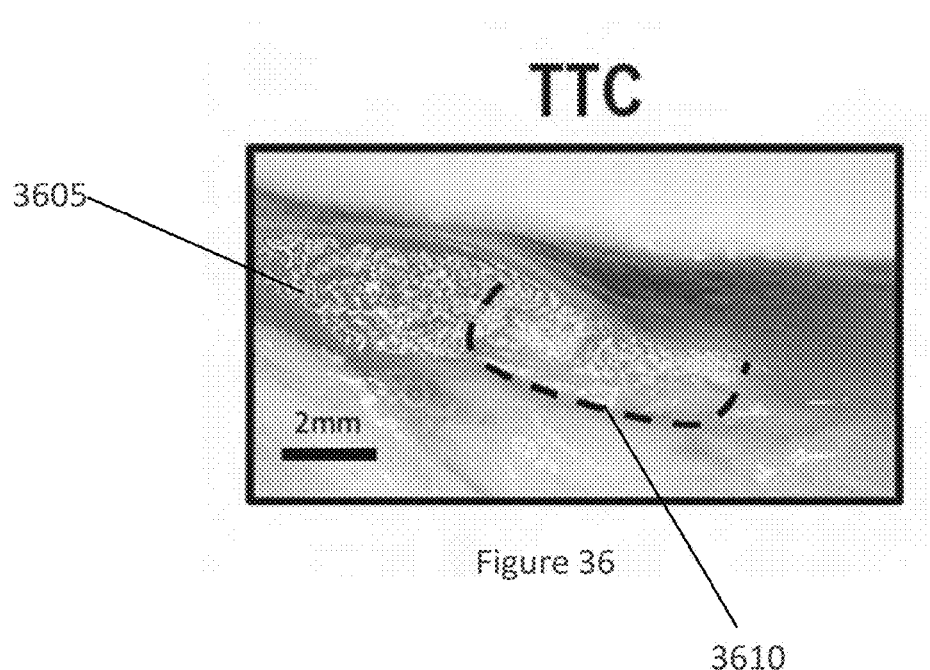
FIG. 36 is an exemplary image of tissue having an ablation procedure performed thereon according to an exemplary embodiment of the present disclosure.

FIG. 36 illustrates an exemplary image of the tissue having an ablation procedure performed thereon according to an exemplary embodiment of the present disclosure. After the exemplary ablation experiment was performed, the sample was submerged in 1% TTC vital stain for 60 minutes. The TTC was used to stain normal tissue in bright red and revealed damaged tissue 3605, and thus also illustrating an undamaged tissue 3610.

Figure 37A:
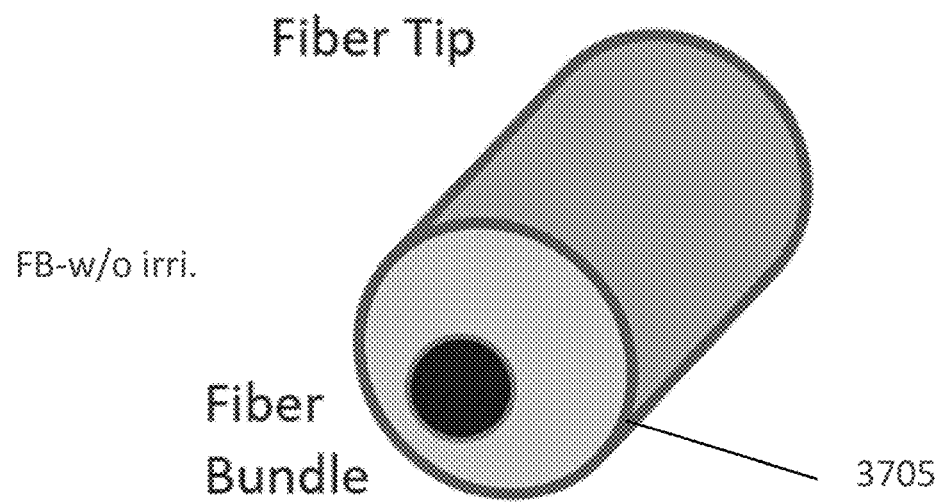
FIG. 37A is an exemplary diagram of the exemplary radiofrequency ablation device without irrigation according to an exemplary embodiment of the present disclosure.
Figure 37B:
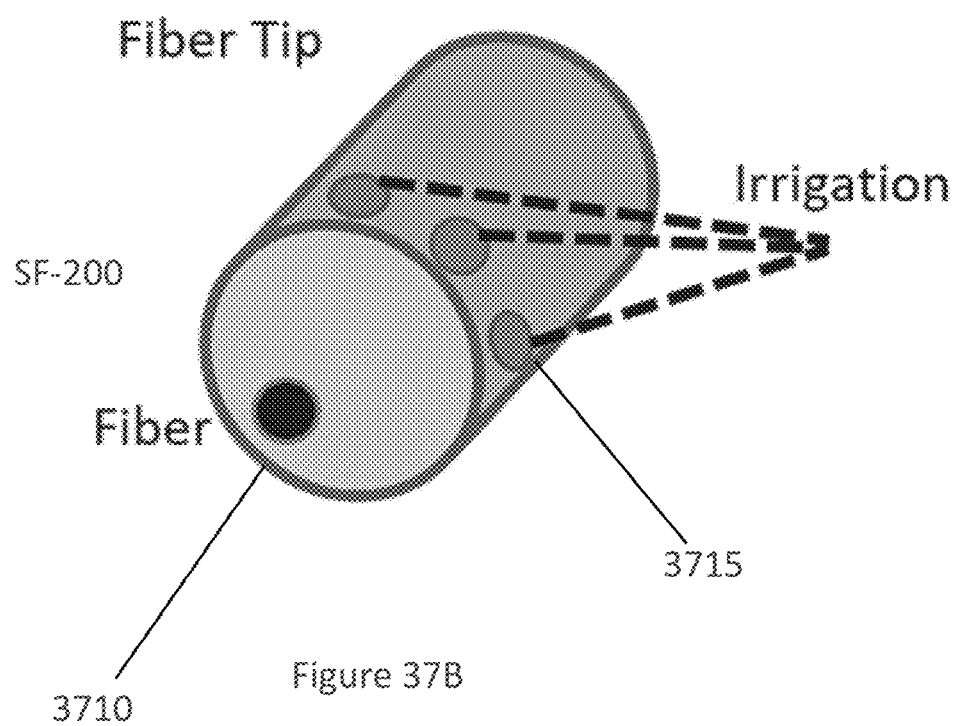
FIG. 37B is an exemplary diagram of the exemplary single-fiber radiofrequency ablation device with irrigation according to an exemplary embodiment of the present disclosure.
Figure 38:
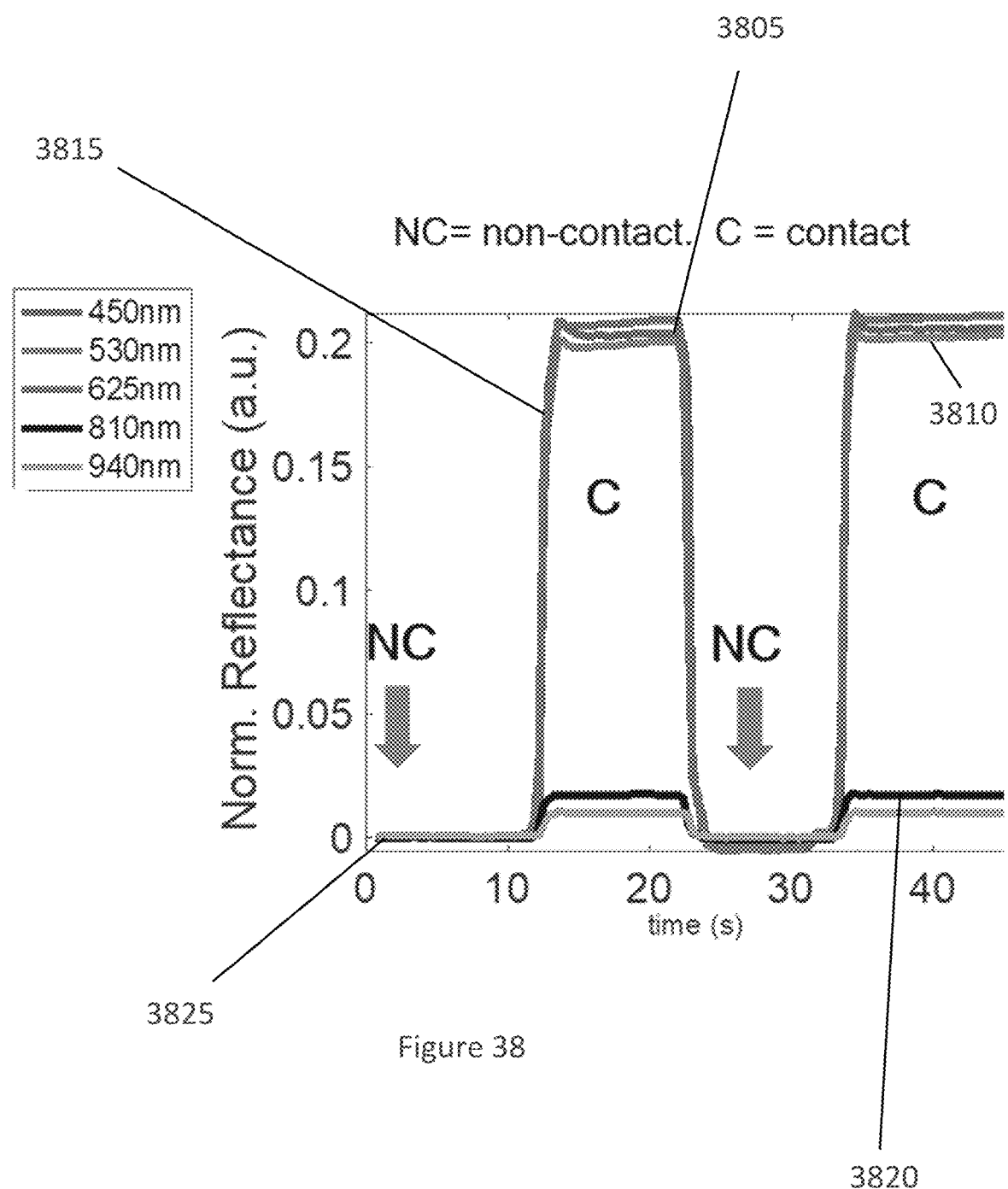
FIG. 38 is an exemplary graph illustrating a fiber-bundle contact assessment according to an exemplary embodiment of the present disclosure.

FIG. 37A shows an exemplary diagram of an exemplary radiofrequency ablation device 3705 without irrigation according to an exemplary embodiment of the present disclosure. FIG. 37B illustrates an exemplary diagram of the exemplary single-fiber RFA device 3410 that includes multiple irrigation sources 3715 according to an exemplary embodiment of the present disclosure;

FIG. 38 shows an exemplary graph illustrating fiber-bundle contact assessment according to an exemplary embodiment of the present disclosure. In particular, the graph shows contact assessment of fiber-bundle integrated RFA catheter for Forty-five second acquisition at 450 nm (e.g., shown by line 3805), 530 nm (e.g., shown by line 3810), 625 nm (e.g., shown by line 3815), 810 nm (e.g., shown by line 3820), and 940 nm (e.g., shown by line 3825). The catheter floated in PBS, and made contact with tissue. This was repeated twice. The reflectance values at individual wavelength channels were normalized by intensity values floating in PBS. At 450 nm, 530 nm, and 625 nm, a transition from non-contact to contact can be seen. However, this transition is not as apparent at 810 nm and 940 nm.

FIGS. 39A-39F show exemplary graphs illustrating fiber-bundle ablation assessment and an exemplary image showing ablated tissue according to an exemplary embodiment of the present disclosure. Each graph shows ablation assessment of the exemplary fiber-bundle integrated RFA catheter. A swine right ventricle was ablated for 40 seconds with power set at 20 W. Ablation began 10 seconds into the acquisition. At all wavelengths, normalized reflectance increased during ablation. Relative to shorter wavelengths, normalized reflectance at 810 nm (see e.g., FIG. 39E) and 940 nm (see e.g., FIG. 39F) show less increase after ablation. At 450 nm (see e.g., FIG. 39A), 530 nm (see e.g., FIG. 39B), and 625 nm (see e.g., FIG. 39C), normalized reflectance increased at larger slopes during the first 20 seconds. Reflectance plateaued until ablation was finished. The corresponding ablated tissue 3905 after TTC staining is shown in FIG. 39D.

Figure 40:
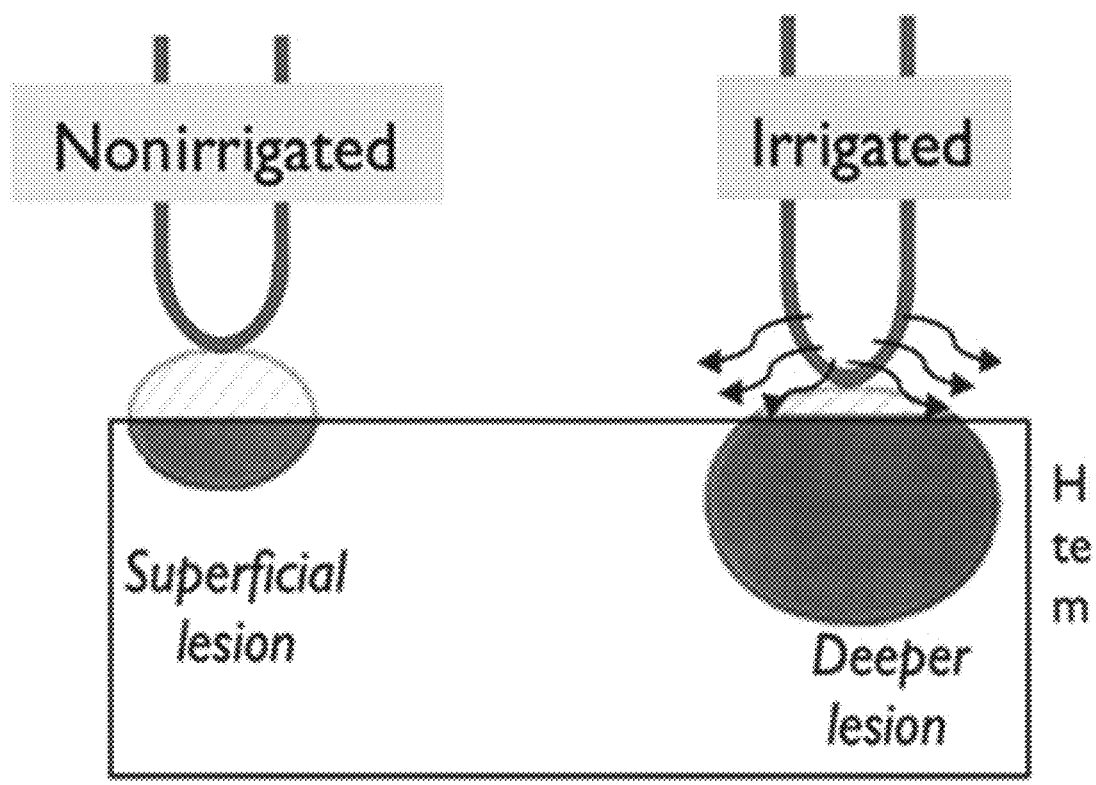
FIG. 40 is a diagram illustrating a comparison between irrigated and non-irrigated lesions according to an exemplary embodiment of the present disclosure.

FIG. 40 shows an exemplary diagram illustrating a comparison between irrigated and non-irrigated lesions according to an exemplary embodiment of the present disclosure. As shown in FIG. 40, non-irrigated ablations are mostly superficial. However, irrigated ablations can generate deeper lesions since the surface can be cooled by saline. This can facilitate higher power and longer duration without coagulum formation. The exemplary irradiated ablation can also reduce steam-pop incidence since the temperature of tissue can be lower.

Figure 41:
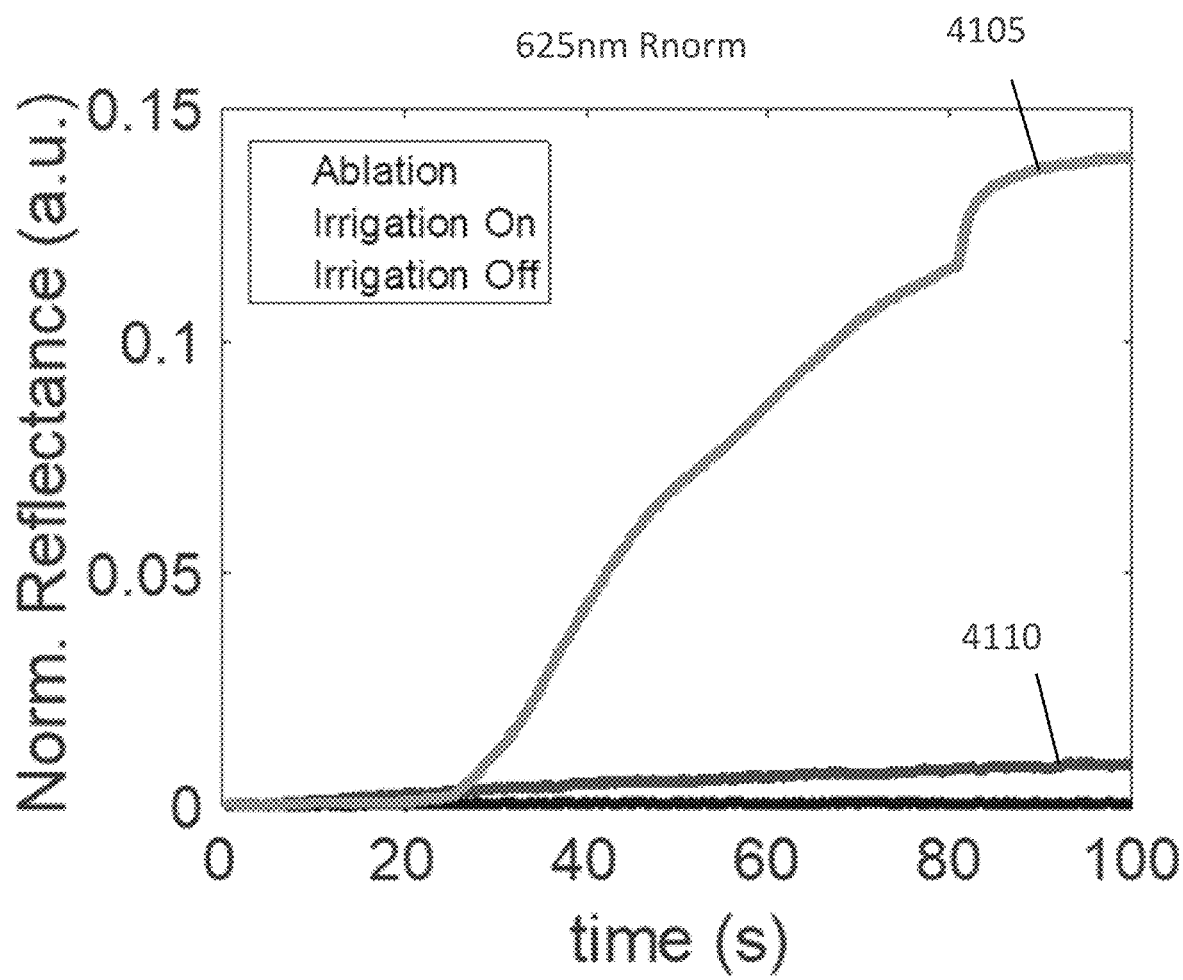
FIG. 41 is an exemplary graph illustrating a reflectance comparison according to an exemplary embodiment of the present disclosure.

FIG. 41 shows an exemplary graph illustrating a 625 nm normalized reflectance comparison of controlled measurements using an irrigated and a non-irrigated single-fiber integrated RFA catheter. The Single-fiber catheter can be smaller in diameter compared to fiber-bundle, which can facilitate easier integration and better durability. Since 625 nm has the strongest signal, a 100 s acquisition of irrigation on, off, and ablation for 60 s with irrigation on is shown. Normalized reflectance rises slightly with irrigation over time. When tissue is ablated, a difference between when catheter is ablating on tissue and when catheter is in contact with irrigation can be seen. When irrigation is off, normalized reflectance is constant at zero.

Figure 42:
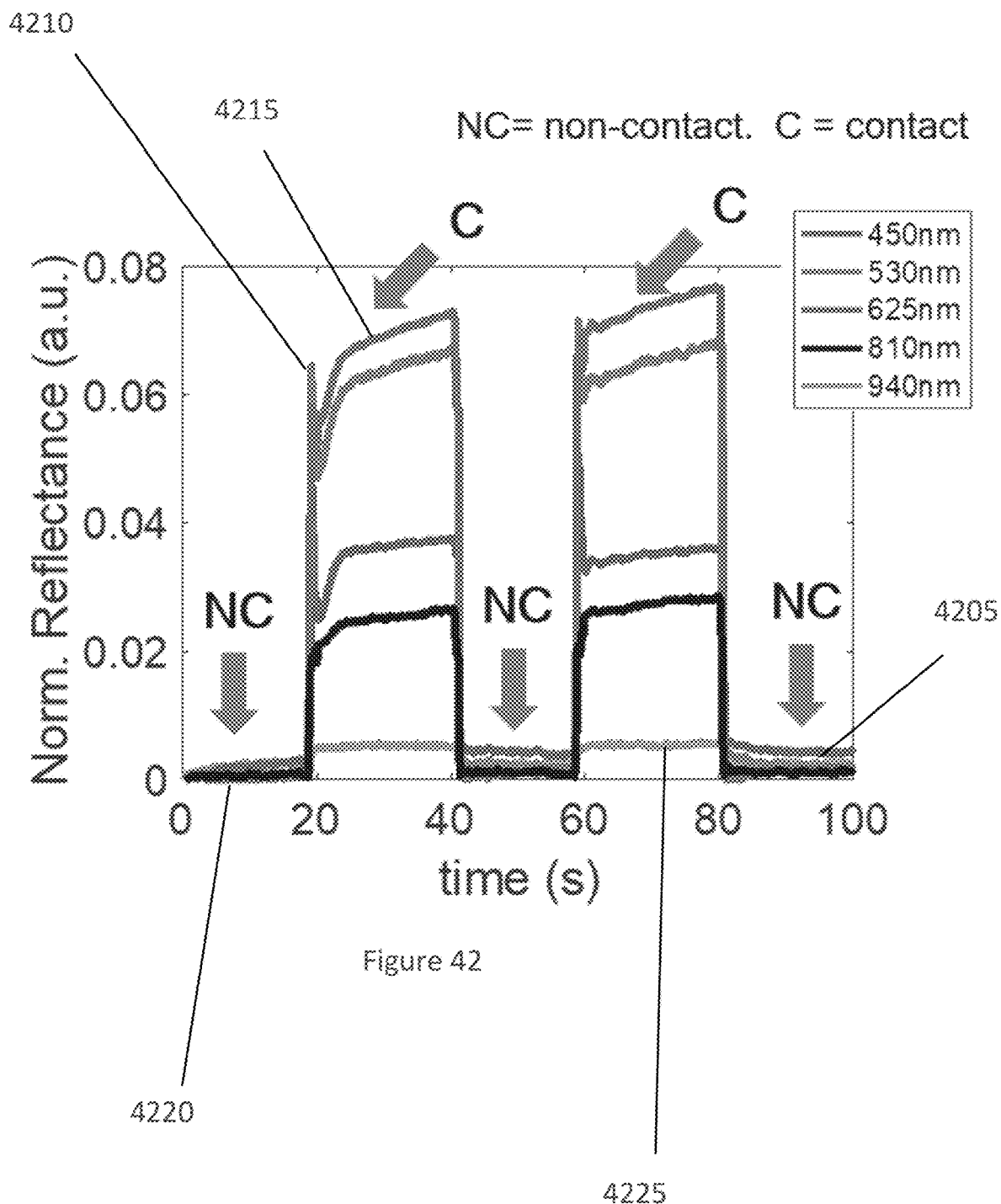
FIG. 42 is an exemplary graph illustrating a contact assessment for the exemplary single-fiber radiofrequency ablation system according to an exemplary embodiment of the present disclosure.

FIG. 42 shows an exemplary graph illustrating contact assessment for 450 nm (e.g., shown by line 4205), 530 nm (e.g., shown by line 4210), 625 nm (e.g., shown by line 4215), 810 nm (e.g., shown by line 4220), and 940 nm (e.g., shown by line 4225) for 100 s. At 20 s intervals, catheters transitioned from non-contact (e.g., floating in PBS) to contact (e.g., contact with tissue). At all wavelengths, normalized reflectance increased when in contact with tissue. When irrigation is on, a gradual increase in all wavelengths during contact can be seen.

Figure 43:
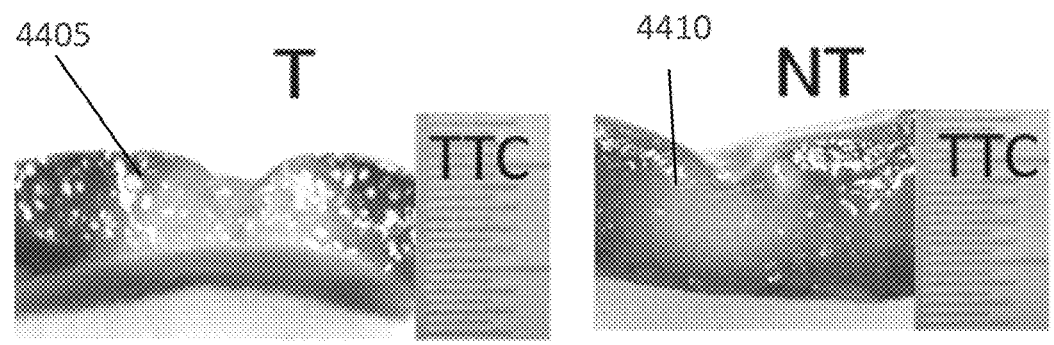
FIG. 43 is a set of exemplary images of transmural and non-transmural lesions according to an exemplary embodiment of the present disclosure.

FIG. 43 illustrates a set of exemplary images of a TTC-stained transmural (e.g., lesion 4405) and a TTC-stained non-transmural lesion (e.g., lesion 4410) according to an exemplary embodiment of the present disclosure.

Figure 44:
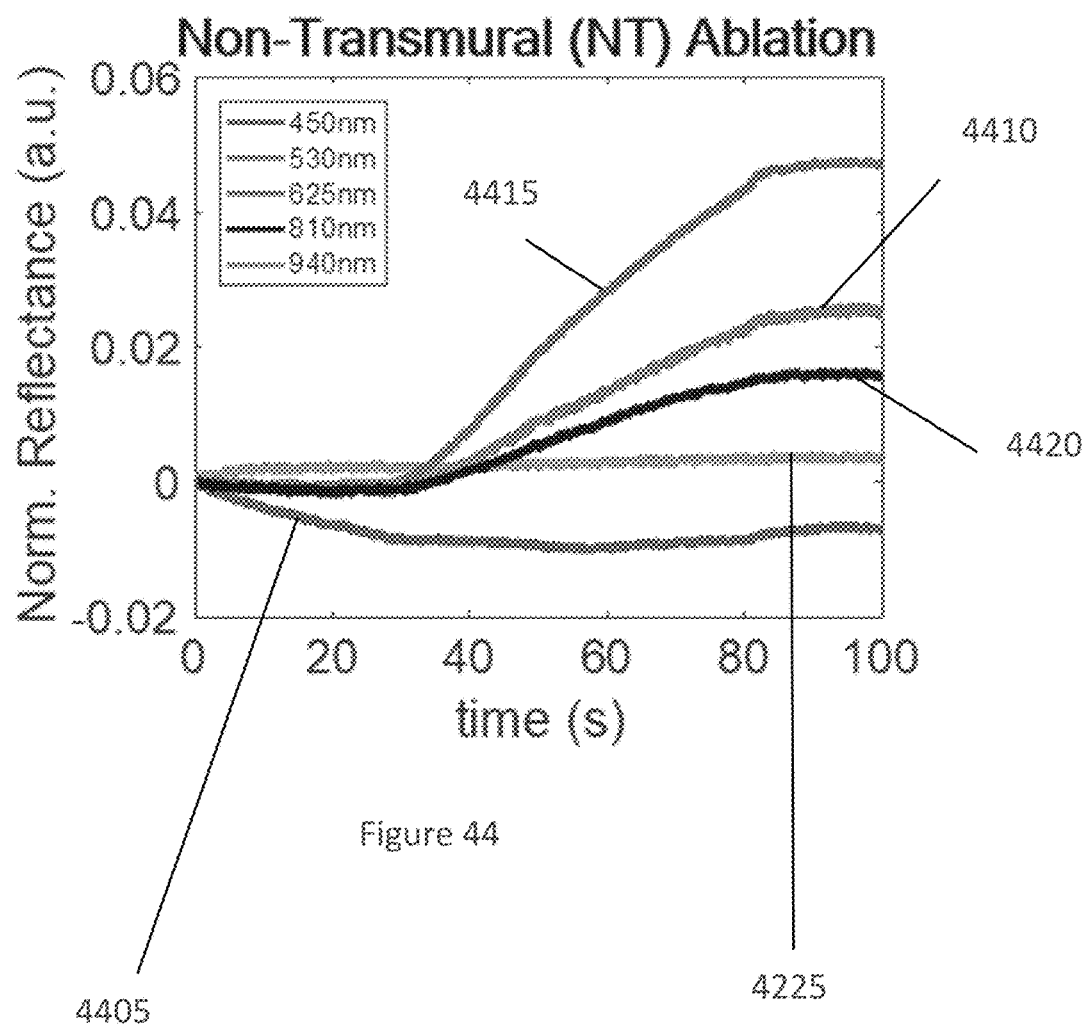
FIG. 44 is an exemplary graph illustrating exemplary results from the non-transmural ablation according to an exemplary embodiment of the present disclosure.

FIG. 44 shows an exemplary graph illustrating results from non-transmural ablation according to an exemplary embodiment of the present disclosure. A swine right ventricle ("RV") was ablated for 60 seconds at 25 W with a flow rate 10 ml/min. Total acquisition time was 100 s with ablation beginning at 20 s. In a non-transmural lesion, normalized reflectance at 450 nm (e.g., shown by line 4405), 530 nm (e.g., shown by line 4410), 625 nm (e.g., shown by line 4415), 810 nm (e.g., shown by line 4420), and 940 nm (e.g., shown by line 4425) began to increase 10 seconds into ablation. The relative increase was small at all wavelengths (e.g., less than 0.05).

Figure 45:
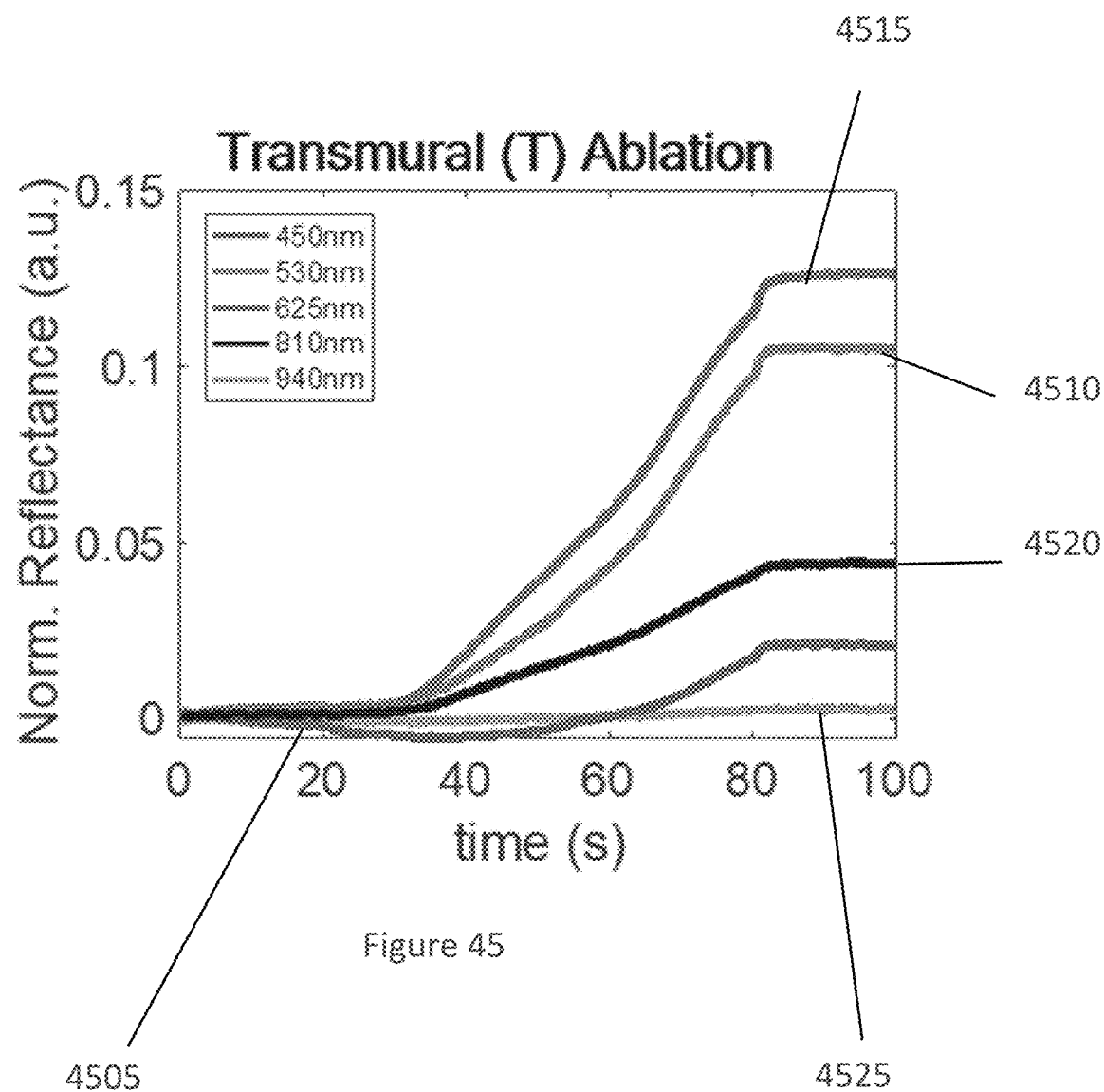
FIG. 45 is an exemplary graph illustrating exemplary results from the transmural ablation according to an exemplary embodiment of the present disclosure.
Figure 46A:
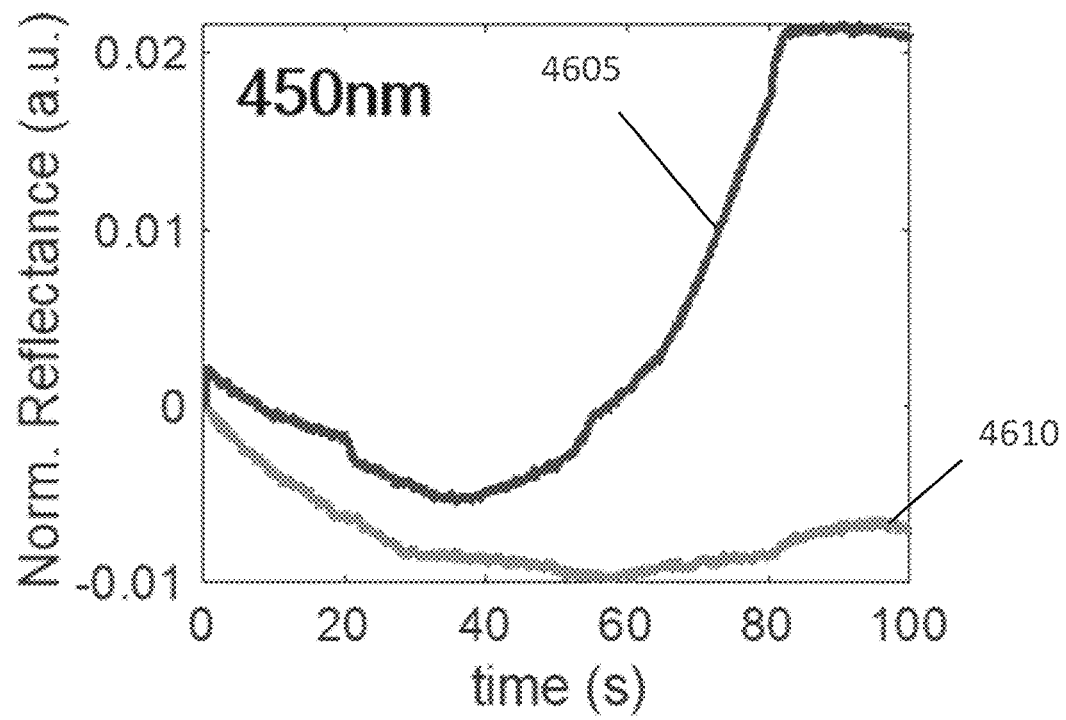
FIGS. 46A-46D are exemplary graphs illustrating comparisons between transmural and non-transmural lesions at individual wavelengths according to an exemplary embodiment of the present disclosure.
Figure 46B:
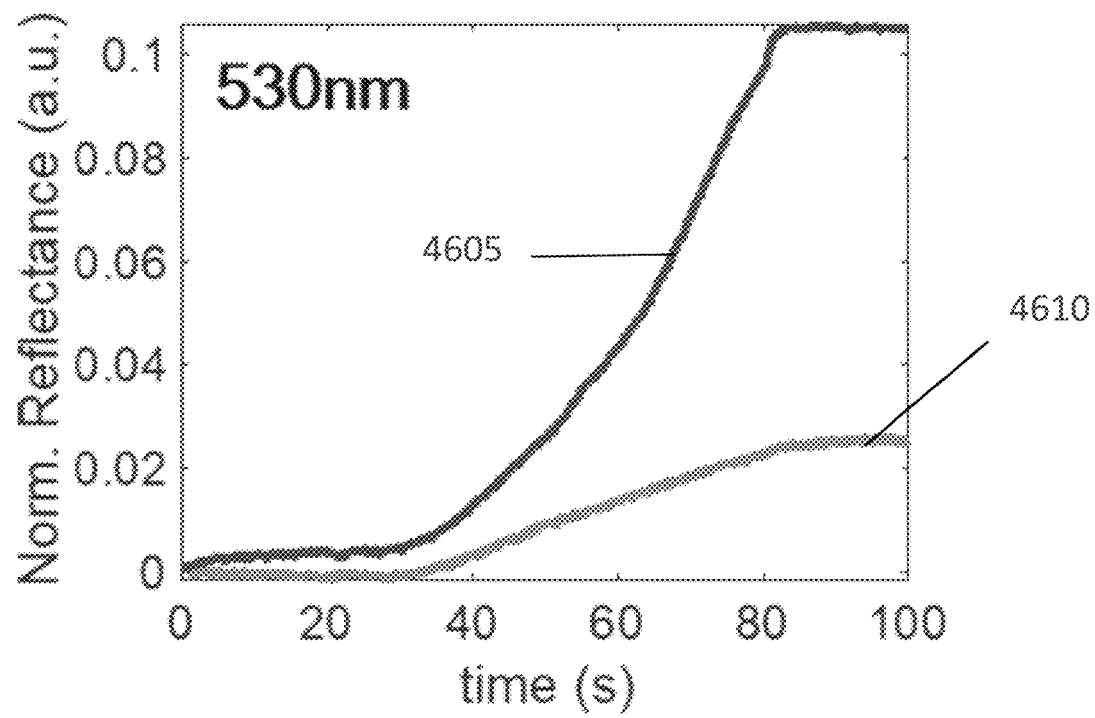
Figure 46C:
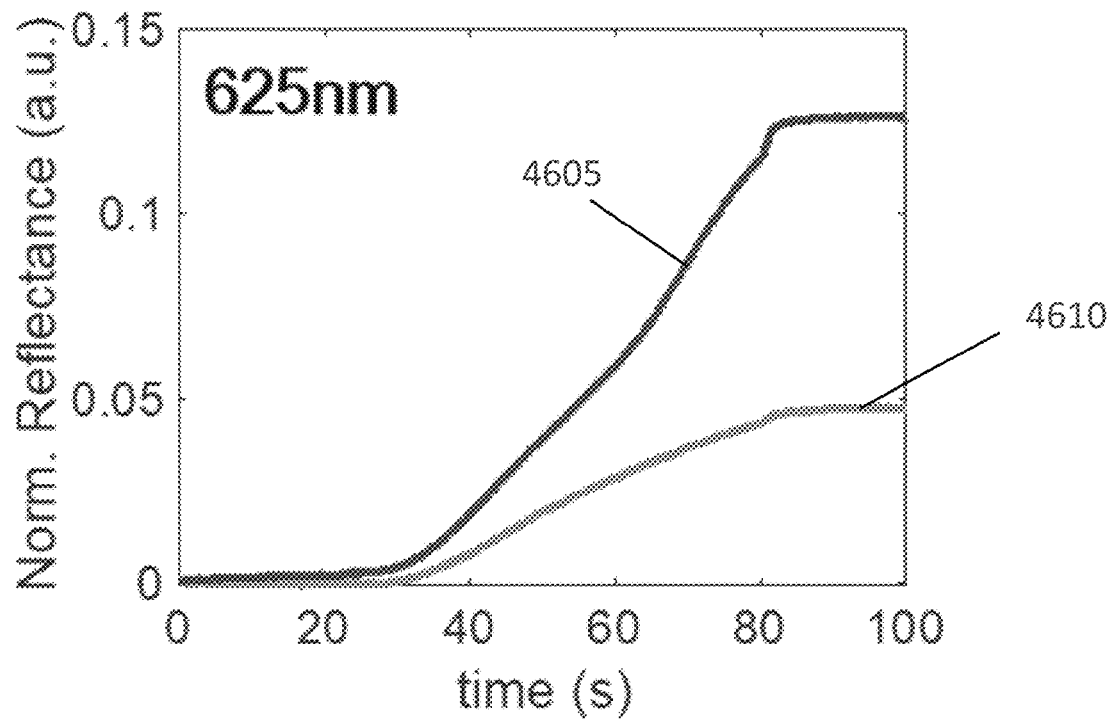
Figure 46D:
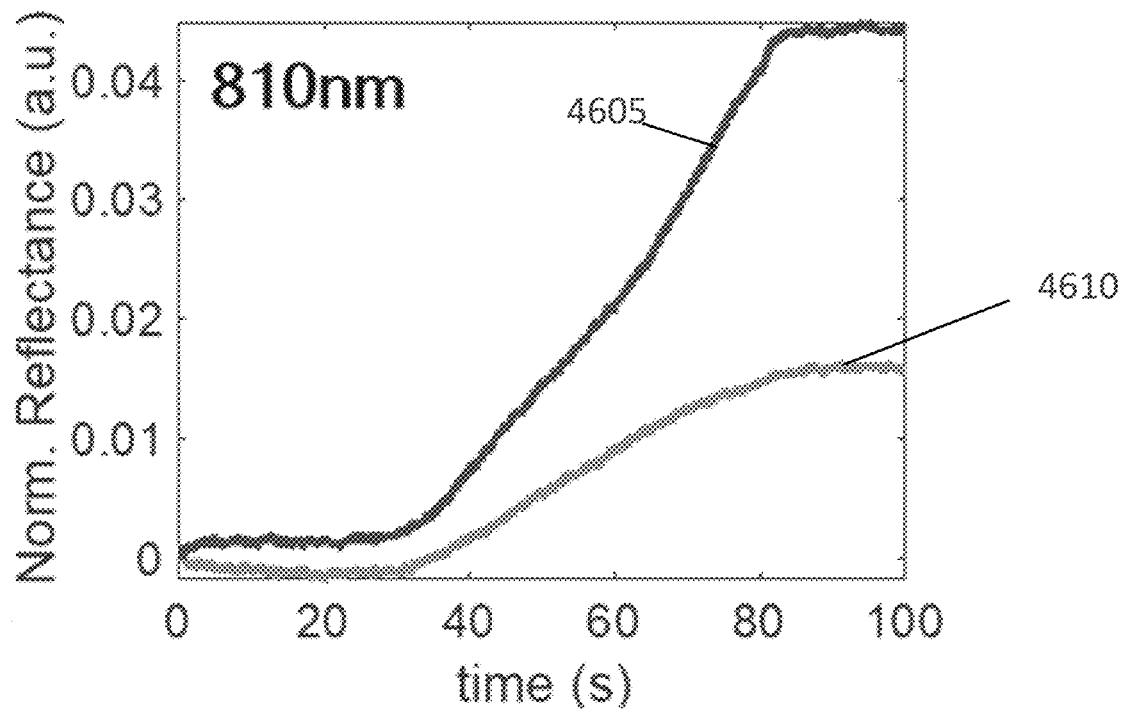

FIG. 45 shows an exemplary graph illustrating results from transmural ablation for 450 nm (e.g., shown by line 4505), 530 nm (e.g., shown by line 4510), 625 nm (e.g., shown by line 4515), 810 nm (e.g., shown by line 4520), and 940 nm (e.g., shown by line 4525) according to an exemplary embodiment of the present disclosure. Compared to non-transmural ablation, transmural lesions show higher normalized reflectance value at the end of ablation. Reflectance almost triples that of non-transmural lesions. Although the depth of both lesions are similar, reflectance measurements are different.

FIGS. 46A-46D show exemplary graphs illustrating comparisons between transmural and non-transmural lesions at individual wavelengths according to an exemplary embodiment of the present disclosure. In particular, FIGS. 46A-46D show direct comparison between transmural lesions (e.g., lines 4605) and non-transmural lesions (e.g., lines 4610) at individual wavelengths.

Figure 47:
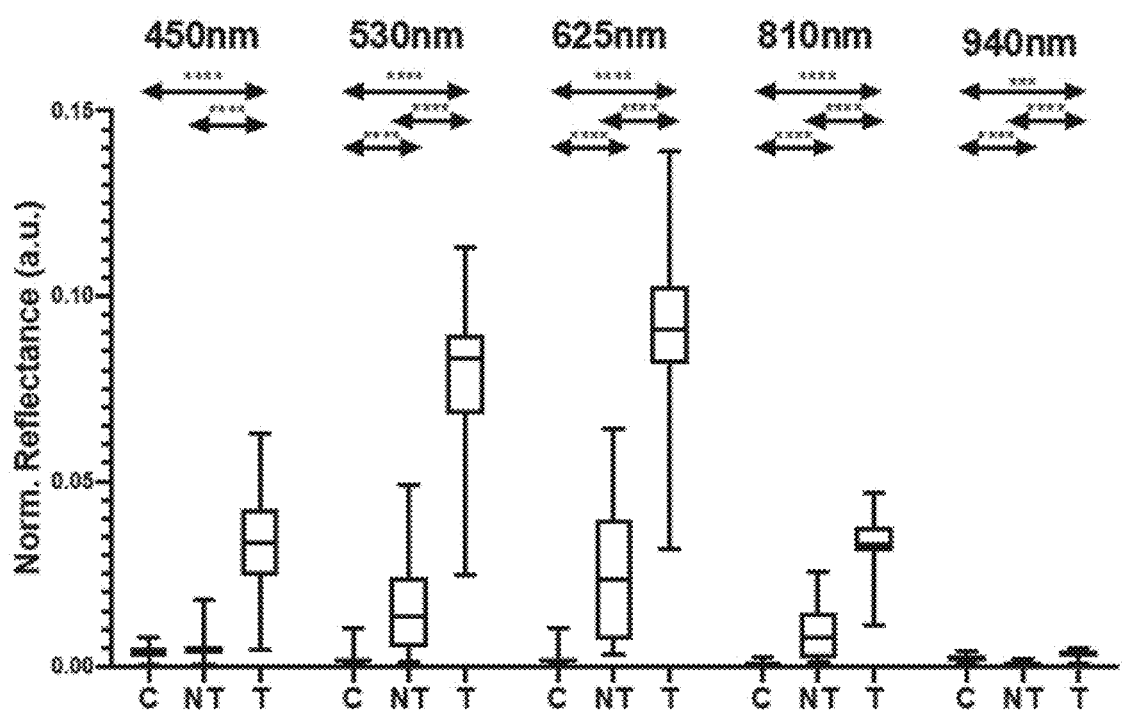
FIG. 47 is an exemplary graph illustrating an analysis of variance analysis between control, non-transmural, and transmural lesions according to an exemplary embodiment of the present disclosure.

FIG. 47 shows an exemplary graph illustrating an analysis of variance ("ANOVA") analysis between control, non-transmural, and transmural lesions according to an exemplary embodiment of the present disclosure (e.g., with a total of 36 non-transmural lesions and 16 transmural lesions). Transmural and non-transmural lesions can be highly discriminatory at all wavelengths (e.g., P<0.0001). The use of, for example, all wavelengths, except 450 nm, show that control, non-transmural and transmural lesions can be discriminatory.

Figure 48A:
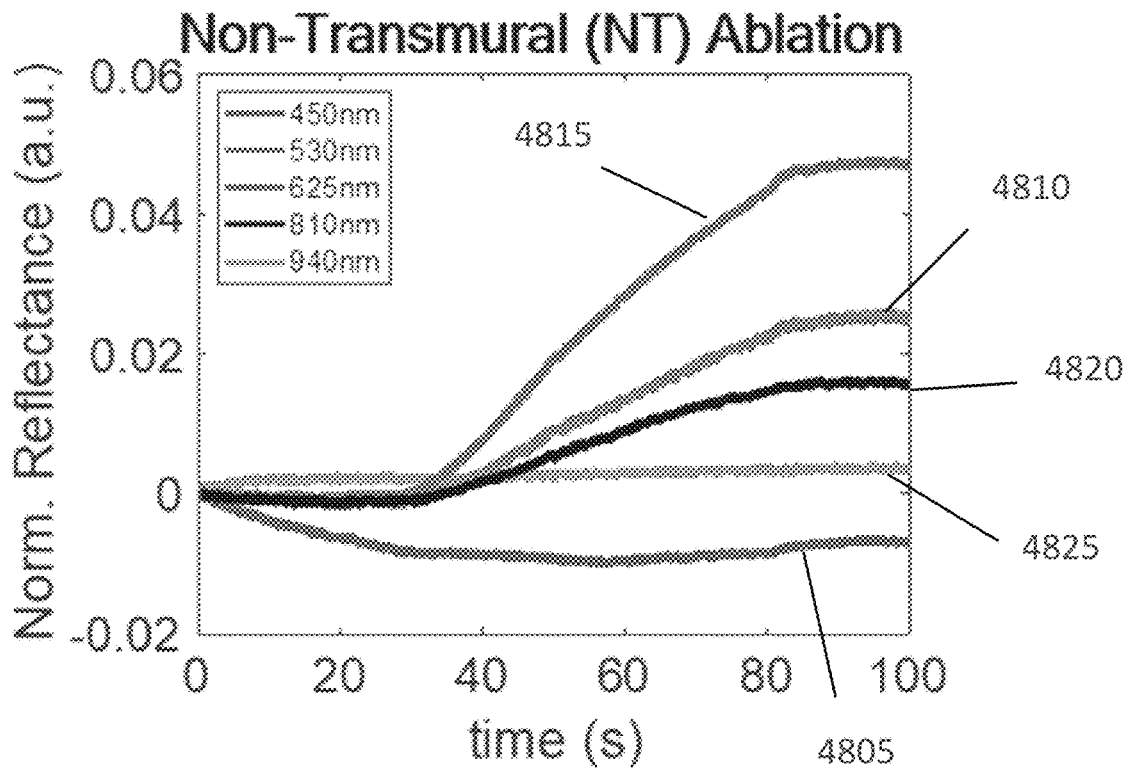
FIG. 48A is an exemplary graph illustrating the non-transmural ablation at different wavelengths according to an exemplary embodiment of the present disclosure.

FIG. 48A shows an exemplary graph illustrating non-transmural ablation at different wavelengths according to an exemplary embodiment of the present disclosure. The ablation generator was on for 60 seconds, which resulted in a non-transmural lesion. Normalized reflectance measurements increased during ablation energy delivery.

Figure 48B:
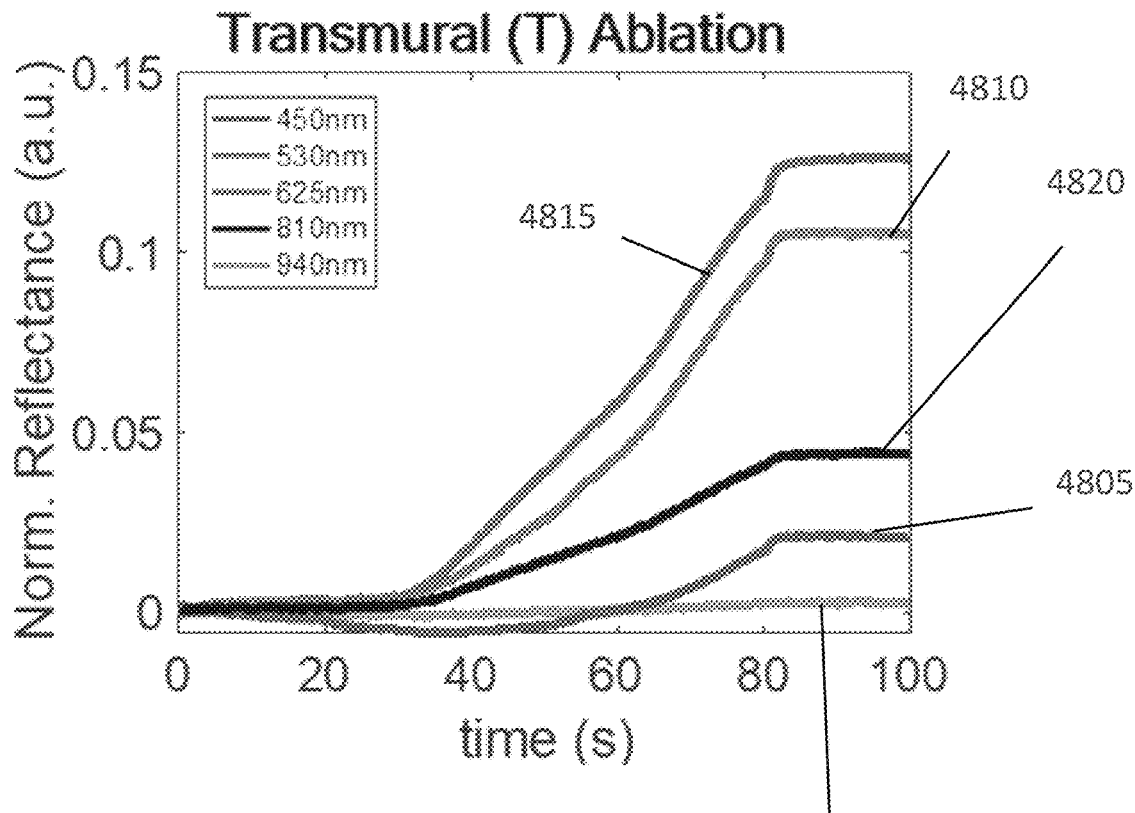
FIG. 48B is an exemplary graph illustrating the transmural ablation at different wavelengths according to an exemplary embodiment of the present disclosure.

FIG. 48B shows an exemplary graph illustrating transmural ablation at different wavelengths according to an exemplary embodiment of the present disclosure. The ablation generator was on for 60 seconds, which resulted in a transmural lesion. Normalized reflectance measurements increased during ablation energy delivery. The increase in normalized reflectance was observed to be higher within transmural lesions compared to non-transmural lesions.

Figure 49:
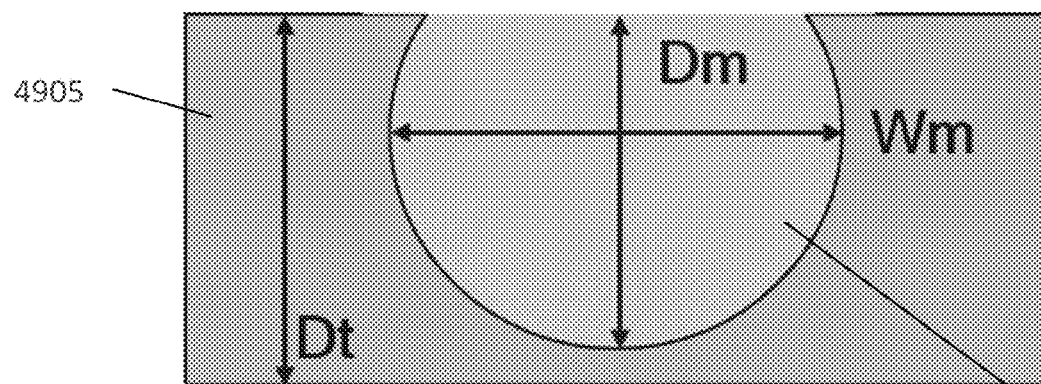
FIG. 49 is an exemplary diagram illustrating a lesion dimension analysis according to an exemplary embodiment of the present disclosure.

FIG. 49 shows an exemplary diagram illustrating an exemplary lesion dimension analysis according to an exemplary embodiment of the present disclosure. Effective treatment can be directly related to lesion characteristics (e.g., continuity and transmurality). Small gaps in ablation lines can setup a substrate that can support unwanted electrical activity. Therefore, lesion width can be beneficial to know when generating continuous ablation lines. Additionally, since depth can vary in all areas of the heart, an analysis of lesion depth compared to total depth of tissue can be more beneficial than absolute lesion depth. Depth percentage was analyzed by comparing how deep Ablated Tissue 4910 is with respect to Total Myocardial Tissue Depth 4905.

Figure 50:
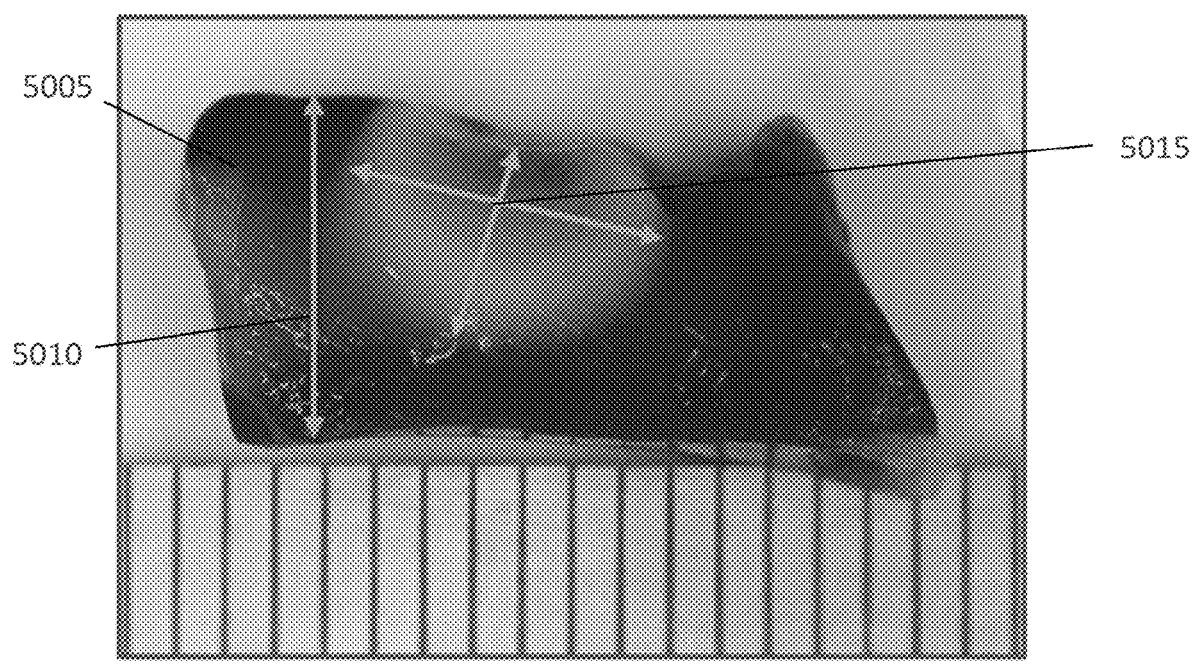
FIG. 50 is an exemplary image of exemplary extraction parameters using a triphenyl-2H-tetrazolium chloride stained tissue according to an exemplary embodiment of the present disclosure.

FIG. 50 illustrates an exemplary image of extraction parameters using TTC stained tissue according to an exemplary embodiment of the present disclosure. In particular, FIG. 50 shows Max Depth 5115, Total Myocardial Depth 5010, and Myocardial Tissue 5005.

FIGS. 51A-51F show an exemplary image and graphs illustrating a width analysis for non-transmural and transmural ablation according to an exemplary embodiment of the present disclosure. Normalized reflectance at the end of acquisition was plotted against maximum width in a scatter plot. A correlation coefficient was computed for each of the wavelengths to determine the linear relationship between normalized reflectance and the width of ablated tissue. All correlation coefficients were above 0.5 at all wavelengths. Transmural lesions (e.g., represented by dots 5115) and non-transmural lesions (e.g., represented by dots 5120) were well discriminated in two separate clusters. The highest correlation coefficient was in data acquired at 810 nm and 625 nm. FIG. 51A shows ablated myocardium 5105 and a Maximum Width measurement 5110.

FIGS. 52A-42F show an exemplary image and graphs illustrating a depth analysis for non-transmural and transmural ablation according to an exemplary embodiment of the present disclosure. Compared to the width analysis, the depth analysis showed higher correlation coefficients with 530 nm, 625 nm, and 810 nm all above 0.8. At all wavelengths, there exists a distinction between transmural lesions (e.g., represented by dots 5215) and non-transmural lesions (e.g., represented by dots 5220). FIG. 52A shown TTC Stained Myocardium 5205, Maximum Lesion Depth 5210, and Total Myocardium Depth 5215.

FIG. 53A-53E show exemplary image and graphs illustrating a steam-pop analysis according to an exemplary embodiment of the present disclosure. Excessive heating of tissue surface can rupture due to steam produced beneath the endocardial tissue surface, which can be referred to as steam-pops. This can cause superficial craters or tissue ruptures. Tissue ruptures can be seen in FIG. 53A shown by elements 5305 and 5310. FIG. 53B shows transmural ablation plotted over time. Normalized reflectance increases at a fast rate until it stabilizes during ablation. This phenomenon is shown in most transmural ablations at 450 nm (e.g., shown by line 5305), 530 nm (e.g., shown by line 5310), 625 nm (e.g., shown by line 5315), 810 nm (e.g., shown by line 5320), and 940 nm (e.g., shown by line 5325).

Three individual steam-pop cases are shown in FIGS. 53C-53E. Rapid increase in all wavelengths occurs in the first 20 seconds into ablation. When normalized reflectance reaches its peak in all wavelengths, the signal begins to gradually decrease until steam pop occurs. After steam-pop incidence, the signal jitters until ablation is turned off. This parabolic shape before steam-pop occur can be a precursor to prevent excessive heating of lesions.

Figure 54:
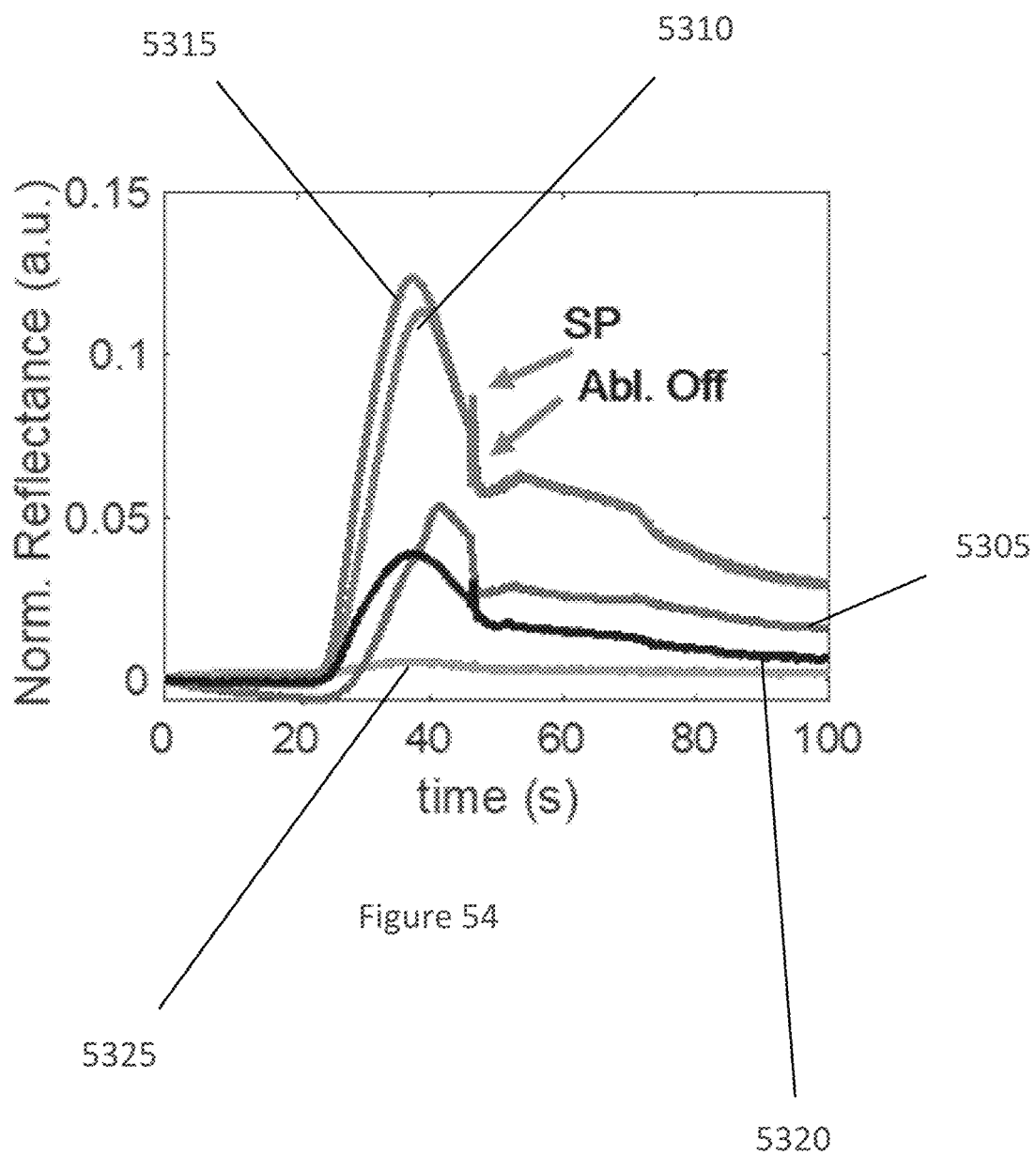
FIG. 54 is a close-up view of the exemplary graph shown in FIG. 53C according to an exemplary embodiment of the present disclosure.

FIG. 54 shows an exemplary graph illustrating a close-up view of the graph shown in FIG. 53C according to an exemplary embodiment of the present disclosure.

Figure 55:
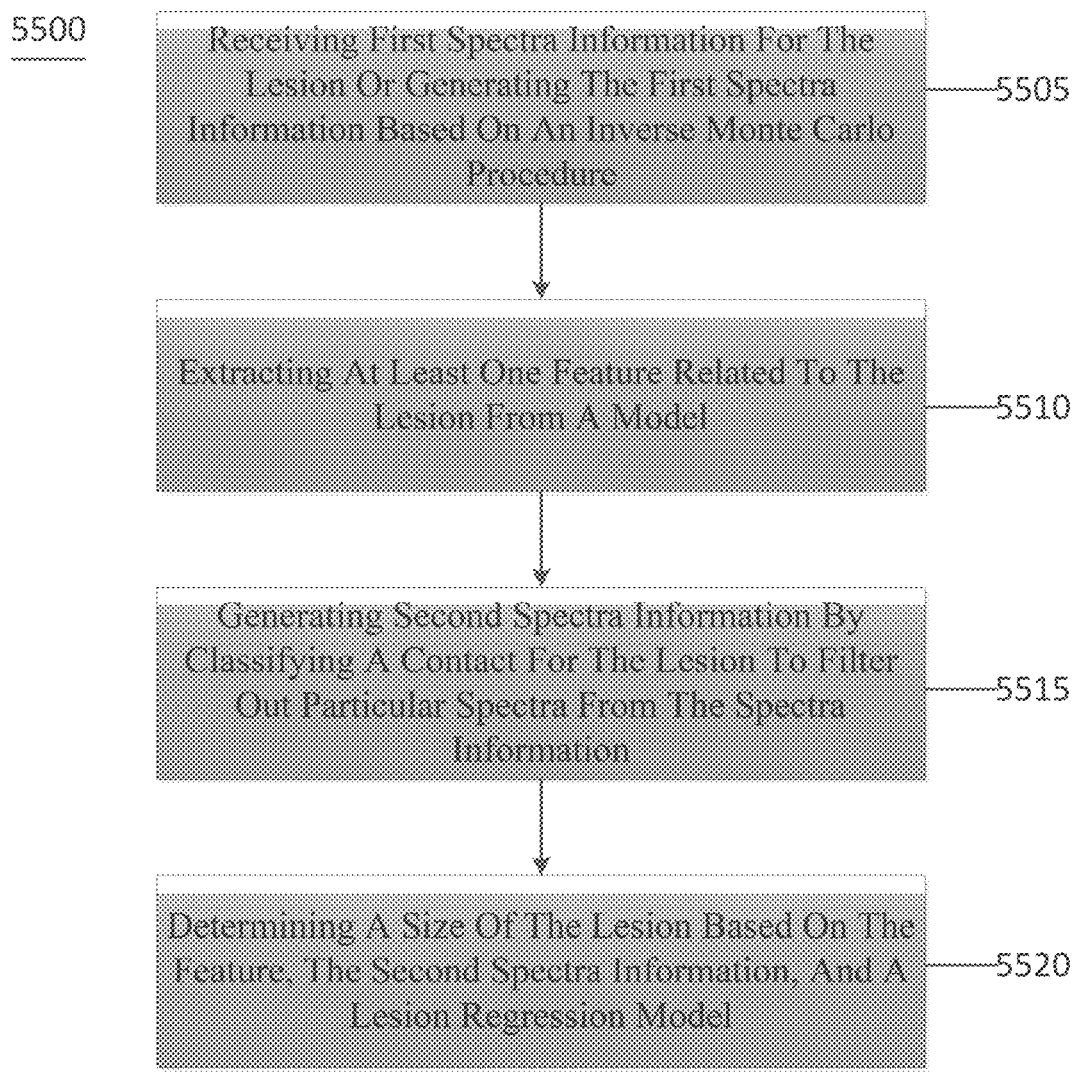
FIG. 55 is a flow diagram of an exemplary method for determining a size of a lesion according to an exemplary embodiment of the present disclosure.

FIG. 55 shows a flow diagram of an exemplary method 5500 for determining a size of a lesion according to an exemplary embodiment of the present disclosure. For example, at procedure 5505, first spectra information for the lesion can be received or first information or first spectra information can be generated based on an inverse Monte Carlo procedure. At procedure 5510, a feature related to the lesion can be extracted from a model. At procedure 5515, second spectra information can be generated by classifying a contact for the lesion to filter out particular spectra from the spectra information. At procedure 5520, a size of the lesion can be determined based on the feature, the second spectra information, and a lesion regression model.

Figure 56:
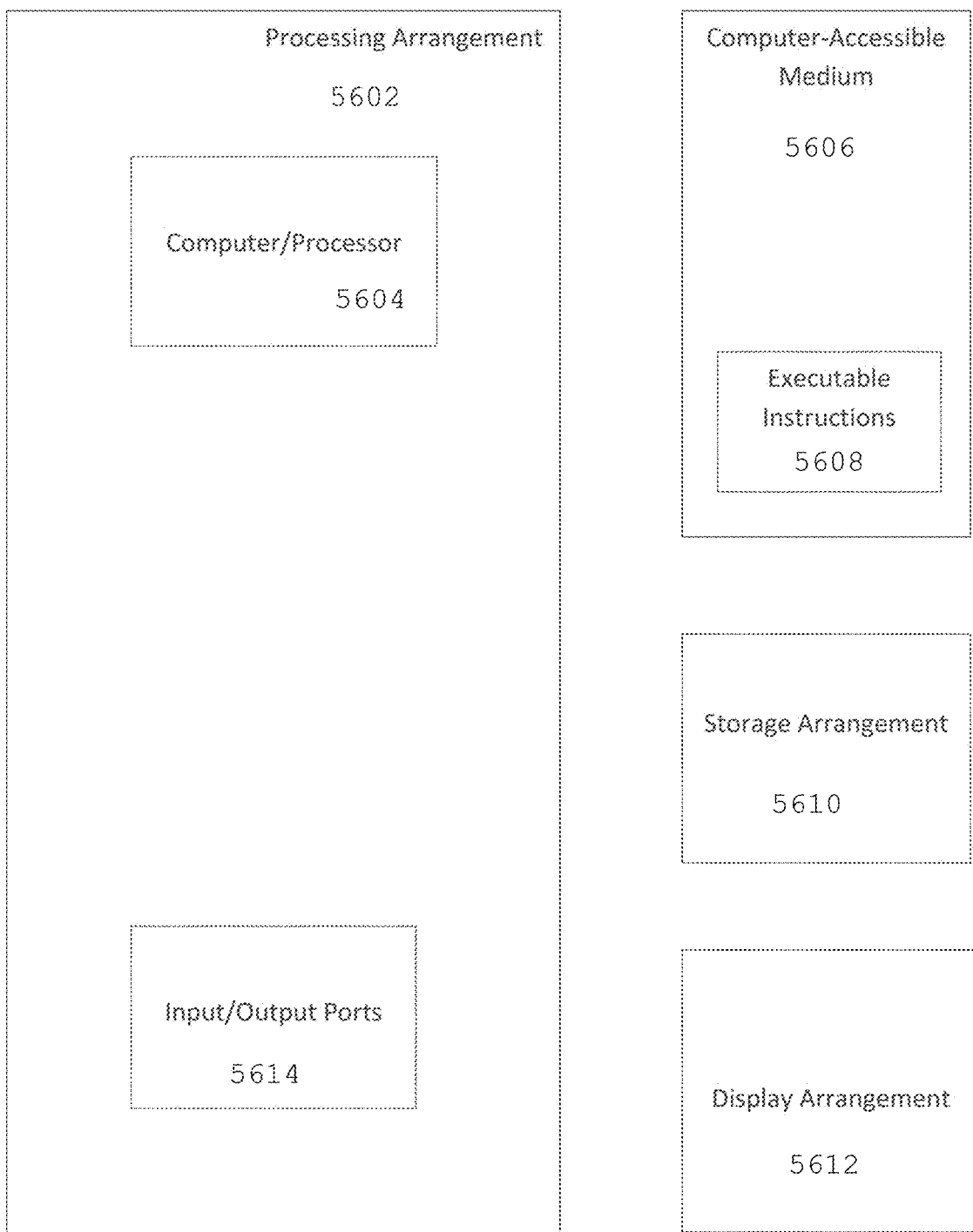
FIG. 56 is an illustration of an exemplary block diagram of an exemplary system in accordance with certain exemplary embodiments of the present disclosure.

FIG. 56 shows a block diagram of an exemplary embodiment of a system according to the present disclosure, which can be utilized either in part or completely with any one or more of the exemplary embodiments of the present disclosure as provided in the enclosed Appendix. For example, exemplary procedures in accordance with the present disclosure described herein can be performed by a processing arrangement and/or a computing arrangement 5602. Such processing/computing arrangement 5602 can be, for example entirely or a part of, or include, but not limited to, a computer/processor 5604 that can include, for example one or more microprocessors, and use instructions stored on a computer-accessible medium (e.g., RAM, ROM, hard drive, or other storage device).

As shown in FIG. 56, for example a computer-accessible medium 5606 (e.g., as described herein above, a storage device such as a hard disk, floppy disk, memory stick, CD-ROM, RAM, ROM, etc., or a collection thereof) can be provided (e.g., in communication with the processing arrangement 5602). The computer-accessible medium 5606 can contain executable instructions 5608 thereon. In addition or alternatively, a storage arrangement 5610 can be provided separately from the computer-accessible medium 5606, which can provide the instructions to the processing arrangement 5602 so as to configure the processing arrangement to execute certain exemplary procedures, processes and methods, as described herein above, for example.

Further, the exemplary processing arrangement 5602 can be provided with or include an input/output arrangement 5614, which can include, for example a wired network, a wireless network, the internet, an intranet, a data collection probe, a sensor, etc. As shown in FIG. 56, the exemplary processing arrangement 5602 can be in communication with an exemplary display arrangement 5612, which, according to certain exemplary embodiments of the present disclosure, can be a touch-screen configured for inputting information to the processing arrangement in addition to outputting information from the processing arrangement, for example. Further, the exemplary display 5612 and/or a storage arrangement 3310 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] H. Celik, V. Ramanan, J. Barry, S. Ghate, V. Leber, S. Oduneye, Y. Gu, M. Jamali, N. Ghugre, J. A. Stainsby, M. Shurrab, E. Crystal, and G. A. Wright, "Intrinsic contrast for characterization of acute radiofrequency ablation lesions," Circulation. Arrhythmia and electrophysiology 7, 718-727 (2014).

[2] D. P. Zipes and J. Jalife, Cardiac electrophysiology: from cell to bedside, Sixth edition. ed. (Elsevier/Saunders, Philadelphia, PA, 2014), pp. xxvi, 1365 pages.

[3] J. Swartling, S. Palsson, P. Platonov, S. B. Olsson, and S. Andersson-Engels, "Changes in tissue optical properties due to radio-frequency ablation of myocardium," Medical & biological engineering & computing 41, 403-409 (2003).

[4] R. M. Singh-Moon, C.; Hendon, C., "Near-infrared spectroscopy integrated catheter for characterization of myocardial tissues: preliminary demonstrations to radiofrequency ablation therapy for atrial fibrillation," Biomed. Opt. Express 6, 2494-2511 (2015).

[5] J. A. Reiffel Am J Med. 2014, 127, e15-16.

[6] P. A. Wolf, R. D. Abbott, W. B. Kannel Stroke. 1991, 22, 983-988.

[7] A. N. Ganesan, N. J. Shipp, A. G. Brooks, P. Kuklik, D. H. Lau, H. S. Lim, T. Sullivan, K. C. Roberts-Thomson, P. Sanders Journal of the American Heart Association. 2013, 2, e004549.

[8] M. A. Wood Circ Arrhythm Electrophysiol. 2011, 4, 257-259.

[9] C. P. Fleming, K. J. Quan, A. M. Rollins Journal of biomedical optics. 2010, 15, 041510.

[10] C. P. Fleming, K. J. Quan, H. Wang, G. Amit, A. M. Rollins Optics express. 2010, 18, 3079-3092.

[11] X. Fu, C. Blumenthal, D. Dosluoglu, Y. T. Wang, M. W. Jenkins, R. Souza, C. Snyder, M. Arruda, A. Rollins Proc. SPIE 2016, 9697.

[12] X. Fu, Z. Wang, H. Wang, Y. T. Wang, M. W. Jenkins, A. M. Rollins Optics letters. 2014, 39, 5066-5069.

[13] D. Herranz, J. Lloret, S. Jimenez-Valero, J. L. Rubio-Guivernau, E. Margallo-Balbas Biomedical optics express. 2015, 6, 3268-3275.

[14] M. Mercader, L. Swift, S. Sood, H. Asfour, M. Kay, N. Sarvazyan American journal of physiology. Heart and circulatory physiology. 2012, 302, H2131-2138.

[15] L. Swift, D. A. Gil, R. Jaimes, 3rd, M. Kay, M. Mercader, N. Sarvazyan Circ Arrhythm Electrophysiol. 2014, 7, 929-937.

[16] D. A. Gil, L. M. Swift, H. Asfour, N. Muselimyan, M. A. Mercader, N. A. Sarvazyan J Biophotonics. 2017, 10, 1008-1017.

[17] N. Muselimyan, L. M. Swift, H. Asfour, T. Chahbazian, R. Mazhari, M. A. Mercader, N. A. Sarvazyan PLoS One. 2016, 11, e0167760.

[18] S. G. Demos, S. Sharareh Optics express. 2008, 16, 15286-15296.

[19] J. R. Mourant, I. J. Bigio, D. A. Jack, T. M. Johnson, H. D. Miller Applied optics. 1997, 36, 5655-5661.

[20] J. R. Mourant, T. M. Johnson, G. Los, I. J. Bigio Physics in medicine and biology. 1999, 44, 1397-1417.

[21] R. P. Singh-Moon, C. P. Hendon I S Biomed Imaging. 2015, 751-755.

[22] R. P. Singh-Moon, C. C. Marboe, C. Hendon Biomed. Opt. Express. 2015, 6, 2494-2511.

[23] R. P. Singh-Moon, X. Yao, C. C. Marboe, C. P. Hendon Biomedical Optics Congress. 2016, Tu3A.39.pdf.

[24] X. Yao, Y. Gan, C. C. Marboe, C. P. Hendon Journal of biomedical optics. 2016, 21.

[25] J. Swartling, S. Palsson, P. Platonov, S. B. Olsson, S. Andersson-Engels Medical & biological engineering & computing. 2003, 41, 403-409.

[26] S. L. J. Thomsen, S. L.; Flock, S. T. Proc. Soc. Photo-Opt. Instrum. Eng. 1202. 1990, 2-10.

[27] W. J. Bowen The Journal of biological chemistry. 1949, 179, 235-245.

[28] H. Celik, V. Ramanan, J. Barry, S. Ghate, V. Leber, S. Oduneye, Y. Gu, M. Jamali, N. Ghugre, J. A. Stainsby, M. Shurrab, E. Crystal, G. A. Wright Circ Arrhythm Electrophysiol. 2014, 7, 718-727.

[29] E. Antonini, M. Brunori, Hemoglobin and myoglobin in their reactions with ligands, North-Holland Pub. Co., Amsterdam, 1971.

[30] T. Dickfeld, R. Kato, M. Zviman, S. Lai, G. Meininger, A. C. Lardo, A. Roguin, D. Blumke, R. Berger, H. Calkins, H. Halperin Journal of the American College of Cardiology. 2006, 47, 370-378.

[31] R. Bai, D. I. B. L, M. Valderrabano, F. Lorgat, H. Mlcochova, R. Tilz, U. Meyerfeldt, P. M. Hranitzky, O. Wazni, P. Kanagaratnam, R. N. Doshi, D. Gibson, A.

Pisapia, P. Mohanty, W. Saliba, F. Ouyang, J. Kautzner, G. J. Gallinghouse, A. Natale J Cardiovasc Electrophysiol. 2012, 23, 820-826.

[32] L. Di Biase, Y. Wang, R. Horton, G. J. Gallinghouse, P. Mohanty, J. Sanchez, D. Patel, M. Dare, R. Canby, L. D. Price, J. D. Zagrodzky, S. Bailey, J. D. Burkhardt, A. Natale J Cardiovasc Electrophysiol. 2009, 20, 1328-1335.

[33] W. Saliba, V. Y. Reddy, O. Wazni, J. E. Cummings, J. D. Burkhardt, M. Haissaguerre, J. Kautzner, P. Peichl, P. Neuzil, V. Schibgilla, G. Noelker, J. Brachmann, L. Di Biase, C. Barrett, P. Jais, A. Natale Journal of the American College of Cardiology. 2008, 51, 2407-2411.

[34] C. P. Fleming, N. Rosenthal, A. M. Rollins, M. Arruda The Journal of Innovations in Cardiac Rhythm Management. 2011, p. 199-201.

[35] C. P. Fleming, H. Wang, K. J. Quan, A. M. Rollins Journal of biomedical optics. 2010, 15, 030516.

[36] T. Lindbergh, M. Larsson, Z. Szabo, H. Casimir-Ahn, T. Stromberg Journal of biomedical optics. 2010, 15, 027009.

[37] Y. Gan, D. Tsay, S. B. Amir, C. C. Marboe, C. P. Hendon Journal of biomedical optics. 2016, 21.

What is claimed is:

1. A method for determining at least one characteristic of at least one tissue, comprising:
   ablating the at least one tissue;
   illuminating, by a source, the at least one tissue during the ablation procedure;
   receiving, by a detector, diffuse reflectance spectra in a wavelength range of 600 nm-1000 nm based on the illumination procedure; and
   using a computer hardware arrangement, continuously determining the at least one characteristic based on the ablation and illumination procedures and the received diffuse reflectance spectra, wherein a separation distance between the source and the detector is between 0.8 mm and 1.7 mm.

2. The method of claim 1, further comprising ablating the at least one tissue using radiofrequency ablation.

3. The method of claim 1, wherein the illumination procedure is performed with a radiation in a visible spectrum.

4. The method of claim 1, further comprising inverting the diffuse reflectance spectra using an inverse Monte Carlo procedure.

5. The method of claim 4, further comprising determining a concentration of at least one of (i) an oxy-myoglobin, (ii) a deoxy-myoglobin or (iii) a met-myoglobin based on the inverted diffuse reflectance spectra.

6. The method of claim 4, further comprising:
   determining a concentration of a met-myoglobin based on the inverted diffuse reflectance spectra; and
   performing at least one of (i) an analysis of variance test or (ii) a Tukey's multiple comparison test on the met-myoglobin concentration.

7. The method of claim 4, further comprising fitting the inverted diffuse reflectance spectra to a wavelength dependent model.

8. The method of claim 7, further comprising receiving a plurality of coefficients based on results of the fitting step, wherein the at least one characteristic is determined based on the coefficients.

9. The method of claim 1, wherein the at least one characteristic includes a classification of the tissue.

10. The method of claim 9, wherein the classification is regarding the at least one tissue having a lesion thereon.

11. The method of claim 1, further comprising at least one of (i) repeating the ablation and illumination procedures until a permanent lesion is formed on the at least one tissue, (ii) determining a baseline diffuse reflectance spectra associated with the at least one tissue before the ablation procedure, (iii) flushing the at least one tissue, or (iv) electrically mapping a surface of the at least on tissue.

12. The method of claim 1, wherein the at least one tissue is illuminated and the diffuse reflectance spectra is received using a single fiber.

13. The method of claim 1, further comprising continuously and simultaneously detecting the ablating the at least one tissue and a return light radiation based on the illuminating of the at least one tissue.

14. A system for determining at least one characteristic of at least one tissue, comprising
   a first electromagnetic radiation source configured to (i) generate at least one first radiation and (ii) provide the at least one first radiation to the at least one tissue so as to partially ablate the at least one tissue;
   a second electromagnetic radiation source configured to (i) generate at least one second radiation, and (ii) provide the at least one second radiation to the at least one tissue;
   a detector arrangement configured to (i) continuously obtain a return radiation from the at least one tissue that is based on the at least one second radiation impacting the at least one tissue and the at least partial ablation caused by the at least one first radiation, (ii) receive diffuse reflectance spectra in a wavelength range of 600 nm-1000 nm based on the illumination procedure, and (iii) provide data associated with at least one further characteristic of the returned radiation; and
   a computer processing arrangement configured to continuously determine the at least one characteristic based on the data and the received diffuse reflectance spectra, wherein a separation distance between the second electromagnetic radiation source and the detector arrangement is between 0.8 mm and 1.7 mm.

15. The system of claim 14, wherein the data includes information as to whether the at least one tissue has been permanently damaged.

16. The system of claim 14, wherein at least one of (i) the at least one second radiation is in a visible spectrum, (ii) the at least one characteristic includes a classification of the tissue, or (iii) the classification is regarding the at least one tissue having a lesion thereon.

17. The system of claim 14, further comprising at least one of (i) at least one flushing arrangement configured to flush the at least one tissue, or (ii) a voltage arrangement configured to generate at least one voltage, wherein the detector arrangement is further configured to obtain a return voltage from the at least one tissue that is based on the at least one second radiation impacting the at least one tissue.

18. The system of claim 14, wherein at least one of the at least one first radiation or the at least one second radiation is provided in a single fiber, and wherein the detector receives the return radiation from the single fiber.

* * * * *